United States Patent
Radhakrishnan et al.

(10) Patent No.: US 11,654,196 B2
(45) Date of Patent: *May 23, 2023

(54) DOSING REGIMENS FOR ECHINOCANDIN CLASS COMPOUNDS

(71) Applicant: Cidara Therapeutics, Inc., San Diego, CA (US)

(72) Inventors: Balasingam Radhakrishnan, Chapel Hill, NC (US); Kenneth Duke James, Jr., Mebane, NC (US); Anuradha Vaidya, Raleigh, NC (US); Karen Polowy, Raleigh, NC (US)

(73) Assignee: Cidara Therapeutics, Inc., San Diego, CA (US)

( * ) Notice: Subject to any disclaimer, the term of this patent is extended or adjusted under 35 U.S.C. 154(b) by 140 days.

This patent is subject to a terminal disclaimer.

(21) Appl. No.: 16/920,316

(22) Filed: Jul. 2, 2020

(65) Prior Publication Data

US 2021/0128670 A1 May 6, 2021

Related U.S. Application Data

(63) Continuation of application No. 16/017,427, filed on Jun. 25, 2018, now Pat. No. 10,702,573, which is a continuation of application No. 15/371,333, filed on Dec. 7, 2016, now Pat. No. 10,016,479, which is a continuation of application No. 14/386,266, filed as application No. PCT/US2013/031678 on Mar. 14, 2013, now Pat. No. 9,526,835.

(60) Provisional application No. 61/707,142, filed on Sep. 28, 2012, provisional application No. 61/612,676, filed on Mar. 19, 2012.

(51) Int. Cl.
| | |
|---|---|
| *A61K 47/18* | (2017.01) |
| *A61K 9/00* | (2006.01) |
| *A61K 9/06* | (2006.01) |
| *A61K 9/107* | (2006.01) |
| *A61K 9/19* | (2006.01) |
| *A61K 9/20* | (2006.01) |
| *A61K 38/12* | (2006.01) |
| *A61K 47/10* | (2017.01) |
| *A61K 47/12* | (2006.01) |
| *A61K 47/26* | (2006.01) |
| *A61K 38/08* | (2019.01) |
| *A61K 47/14* | (2017.01) |
| *A61K 47/36* | (2006.01) |
| *A61M 5/178* | (2006.01) |

(52) U.S. Cl.
CPC .......... *A61K 47/186* (2013.01); *A61K 9/006* (2013.01); *A61K 9/0019* (2013.01); *A61K 9/0053* (2013.01); *A61K 9/0095* (2013.01); *A61K 9/06* (2013.01); *A61K 9/107* (2013.01); *A61K 9/19* (2013.01); *A61K 9/2018* (2013.01); *A61K 38/08* (2013.01); *A61K 38/12* (2013.01); *A61K 47/10* (2013.01); *A61K 47/12* (2013.01); *A61K 47/14* (2013.01); *A61K 47/183* (2013.01); *A61K 47/26* (2013.01); *A61K 47/36* (2013.01); *A61M 5/178* (2013.01)

(58) Field of Classification Search
CPC ........ A61K 38/08; A61K 38/12; A61K 47/10; A61K 47/12; A61K 47/14; A61K 47/183; A61K 47/186; A61K 47/26; A61K 47/36; A61K 9/0019; A61K 9/0053; A61K 9/006; A61K 9/0095; A61K 9/06; A61K 9/107; A61K 9/19; A61K 9/2018; A61M 5/178; A61P 31/10
See application file for complete search history.

(56) References Cited

U.S. PATENT DOCUMENTS

| | | |
|---|---|---|
| 4,427,660 A | 1/1984 | Schiffman et al. |
| 5,166,135 A | 11/1992 | Schmatz |
| 5,378,804 A | 1/1995 | Balkovec et al. |
| 5,399,552 A | 3/1995 | Bouffard |
| 5,514,651 A | 5/1996 | Balkovec et al. |
| 5,516,756 A | 5/1996 | Balkovec et al. |
| 5,541,160 A | 7/1996 | Balkovec et al. |
| 5,652,213 A | 7/1997 | Jamison et al. |
| 5,741,775 A | 4/1998 | Balkovec et al. |
| 5,854,213 A | 12/1998 | Bouffard |
| 5,948,753 A | 9/1999 | Balkovec et al. |
| 6,030,944 A | 2/2000 | Bouffard et al. |
| 6,069,126 A | 5/2000 | Abruzzo et al. |
| 6,268,338 B1 | 7/2001 | Balkovec et al. |
| 6,506,726 B1 | 1/2003 | Dobbins et al. |
| 6,821,951 B2 | 11/2004 | Schwier et al. |
| 7,198,796 B2 | 4/2007 | Stogniew |
| 7,452,861 B2 | 11/2008 | Kaniga |
| 8,722,619 B2 | 5/2014 | James, Jr. et al. |
| 9,217,014 B2 | 12/2015 | James, Jr. et al. |

(Continued)

FOREIGN PATENT DOCUMENTS

| | | |
|---|---|---|
| CN | 1222082 A | 7/1999 |
| CN | 1339959 A | 3/2002 |

(Continued)

OTHER PUBLICATIONS

U.S. Appl. No. 17/029,784, Balkovec et al.
U.S. Appl. No. 17/107,627, James et al.
U.S. Appl. No. 16/920,316, Radhakrishnan et al.
U.S. Appl. No. 17/023,884, Bartizal et al.

(Continued)

*Primary Examiner* — Marcela M Cordero Garcia
(74) *Attorney, Agent, or Firm* — Clark & Elbing LLP

(57) ABSTRACT

The invention features pharmaceutical compositions, methods, and kits featuring dosing gimens and oral dosage formulations for administration of echinocandin class compounds.

3 Claims, 22 Drawing Sheets

(56) References Cited

U.S. PATENT DOCUMENTS

| | | | |
|---|---|---|---|
| 9,526,835 | B2 | 12/2016 | Radhakrishnan et al. |
| 9,676,821 | B2 | 6/2017 | James, Jr. et al. |
| 10,016,479 | B2 | 7/2018 | Radhakrishnan et al. |
| 10,702,573 | B2 | 7/2020 | Radhakrishnan et al. |
| 10,780,144 | B2 | 9/2020 | Bartizal et al. |
| 11,197,909 | B2 * | 12/2021 | Bartizal ............... A61K 9/19 |
| 11,524,980 | B2 * | 12/2022 | Hughes ................. C07K 7/56 |
| 2004/0180965 | A1 | 9/2004 | Borgman et al. |
| 2005/0026819 | A1 | 2/2005 | Kaniga |
| 2005/0043222 | A1 | 2/2005 | Lukacs et al. |
| 2005/0192213 | A1 | 9/2005 | Milton et al. |
| 2005/0261173 | A1 | 11/2005 | Stogniew |
| 2006/0276339 | A1 | 12/2006 | Windsor et al. |
| 2007/0231258 | A1 | 10/2007 | Perakyla et al. |
| 2009/0074859 | A1 | 3/2009 | Patel |
| 2009/0238867 | A1 | 9/2009 | Jenkins et al. |
| 2010/0009009 | A1 | 1/2010 | Young et al. |
| 2010/0075302 | A1 | 3/2010 | Perlin et al. |
| 2013/0011452 | A1 | 1/2013 | Loupenok |
| 2013/0150451 | A1 | 6/2013 | Salamone et al. |
| 2013/0244930 | A1 | 9/2013 | James, Jr. et al. |
| 2015/0024997 | A1 | 1/2015 | James, Jr. et al. |
| 2015/0087583 | A1 | 3/2015 | Radhakrishnan et al. |
| 2016/0045611 | A1 | 2/2016 | Hecht et al. |
| 2016/0058717 | A1 | 3/2016 | Page et al. |
| 2016/0075740 | A1 | 3/2016 | James, Jr. et al. |
| 2016/0213742 | A1 | 7/2016 | Forrest et al. |
| 2017/0151306 | A1 | 6/2017 | Radhakrishnan et al. |
| 2017/0253635 | A1 | 9/2017 | James, Jr. et al. |
| 2018/0256673 | A1 | 9/2018 | Balkovec et al. |
| 2019/0000917 | A1 | 1/2019 | Bartizal et al. |
| 2020/0268833 | A1 | 8/2020 | Bartizal et al. |
| 2021/0002346 | A1 * | 1/2021 | Bartizal ............... C07K 7/60 |
| 2021/0128670 | A1 | 5/2021 | Radhakrishnan et al. |
| 2022/0162263 | A1 * | 5/2022 | James, Jr. ............. A61P 13/02 |

FOREIGN PATENT DOCUMENTS

| | | |
|---|---|---|
| CN | 1355699 A | 6/2002 |
| CN | 101374502 A | 2/2009 |
| CN | 102766198 A | 11/2012 |
| CN | 103889221 A | 6/2014 |
| CN | 104507309 A | 4/2015 |
| JP | 2014-516339 A | 7/2014 |
| JP | 2015-512392 A | 4/2015 |
| WO | WO-96/08507 A1 | 3/1996 |
| WO | WO-2008/093060 A2 | 8/2008 |
| WO | WO-2010/032011 A2 | 3/2010 |
| WO | WO-2010/128096 A1 | 11/2010 |
| WO | WO-2011/025785 A1 | 3/2011 |
| WO | WO-2011/025875 A1 | 3/2011 |
| WO | WO-2011/089214 A1 | 7/2011 |
| WO | WO-2012/119065 A2 | 9/2012 |
| WO | WO-2013/017691 A1 | 2/2013 |
| WO | WO-2013/142279 A1 | 9/2013 |
| WO | WO-2014/113693 A1 | 7/2014 |
| WO | WO-2014/124504 A1 | 8/2014 |
| WO | WO-2015/035102 A2 | 3/2015 |
| WO | WO-2017/049102 A1 | 3/2017 |
| WO | WO-2017/049105 A1 | 3/2017 |
| WO | WO-2017/120471 A1 | 7/2017 |
| WO | WO-2017/161016 A1 | 9/2017 |
| WO | WO-2018/085200 A1 | 5/2018 |
| WO | WO-2018/102407 A1 | 6/2018 |
| WO | WO-2018/144600 A1 | 8/2018 |
| WO | WO-2018/187574 A1 | 10/2018 |
| WO | WO-2018/191692 A1 | 10/2018 |
| WO | WO-2019/014333 A1 | 1/2019 |
| WO | WO-2019/027498 A1 | 2/2019 |

OTHER PUBLICATIONS

Lee et al., "First Three Reported Cases of Nosocomial Fungemia Caused by *Candida auris*," J Clin Microbiol. 49(9):3139-42 (2011).

Zhao et al., "CD101: a novel long-acting echinocandin," Cell Microbiol. 18(9):1308-16 (2016).

Walpole et al., "The weight of nations: an estimation of adult human biomass," BMC Public Health. 12:439 (2012) (6 pages).

Verweij et al., "Efficacy of LY303366 against amphotericin B-susceptible and -resistant *Aspergillus fumigatum* a murine model of invasive aspergillosis," Antimicrob Agents Chemother. 42(4): 873-78 (1998).

Uzun et al., "In vitro activity of a new echinocandin, LY303366, compared with those of amphotericin B and fluconazole against clinical yeast isolates," Antimicrob Agents Chemother. 41(5): 1156-7 (1997).

Thye, "The safety and single-dose pharmacokinetics of CD101 IV: results from a phase 1, dose-escalation study," 26th European Congress of Clinical Microbiology and Infectious Diseases, Amsterdam, Netherlands, Apr. 9-12, 2016. Retrieved from <http://www.cidara.com/wp-content/uploads/2016/04/The-safety-and-single-dose-pharmacokinetics-of-CD101-IV-results-from-a-phase-1-dose-escalation-study.pdf> (12 pages).

Strickley, "Solubilizing excipients in oral and injectable formulations," Pharm Res. 21(2):201-30 (2004).

Sandison et al., "Safety and Pharmacokinetics of Single and Multiple Doses of CD101 IV: Results from Two Phase 1 Dose-Escalation Studies," 2016 American College of Clinical Pharmacy Annual Meeting, Oct. 23-26, Hollywood, Florida. Poster 258 (2016) (1 page).

Sandison et al., "Safety and Pharmacokinetics of Single and Multiple Doses of CD101 IV: Results from Two Phase 1 Dose-Escalation Studies," 19th Immunocompromised Host Society Symposium, 14th Forum on Fungal Infection in the Clinical Practice, Nov. 13-15, Santiago, Chile (2016) (1 page).

Sandison et al., "Safety and Pharmacokinetics of Multiple Doses of CD101 IV: Results From a Phase 1, Dose-Escalation Study," ASM Microbe, June 16-20, 2016, Boston, Massachusetts. Abstract LB-057 (2016) (1 page).

Sandison et al., "Safety and Pharmacokinetics of CD101 IV, a Novel Echinocandin, in Healthy Adults," Antimicrob Agents Chemother. 61(2):e01627-16 (2017) (11 pages).

Sandison et al., "Pharmacokinetics, Safety, and Target Attainment of Single and Multiple Doses of CD101 IV—a Novel, Once-Weekly Echinocandin," 58th Annual Meeting of the American Society of Hematology, Dec. 5-8, San Diego, California. Abstract 2197 (2016) (1 page).

Rodriguez et al., "The Synthesis of Water Soluble Prodrugs Analogs of Echinocandin B," Bioorg Med Chem Lett. 9(13):1863-1868 (1999).

PubChem: Substance Record for SID 144216468, available Oct. 8, 2012, retrieved Feb. 9, 2017 (5 pages).

Pfizer Inc., "Eraxis (anidulafungin) for Injection," <http://dailymed.nlm.nih.gov/dailymed/archives/fdaDrugInfo.cfm?archiveid=4744>, revised May 2007, retrieved on Oct. 1, 2015 (21 pages).

Pfaller et al., "Activity of a long-acting echinocandin, CD101, determined using CLSI and EUCAST reference methods, against *Candida* and *Aspergillus* spp., including echinocandin- and azole-resistant isolates," J Antimicrob Chemother. 71(10):2868-73 (2016).

Partial supplementary European Search Report for European Patent Application No. 12751994.0, dated Mar. 10, 2015 (5 pages).

Ong et al., "Preclinical Evaluation of the Stability, Safety, and Efficacy of CD101, a Novel Echinocandin," Antimicrob Agents Chemother. 60(11):6872-9 (2016).

Office Action for U.S. Appl. No. 15/371,333, dated Sep. 29, 2017 (23 pages).

Office Action and English Translation for Russian Patent Application No. 2017128118, dated Jun. 17, 2019 (8 pages).

Office Action and English translation for Chinese Patent Application 201380026168.3, dated Sep. 15, 2015 (20 pages).

Metzler et al., "Comparison of minimal inhibitory and mutant prevention drug concentrations of 4 fluoroquinolones against clinical isolates of methicillin-susceptible and -resistant *Staphylococcus aureus*," Int J Antimicrob Agents. 24(2):161-7 (2004).

Lakota et al., "Pharmacokinetic-Pharmacodynamic Target Attainment Analyses to Support the Selection of Extended-Interval CD101

(56) References Cited

OTHER PUBLICATIONS

Dosing Regimens," IDWeek, Oct. 26-30, 2016, New Orleans, Louisiana. Poster No. 1994 (2016) (2 pages).
Krishnan et al., "CD101, a novel echinocandin with exceptional stability properties and enhanced aqueous solubility," J Antibiot (Tokyo). 70(2):130-5 (2017).
Kathuria et al., "Multidrug-Resistant Candida auris Misidentified as Candida haemulonii: Characterization by Matrix-Assisted Laser Desorption Ionization-Time of Flight Mass Spectrometry and DNA Sequencing and Its Antifungal Susceptibility Profile Variability by Vitek 2, CLSI Broth Microdilution, and Etest Method," J Clin Microbiol. 53(6):1823-30 (2015).
Jamison et al., "The synthesis and antifungal activity of nitrogen containing hemiaminal ethers of LY303366," J Antibiot (Tokyo). 51(2): 239-42 (1998).
James et al., "Biafungin (CD101), a novel echinocandin, displays a long half-life in the chimpanzee, suggesting a once-weekly IV dosing option," 54th Interscience Conference on Antimicrobial Agents and Chemotherapy, Sep. 5-9, Washington D.C., Abstract A-694, retrieved from <http://n33px2pjph02hfyxt1xmwn4m.wpengine.netdna-cdn.com/wp-content/uploads/2014/12/A-694.-Biafungin-CD101-a-Novel-Echinocandin-Displays-a-Long-Half-life-in-the-Chimpanzee-Suggesting-a-Once-Weekly-IV-Dosing-Option.pdf> (2014) (2 pages).
International Search Report and Written Opinion for International Application No. PCT/US2013/031678, dated Jun. 12, 2013 (19 pages).
International Search Report and Written Opinion for International Application No. PCT/US2012/027451, dated Jun. 20, 2012 (16 pages).
International Preliminary Report on Patentability for International Patent Application No. PCT/US2012/027451, dated Jan. 28, 2014 (7 pages).
International Preliminary Report on Patentability for International Application No. PCT/US2013/031678, dated Sep. 23, 2014 (11 pages).
Heikkilä et al., "The prevalence of onychomycosis in Finland," Br J Dermatol. 133(5):699-703 (1995).
Guo et al., "Synthesis and antifungal activities of glycosylated derivatives of the cyclic peptide fungicide caspofungin," ChemMedChem. 7(8):1496-503 (2012).
GenBank Accesion No. AYN77793.1, "1,3-beta-D-glucan synthase [[Candida] auris]," <https:///www.ncbi.nlm.nih.gov/protein/AYN77793.1>, dated Oct. 16, 2018, retrieved Oct. 16, 2020 (2 pages).
Fujie et al., "FR131535, a novel water-soluble echinocandin-like lipopeptide: synthesis and biological properties," Bioorg Med Chem Lett. 11(3):399-402 (2001).
Extended European Search Report for International Patent Application No. 12751994.0, dated Jul. 27, 2015 (8 pages).

Extended European Search Report for European Patent Application No. 17867743.1, dated Jun. 25, 2020 (12 pages).
Extended European Search Report for European Application No. 13764974.5, dated Oct. 26, 2015 (7 pages).
Espinel-Ingroff, "Comparison of in vitro activities of the new triazole SCH56592 and the echinocandins MK-0991 (L-743,872) and LY303366 against opportunistic filamentous and dimorphic fungi and yeasts," J Clin Microbiol. 36(10): 2950-6 (1998).
English translation of Search Report for Chinese Application No. 201280021321.9, dated Jan. 6, 2015 (7 pages).
English translation of Office Action for Japanese Patent Application No. 2013-556894, dated Apr. 21, 2015 (2 pages).
Douglas et al., "Identification of the FKS1 gene of Candida albicans as the essential target of 1,3-beta-D-glucan synthase inhibitors," Antimicrob Agents Chemother. 41(11):2471-9 (1997).
Denning, "Echinocandin antifungal drugs," Lancet. 362(9390):1142-51 (2003).
Denning et al., "Infectious Disease. How to bolster the antifungal pipeline," Science. 347(6229):1414-6 (2015) (4 pages).
Cushion, "Prevention of Pneumocystis Pneumonia (PCP) by the novel Echinocandin, CD101," American Society for Microbiology Microbe 2016, Jun. 17, 2016 (17 pages).
Cushion et al., "Efficacy of CD101, a novel Echinocandin, in prevention of *Pneumocystis* Pneumonia (PCP): thwarting the biphasic life cycle of *Pneumocystis*," Annual Meeting of the American Society of Hematology, Dec. 3-6, San Diego, California, Abstract 3396. Blood. 128(22) (2016) (1 page).
Cuenca-Estrella et al., "Susceptibility of fluconazole-resistant clinical isolates of *Candida* spp. to echinocandin LY303366, itraconazole and amphotericin B," J Antimicrob Chemother. 46(3): 475-7 (2000).
Crandon et al., "Bronchopulmonary disposition of intravenous voriconazole and anidulafungin given in combination to healthy adults," Antimicrob Agents Chemother. 53(12):5102-7 (2009).
Communication pursuant to Article 94(3) EPC for European Patent Application No. 13764974.5, dated Nov. 18, 2016 (4 pages).
Chowdhary et al., "Multidrug-resistant Candida auris: 'new kid on the block' in hospital-associated infections?" J Hosp Infect. 94(3):209-212 (2016).
Chatterjee et al., "Draft genome of a commonly misdiagnosed multidrug resistant pathogen *Candida auris*," BMC Genomics. 16:686 (2015) (16 pages).
Bouffard et al., "Synthesis and antifungal activity of novel cationic pneumocandin Bo derivatives," J Med Chem. 37(2): 222-5 (1994).
Boikov et al., "In vitro activity of the novel echinocandin CD101 at pH 7 and 4 against *Candida* spp. isolates from patients with vulvovaginal candidiasis," J Antimicrob Chemother. 72(5):1355-8 (2017).
Barrett, "From natural products to clinically useful antifungals," Biochim Biophys Acta. 1587(2-3):224-33 (2002).

\* cited by examiner compound 4 compound 5 compound 6 compound 7

Compound 8

Compound 9

Compound 10 compound 13 compound 14 compound 22 compound 23 compound 24 compound 25 compound 26 compound 27 compound 28 compound 29 compound 30 compound 31 compound 32 compound 33 compound 34 compound 35 compound 36 compound 37 compound 38 compound 39 compound 40 compound 41 compound 42 compound 43 compound 44 compound 45 compound 46

DOSING REGIMENS FOR ECHINOCANDIN CLASS COMPOUNDS

BACKGROUND OF THE INVENTION

This invention relates to the field of treatment of fungal infections.

The need for novel antifungal treatments is significant, and is especially critical in the medical field. Immunocompromised patients provide perhaps the greatest challenge to modern health care delivery. During the last three decades there has been a dramatic increase in the frequency of fungal infections in these patients (Herbrecht, Eur. J. Haematol., 56:12, 1996; Cox et al., Curr. Opin. Infect. Dis., 6:422, 1993; Fox, ASM News, 59:515, 1993). Deep-seated mycoses are increasingly observed in patients undergoing organ transplants and in patients receiving aggressive cancer chemotherapy (Alexander et al., Drugs, 54:657, 1997). The most common pathogens associated with invasive fungal infections are the opportunistic yeast, *Candida albicans*, and the filamentous fungus, *Aspergillus fumigatus* (Bow, Br. J. Haematol., 101:1, 1998; Warnock, J. Antimicrob. Chemother., 41:95, 1998). There are an estimated 200,000 patients per year who acquire nosocomial fungal infections (Beck-Sague et al., J. Infect. Dis., 167:1247, 1993). Also adding to the increase in the numbers of fungal infections is the emergence of Acquired Immunodeficiency Syndrome (AIDS) where virtually all patients become affected with some form of mycoses during the course of the disease (Alexander et al., Drugs, 54:657, 1997; Hood et al., J. Antimicrob. Chemother., 37:71, 1996). The most common organisms encountered in these patients are *Cryptococcus neoformans, Pneumocystis carinii*, and *C. albicans* (HIV/AIDS Surveillance Report, 1996, 7(2), Year-End Edition; Polis, M. A. et al., AIDS: Biology, Diagnosis, Treatment and Prevention, fourth edition, 1997). New opportunistic fungal pathogens such as *Penicillium marneffei, C. krusei, C. glabrata, Histoplasma capsulatum*, and *Coccidioides immitis* are being reported with regularity in immunocompromised patients throughout the world.

The development of antifungal treatment regimens has been a continuing challenge. Currently available drugs for the treatment of fungal infections include amphotericin B, a macrolide polyene that interacts with fungal membrane sterols, flucytosine, a fluoropyrimidine that interferes with fungal protein and DNA biosynthesis, and a variety of azoles (e.g., ketoconazole, itraconazole, and fluconazole) that inhibit fungal membrane-sterol biosynthesis (Alexander et al., Drugs, 54:657, 1997). Even though amphotericin B has a broad range of activity and is viewed as the "gold standard" of antifungal therapy, its use is limited due to infusion-related reactions and nephrotoxicity (Warnock, J. Antimicrob. Chemother., 41:95, 1998). Flucytosine usage is also limited due to the development of resistant microbes and its narrow spectrum of activity. The widespread use of azoles is causing the emergence of clinically-resistant strains of *Candida* spp. Due to the problems associated with the current treatments, there is an ongoing search for new treatments.

When the echinocandin caspofungin was approved for sale in 2001, it represented the first new class of antifungal agents to be approved in over a decade. Since that time, two other echinocandin antifungals, anidulafungin and micafungin, have been approved in various markets. Each agent in this class of compound acts by inhibition of β-1, 3-glucan synthase, which is a key enzyme in the synthesis of glucan in the cell wall of many fungi. All three of these drugs are made semisynthetically, starting with natural products obtained through fermentation.

The echinocandins are a broad group of antifungal agents that typically are comprised of a cyclic hexapeptide and lipophilic tail, the latter of which is attached to the hexapeptide core through an amide linkage. Although many echinocandins are natural products, the clinically relevant members of this class have all been semisynthetic derivatives. Although the naturally occurring echinocandins possess some degree of anti-fungal activity, they have not been suitable as therapeutics, primarily because of poor aqueous solubility, insufficient potency, and/or hemolytic action. The approved echinocandins are the products of intense efforts to generate derivatives or analogs that maintain or improve upon the glucan synthase inhibition, but do not cause the hemolytic effects. As therapeutic agents, they are attractive compounds in terms of their systemic half-lives, large therapeutic windows, safety profiles, and relative lack of interactions with other drugs. Unfortunately, the poor intestinal absorption of these compounds has relegated them to delivery by intravenous infusion. Although patients receiving these drugs are often hospitalized with serious infections, the ability to transition patients from intravenous delivery in a hospital setting to oral delivery in a home setting would be very desirable, especially considering the course of the regimen commonly exceeds 14 days. In addition, an oral echinocandin may expand the use of this drug class to include patients that present with mild fungal infections.

SUMMARY OF THE INVENTION

We have discovered dosing regimens and oral dosage formulations for administration of echinocandin class compounds.

In a first aspect, the invention features a method of treating a fungal infection in a subject by (i) administering a loading-dose of an echinocandin class compound to the subject; and (ii) administering one or more maintenance doses of the echinocandin class compound to the subject, wherein each of the loading-dose and the maintenance doses are administered in an amount that together are sufficient to treat the fungal infection. For example, the loading dose can be administered by injection (e.g., subcutaneously) or orally followed by maintenance dosing administered orally, intravenously, nasally, subcutaneously or transdermally. In one embodiment, the loading-dose is intravenously administered. For example, the intravenously (e.g., as a bolus or infusion) administered loading-dose can be administered in an amount sufficient to produce a mean steady-state concentration of the echinocandin class compound in plasma of from 100 ng/mL to 20,000 ng/mL (e.g., from 100 to 500, 400 to 1,000, 800 to 3,000, 2,000 to 7,000, 6,000 to 10,000, 8,000 to 14,000, or 12,000 to 20,000 ng/mL); can be intravenously administered to the subject in an amount of echinocandin class compound per body weight of subject of from 0.5 mg/kg to 20 mg/kg (e.g., from 0.5 to 2.0, 1.0 to 4.0, 3.0 to 10, 8.0 to 15, or 13 to 20 mg/kg); and/or can be intravenously administered to the subject in an amount of echinocandin class compound of from 25 mg to 1,400 mg (e.g., from 25 to 50, 40 to 80, 75 to 130, 125 to 170, 150 to 200, 190 to 250, 230 to 500, 450 to 750, 650 to 1,000, or 900 to 1,400 mg) over a 24 hour period. Alternatively, the loading-dose can be orally administered. For example, the orally administered to the subject in an amount of echinocandin class compound of from 250 mg to 4,000 mg (e.g., from 250 to 500, 400 to 800, 750 to 1300, 1250 to 1700, or 1,500 to 4,000 mg) over a 24 hour period. In an embodiment of any of the above methods, the maintenance doses can be administered over a period of from 2 to 45 days (e.g., 2 to 10, 7 to 14, 10 to 21, or 18 to 30 days, or 24 to 45 days) following the initiation of the treatment. The maintenance doses can be administered, for example, at a rate of from once per week to three times daily (e.g., once per every 5-7 days, once per every 3 days, every other day, once daily, twice daily, or three times daily). The echinocandin class compound can be a compound of any of formulas (I), (II), (III), (IV), (V), (VI), (VII), (VIIII), or (IX), or selected from anidulafungin, caspofungin, micafungin, compound 22, or any other echinocandin class compound described herein, or a pharmaceutically acceptable salt thereof. In certain embodiments, the loading dose includes intravenous administration of from 50 to 400 mg (e.g., 50 to 125, 75 to 300, or 100 to 400 mg) of compound 22, or a pharmaceutically acceptable salt thereof. In some embodiments, the method includes maintenance dosing that includes oral administration of from 250 to 800 mg (e.g., 250 to 300, 275 to 450, 425 to 625, or 600 to 800 mg) of compound 22, or a pharmaceutically acceptable salt thereof, every day or every other day or every three days. In some embodiments, the method includes maintenance dosing that includes subcutaneous administration of from 25 to 150 mg (e.g., 25 to 30, 35 to 45, 30 to 70, 50 to 100, 70 to 120 or 110 to 150 mg) of compound 22, or a pharmaceutically acceptable salt thereof, every day or every other day or once every three days or once every five days. In some embodiments, the method includes maintenance dosing that includes IV bolus administration of from 25 to 150 mg (e.g., 25 to 30, 35 to 45, 30 to 70, 50 to 100, 70 to 120 or 110 to 150 mg) of compound 22, or a pharmaceutically acceptable salt thereof, every day or every other day or every three days or once every five days.

In one particular embodiment of any of the above methods, step (ii) includes orally administering to the subject a pharmaceutical composition in unit dosage form including: (a) a drug selected from echinocandin class compounds, and salts thereof; and (b) from 0.5% to 90% (w/w) (e.g., from 0.5% to 5%, 2.5% to 7.5%, 7% to 12%, 10% to 25%, 25% to 35%, 30% to 50%, or 40% to 90% (w/w)) of an additive, wherein the additive is present in an amount sufficient to increase the oral bioavailability of the echinocandin class compounds, or salt thereof. In particular embodiments, the additive is selected from acyl carnitines, alkyl saccharides, ester saccharides, amido fatty acids, ammonium sulfonate surfactants, bile acids and salts (including cholic acid and salts thereof), chitosan and derivatives thereof, fatty acids and salts or esters thereof, glycerides, hydrophilic aromatic alcohols, pegylated phospholipids, peptide epithelial tight junction modulators, phospholipids, polyethylene glycol alkyl ethers, polyglycolized glycerides, polyglycerol fatty acid esters, polysorbate surfactants, carboxylic acids, polyethylene glycols, and mixtures thereof.

In particular embodiments of the above method, the loading-dose is administered intravenously (e.g., by intravenous bolus or infusion) and the maintenance dose is administered orally; the loading-dose is administered subcutaneously and the maintenance dose is administered orally; the loading-dose is administered intravenously (e.g., by intravenous bolus or infusion) and the maintenance dose is administered subcutaneously; the loading-dose is administered subcutaneously and the maintenance dose is administered subcutaneously; the loading-dose is administered orally and the maintenance dose is administered orally; or the loading-dose is administered intravenously (e.g., by intravenous bolus or infusion) and the maintenance dose is administered by injection (e.g., by intravenous bolus or infusion, or by subcutaneous injection). In particular embodiments of the method including an intravenous bolus, the amount of echinocandin class compound administered is from 50 mg to 500 mg (e.g., from 50 to 100, 100 to 200, 150 to 225, 200 to 300, 275 to 400, or 400 to 500 mg) in a single bolus injection.

In a related aspect, the invention features a pharmaceutical composition in unit dosage form including: (a) an echinocandin class compound, or a pharmaceutically acceptable salt thereof; and (b) from 0.5% to 90% (w/w) (e.g., from 0.5% to 5%, 2.5% to 7.5%, 7% to 12%, 10% to 25%, 25% to 35%, 30% to 50%, or 40% to 90% (w/w)) of an additive, wherein the additive is present in an amount sufficient to increase the oral bioavailability of the echinocandin class compound, or salt thereof. In particular embodiments, the additive is selected from acyl carnitines, alkyl saccharides, ester saccharides, amido fatty acids, ammonium sulfonate surfactants, bile acids and salts (including cholic acid and salts thereof), chitosan and derivatives thereof, fatty acids and salts or esters thereof, glycerides, hydrophilic aromatic alcohols, pegylated phospholipids, peptide epithelial tight junction modulators, phospholipids, polyethylene glycol alkyl ethers, polyglycolized glycerides, polyglycerol fatty acid esters, polysorbate surfactants, carboxylic acids, polyethylene glycols, and mixtures thereof. In certain embodiments, the pharmaceutical composition can include from 2% to 90% (w/w) (e.g., 3% to 6%, 3% to 8%, 5% to 12%, 8% to 16%, 15% to 25%, 25% to 35%, 35% to 65%, or 65% to 90% (w/w)) alkyl saccharide or ester saccharide, optionally further including from 0.5% to 15% (w/w) (e.g., 0.5% to 2.5%, 1% to 4%, 3% to 7%, 5% to 10%, 7% to 12%, or 11% to 15% (w/w)) polysorbate surfactant. In particular embodiments, the pharmaceutical composition can include from 2% to 90% (w/w) (e.g., 3% to 6%, 3% to 8%, 5% to 12%, 8% to 16%, 15% to 25%, 25% to 35%, 35% to 65%, or 65% to 90% (w/w)) glyceride, optionally further including from 0.5% to 15% (w/w) (e.g., 0.5% to 2.5%, 1% to 4%, 3% to 7%, 5% to 10%, 7% to 12%, or 11% to 15% (w/w)) polysorbate surfactant. In some embodiments, the pharmaceutical composition can include from 1% to 90% (w/w) (e.g., 2% to 5%, 3% to 8%, 5% to 12%, 10% to 18%, 15% to 24%, 20% to 30%, 25% to 35%, 30% to 50%, 50% to 70%, or 65% to 90% (w/w)) fatty acid, or a salt or ester thereof. In certain embodiments, the pharmaceutical composition can include from 1% to 90% (w/w) (e.g., 2% to 6%, 5% to 12%, 10% to 18%, 15% to 25%, 20% to 35%, 30% to 45%, 40% to 60%, or 55% to 90% (w/w)) acyl carnitine, optionally further including a buffer to form, upon exposure to water, a solution having a pH of from 2.5 to 8. In some embodiments, the pharmaceutical composition can include from 1% to 90% (w/w) (e.g., 2% to 5%, 3% to 8%, 5% to 12%, 10% to 18%, 15% to 24%, 20% to 30%, 25% to 35%, 30% to 50%, 50% to 70%, or 65% to 90% (w/w)) carboxylic acid, or a salt thereof. In certain embodiments, the pharmaceutical composition can include from 1% to 90% (w/w) (e.g., 2% to 5%, 3% to 8%, 5% to 12%, 10% to 18%, 15% to 24%, 20% to 30%, 25% to 35%, 30% to 50%, 50% to 70%, or 65% to 90% (w/w)) polyethylene glycols. In particular embodiments, the pharmaceutical composition includes an alkyl saccharide or ester saccharide, wherein the ratio by weight of the echinocandin class compound to the alkyl saccharide, or to the ester saccharide, is from 1:1 to 1:20 (e.g., from 1:1 to 1:3, 1:2 to 1:5, 1:4 to 1:10, or 1:5 to 1:20). In certain embodiments, the pharmaceutical composition includes a glyceride, wherein the ratio by weight of the echinocandin class compound to the glyceride is from 1:1 to 1:20 (e.g., from 1:1 to 1:3, 1:2 to 1:5, 1:4 to 1:10, or 1:5 to 1:20). In some embodiments, the pharmaceutical composition includes a fatty acid, or a salt or ester thereof, wherein the ratio by weight of the echinocandin class compound to the fatty acid, or a salt thereof, is from 1:1 to 1:30 (e.g., from 1:1 to 1:3, 1:2 to 1:5, 1:4 to 1:10, or 1:10 to 1:30). In particular embodiments, the pharmaceutical composition includes an acyl carnitine (e.g., palmitoyl carnitine or lauroyl carnitine), wherein the ratio by weight of the echinocandin class compound to the acyl carnitine is from 1:1 to 1:30 (e.g., from 1:1 to 1:3, 1:2 to 1:5, 1:4 to 1:10, or 1:10 to 1:30). In particular embodiments, the pharmaceutical composition includes a carboxylic acid (e.g., citric acid, succinic acid, tartaric acid, fumaric acid, maleic acid, malonic acid, glutaric acid, adipic acid, lactic acid, malic acid, L-glutamic acid, L-aspartic acid, gluconic acid, glucuronic acid, salicylic acid, or mixtures thereof), wherein the ratio by weight of the echinocandin class compound to the carboxylic acid is from 1:1 to 1:30 (e.g., from 1:1 to 1:3, 1:2 to 1:5, 1:4 to 1:10, or 1:10 to 1:30). In particular embodiments, the pharmaceutical composition includes a polyethylene glycol (e.g., PEG 100, PEG 400, PEG 1,000, etc.), wherein the ratio by weight of the echinocandin class compound to the polyethylene glycol is from 1:1 to 1:30 (e.g., from 1:1 to 1:3, 1:2 to 1:5, 1:4 to 1:10, or 1:10 to 1:30).

In an embodiment of any of the above pharmaceutical compositions, the unit dosage form includes from 50 to 4,000 mg (e.g., from 50 to 300, from 250 to 750, from 500 to 1,500, or from 1,000 to 4,000 mg) of the echinocandin class compound. The unit dosage form can be formulated for immediate release.

The pharmaceutical composition can contain an echinocandin class compound of any of formulas (I), (II), (III), (IV), (V), (VI), (VII), (VIIII), or (IX), or selected from anidulafungin, caspofungin, micafungin, compound 22, or any other echinocandin class compound described herein, or a pharmaceutically acceptable salt thereof.

In an embodiment of any of the above pharmaceutical compositions, the additive is present in an amount sufficient to produce, upon oral administration to a subject, a mean bioavailability of 3% to 30% (e.g., 4±2%, 6±2%, 8±2%, 10±2%, 12±3%, 15±3%, 18±4%, 22±6%, or 27±3%)

In a related aspect, the invention features a method of treating a fungal infection in a subject by orally administering to the subject a pharmaceutical composition of the invention, wherein the pharmaceutical composition is administered in an amount effective to treat the infection.

The invention further features a method of treating a fungal infection in a subject by subcutaneously administering to the subject an aqueous solution including compound 22, or a pharmaceutically acceptable salt thereof, in an amount that is sufficient to treat the fungal infection. In particular embodiments, the aqueous solution can be subcutaneously administered to the subject twice daily, daily, every other day, every three days, or once weekly over a period of at least 2 weeks, 3 weeks, 4 weeks, 2 months, 3 months, or 4 months. The aqueous solution can include from 25 mg/mL to 500 mg/mL of compound 22, or a pharmaceutically acceptable salt thereof (e.g., 30±5, 40±10, 50±10, 60±10, 70±10, 80±10, 100±15 mg/mL, 130±20 mg/mL, 160±30 mg/mL, 190±30 mg/mL, 250±50 mg/mL or 400±100 mg/mL). In particular embodiments, from 0.05 mL to 2.0 mL of the aqueous solution are administered to the subject daily. In some embodiments, the amount of compound 22, or a pharmaceutically acceptable salt thereof, subcutaneously administered to the subject is from 10 mg to 100 mg (e.g., 15±5, 25±10, 50±20, 70±25, or 80±20 mg) daily.

In a related aspect, the invention features a device for injecting an aqueous solution of compound 22, or a pharmaceutically acceptable salt thereof, into a subject, including a container holding from 0.05 mL to 10 mL of the aqueous solution (e.g., from 0.2 mL to 0.5 mL, 0.5 mL to 3 mL, 2 mL to 5 mL, 4 mL to 7 mL, or 6 mL to 10 mL of the aqueous solution) and a needle. For example, the device can be a pen injector device holding a prefilled cartridge, such as a metered pen device with a micro needle. In particular embodiments, the container is a cartridge. In particular embodiments, the device is a prefilled syringe containing 0.05 mL to 1 mL (e.g., from 0.2 mL to 0.5 mL, or 0.5 mL to 1 mL) of the aqueous solution. In still other embodiments, the aqueous solution includes from 25 mg/mL to 500 mg/mL of compound 22, or a pharmaceutically acceptable salt thereof e.g., (30±5, 40±10, 50±10, 60±10, 70±10, 80±10, 100±15 mg/mL, 130±20 mg/mL, 160±30 mg/mL, 190±30 mg/mL, 250±50 mg/mL or 400±100 mg/mL).

The invention further features a method of treating a fungal infection in a subject by administering to the subject an intravenous bolus of an aqueous solution including compound 22, or a pharmaceutically acceptable salt thereof, in an amount that is sufficient to treat the fungal infection. In particular embodiment, the aqueous solution includes from 25 mg/mL to 500 mg/mL (e.g., 30±5, 40±10, 50±10, 60±10, 70±10, 80±10, 100±15 mg/mL, 130±20 mg/mL, 160±30 mg/mL, 190±30 mg/mL, 250±50 mg/mL or 400±100 mg/mL) of compound 22, or a pharmaceutically acceptable salt thereof. The bolus injection can be administered to the subject daily, every other day, or every three days, or every 4-7 days, or every week over a period of at least 2 weeks, 3 weeks, 4 weeks, 2 months, 3 months, or 4 months. In some embodiments, the amount of compound 22, or a pharmaceutically acceptable salt thereof, administered as an intravenous bolus to the subject is from 25 mg to 500 mg (e.g., 30±5, 40±10, 50±10, 75±25, 100±25, 150±25, 200±50, 300±100, or 500±100 mg) per bolus administration.

The invention further features an echinocandin class compound, or a salt thereof, in unit dosage form comprising from 40 to 90% (w/w) non aqueous solvent or aprotic solvent (e.g., ethanol, ethylene glycol, polyethylene glycol (e.g., PEG200, PEG400, PEG800), or propylene glycol) and one or more absorption enhancing excipients described herein. Optionally, the echinocandin class compound is compound 22, or a salt thereof.

The invention further features a method of treating a fungal infection in a subject in need thereof by administering to the subject an intravenous infusion of an aqueous solution including compound 22, or a pharmaceutically acceptable salt thereof, in an amount that is sufficient to treat the fungal infection. In certain embodiments, the infusion solution includes from 0.5 mg/mL to 3.0 mg/mL (e.g., 0.75±0.25, 1.0±0.25, 1.5±0.25, 2.0±0.25, or 2.50±0.50 mg/mL) of compound 22, or a pharmaceutically acceptable salt thereof. In particular embodiments of the method, compound 22, or a pharmaceutically acceptable salt thereof, is administered to the subject in two or more intravenous infusions or intravenous boluses administered once every 5 to 8 days (e.g., weekly for a period of at least 4 weeks, 6 weeks, 8 weeks, or 12 weeks). In another embodiment, the method further includes, following the intravenous infusion, orally administering 200 mg to 1,000 mg (e.g., 250±50, 300±50, 400±50, 500±50, 600±50, 700±50, 800±50, or 900±50 mg) of compound 22, or a pharmaceutically acceptable salt thereof, to the subject daily for a period of at least 5 to 8 days (e.g., daily for a period of at least 2 weeks, 4 weeks, 6 weeks, 8 weeks, or 12 weeks).

The invention features a pharmaceutical composition in unit dosage form including from 25 mL to 500 mL (e.g., 50±25, 100±25, 150±50, 250±50, 350±50, or 400±100 mL) of an aqueous solution including from 0.50 mg/mL to 3 mg/mL (e.g., 0.75±0.25, 1.0±0.25, 1.5±0.25, 2.0±0.25, or 2.50±0.50 mg/mL) compound 22, or a pharmaceutically acceptable salt thereof, wherein the unit dosage form is suitable for intravenous infusion into a subject.

In a related aspect, the invention features a pharmaceutical composition in unit dosage form including from 1 mL to 10 mL (e.g., 1.5±0.5, 3±1, 5±2, or 7.5±2.5 mL) of an aqueous solution including from 25 mg/mL to 500 mg/mL (e.g., 30±5, 40±10, 50±10, 60±10, 70±10, 80±10, 100±15 mg/mL, 130±20 mg/mL, 160±30 mg/mL, 190±30 mg/mL, 250±50 mg/mL or 400±100 mg/mL) compound 22, or a pharmaceutically acceptable salt thereof, wherein the unit dosage form is suitable for intravenous bolus injection into a subject.

In still another related aspect, the invention features a pharmaceutical composition in unit dosage form including from 0.05 mL to 1.0 mL (e.g., 0.2±0.1, 0.5±0.25, 0.75±0.25, or 0.9±0.1 mL) of an aqueous solution including from 85 mg/mL to 300 mg/mL (e.g., 100±15 mg/mL, 130±20 mg/mL, 160±30 mg/mL, 190±30 mg/mL, 250±50 mg/mL or 400±100 mg/mL) compound 22, or a pharmaceutically acceptable salt thereof, wherein the unit dosage form is suitable for subcutaneous injection into a subject.

In any of the above unit dose pharmaceutical compositions formulated for injection, the pharmaceutical composition can (i) be free of stabilizing sugars (e.g., fructose, sucrose, trehalose or combinations thereof), (ii) include a surfactant (e.g., Tween 20, Tween 80, or any surfactant described herein), (iii) a bulking agent (e.g., mannitol, or another sugar alcohol), and/or (iv) a buffer (i.e., any buffer described herein). The aqueous solution in the unit dosage form can be prepared by reconstituting a lyophilized powder including compound 22, or a pharmaceutically acceptable salt thereof. Alternatively, the aqueous solution in the unit dosage form can be prepared by reconstituting a liquid concentrate including compound 22, or a pharmaceutically acceptable salt thereof.

The invention features a kit including (i) a unit dosage form containing a lyophilized powder including compound 22, or pharmaceutically acceptable salt thereof, and (ii) instructions for reconstituting the lyophilized powder with an aqueous solution to form a pharmaceutical composition suitable for injection into a subject.

In a related aspect, the invention features a kit including (i) a unit dosage form containing a liquid concentrate including compound 22, or pharmaceutically acceptable salt thereof, and (ii) instructions for reconstituting the liquid concentrate with an aqueous solution to form a pharmaceutical composition suitable for injection into a subject.

In any of the above kits, the unit dosage form can (i) be free of stabilizing sugars (e.g., fructose, sucrose, trehalose or combinations thereof), (ii) include a surfactant (e.g., Tween 20, Tween 80, or any surfactant described herein), (iii) a bulking agent (e.g., mannitol, or another sugar alcohol), and/or (iv) a buffer (i.e., any buffer described herein).

The invention further features an acid addition salt of an echinocandin class compound in unit dosage form, wherein the acid addition salt is derived from an organic acid (e.g., acetic, lactic, palmoic, maleic, citric, cholic acid, capric acid, caprylic acid, lauric acid, glutaric, glucuronic, glyceric, glycocolic, glyoxylic, isocitric, isovaleric, lactic, malic, oxalo acetic, oxalosuccinic, propionic, pyruvic, ascorbic, succinic, benzoic, palmitic, suberic, salicylic, tartaric, methanesulfonic, toluenesulfonic, or trifluoroacetic acid salts). Optionally, the acid addition salt includes an absorption enhancing agent. Optionally, the echinocandin class compound is an acid addition salt of compound 22. The unit dosage form can further include one or more absorption enhancing excipients described herein.

The invention further features an echinocandin class compound, or a salt thereof, in unit dosage form including from 2 to 80% (w/w) citric acid. The unit dosage form can further include one or more additional absorption enhancing excipients described herein.

The invention also features kits, including: a) any pharmaceutical composition of the invention; and b) instructions for administering the pharmaceutical composition to a subject diagnosed with a fungal infection.

By "acyl carnitine" is meant a chemical moiety with the formula:

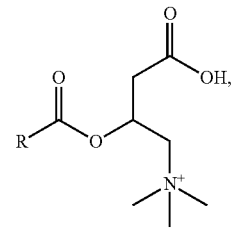

and salts thereof, wherein R is a partially-saturated straight chain or branched hydrocarbon group having between 8 and 26 carbon atoms. Acyl carnitines are derived carnitine (D or L form, or a mixture thereof) and a fatty acid. The acyl carnitine can be an ester of a fatty acid having 16 carbon atoms and 0, 1 or 2 double bonds (C16:0; C16:1 and C16:2), those with 18 carbon atoms and 1, 2 or 3 double bonds (C18:1; C18:2; and C18:3), those with 20 carbon atoms and 1, 2 or 4 double bonds (C20:1; C20:2; and C20:4), or those with 22 carbon atoms and 4, 5 or 6 double bonds (C22:4; C22:5 and C22:6). Acyl carnitines include, without limitation, 4, 7, 10, 13, 16, 19 docosahexanoyl carnitine, oleoyl carnitine, palmitoyl carnitine, decanoyl carnitine, dodecanoyl carnitine, myristoyl carnitine, and stearoyl carnitine.

As used herein, the term "administration" or "administering" refers to administration by any route, such as by injection (e.g., intravenous administration by bolus injection or infusion, subcutaneous administration), transdermal administration, topical administration, intranasal, or peroral administration of a drug to a subject.

By "additive" is meant those components of a pharmaceutical composition containing a drug (e.g., an echinocandin class compound) in oral dosage form which increase the oral bioavailability of the drug when orally administered simultaneously with the drug. Additives of the invention acyl carnitines, alkyl saccharides, ester saccharides, amido fatty acids, ammonium sulfonate surfactants, bile acids and salts (including cholic acid and salts thereof), chitosan and derivatives thereof, fatty acids and salts or esters thereof, glycerides, hydrophilic aromatic alcohols, pegylated phospholipids, peptide epithelial tight junction modulators, phospholipids, polyethylene glycol alkyl ethers, polyglycolized glycerides, polyglycerol fatty acid esters, polysorbate surfactants, carboxylic acids, polyethylene glycols, and mixtures thereof.

By "an amount sufficient" is meant the amount of an additive required to increase the oral bioavailability of a drug.

By "fungal infection" is meant the invasion of a host by pathogenic fungi. For example, the infection may include the excessive growth of fungi that are normally present in or on the body of a human or growth of fungi that are not normally present in or on a human. More generally, a fungal infection can be any situation in which the presence of a fungal population(s) is damaging to a host body. Thus, a human is "suffering" from a fungal infection when an excessive amount of a fungal population is present in or on the person's body, or when the presence of a fungal population(s) is damaging the cells or other tissue of the person.

By "caprylocaproyl polyoxyglyceride" is meant a polyglycolized glyceride that is a mixture of monoesters, diesters, and triesters of glycerol and monoesters and diesters of polyethylene glycols having a mean molecular weight of between 70 and 400, and produced by transesterification of caprylic and capric glyceride esters with polyethylene glycol. Caprylocaproyl polyoxyglycerides include, without limitation, caprylic/capric PEG-8 glyceride (LABRASOL®, Gattefosse), caprylic/capric PEG-4 glyceride (LABRAFAC® Hydro, Gattefosse), and caprylic/capric PEG-6 glyceride (SOFTIGEN®767, Huls).

By "effective" amount is meant the amount of drug required to treat or prevent an infection or a disease associated with an infection. The effective amount of drug used to practice the invention for therapeutic or prophylactic treatment of conditions caused by or contributed to by a microbial infection varies depending upon the manner of administration, the age, body weight, and general health of the subject. Ultimately, the attending physician will decide the appropriate amount and dosage regimen. Such amount is referred to as an "effective" amount.

By "emulsion" is meant a two-phase colloidal system, such as a mixture of two or more immiscible (unblendable) liquids. Liquid emulsions are those in which both the dispersed and the continuous phases are liquid. Energy input through shaking, stirring, homogenizing, or spray processes are typically needed to form an emulsion. For example, the emulsion can include an aqueous phase and a nonaqueous phase, and can include a self emulsifying system, or the emulsion can be nano particulate containing an aqueous phase and a nonaqueous phase (e.g., a nanoemulsion or microemulsion). By "microemulsion" is meant a clear, stable, isotropic liquid mixture of oil, water, and surfactant, optionally in combination with a cosurfactant. The aqueous phase may contain salt(s) and/or other ingredients in addition to a biologically active agent. In contrast to ordinary emulsions, microemulsions form upon simple mixing of the components and do not require the high shear conditions generally used in the formation of ordinary emulsions. The two basic types of microemulsions are direct (oil dispersed in water, o/w) and reversed (water dispersed in oil, w/o).

By "excipient" is meant those components of a pharmaceutical composition containing a drug (e.g., an echinocandin class compound) in oral dosage form which do not increase the oral bioavailability of the drug when orally administered simultaneously with the drug. Excipients which can be used in the formulations of the invention include, without limitation, water, diluents, binders, fillers, and flavorings.

By "fatty acid" is meant an aliphatic carboxylic acid. Fatty acids include, but are not limited to, fatty acids having between 8 and 12 carbon atoms, linear and branched fatty acids, saturated and unsaturated fatty acids, and fatty acids having a hydroxyl group at the termination position of its side chain (i.e., fatty acids bearing a primary hydroxyl group). Exemplary fatty acids are caprylic acid (octanoic acid), pelargonic acid (nonanoic acid), capric acid (decanoic acid), and lauric acid (dodecanoic acid), and their primary hydroxyl forms 8-hydroxy octanoic acid, 9-hydroxy nonanoic acid, 10-hydroxy decanoic acid, and 12-hydroxy dodecanoic acid.

By "hard capsule" is meant a capsule that includes a membrane that forms a two-part, capsule-shaped, container capable of carrying a solid, semi-solid, or liquid payload of drug, additive(s), and, optionally, excipients.

As used herein, by "increase the oral bioavailability" is meant at least 25%, 50%, 75%, 100%, or 300% greater bioavailability of an orally administered drug, as a measured average of AUC in canine subjects (e.g., as described in the examples) for an oral dosage form of the invention including an echinocandin class compound formulated with one or more additives in comparison to the same drug formulated without any additives. For these studies the subjects have gastrointestinal tracts that have not been surgically manipulated in a manner that would alter the oral bioavailability of a drug.

By "liquid dosage form" is meant a solution or suspension from which a dose is measured out (i.e., a teaspoon, tablespoon, or a number of cubic centimeters) for oral administration to a subject.

By "loading-dose regimen" is meant a regimen for the administration of echinocandin class compound that includes at least four administrations of echinocandin class compound in which the dose level administered on Day 1 is at least 120%, 200%, 300%, 400%, or 500% of the dose level administered on any subsequent dosing days, corrected for differences in bioavailability using the formula: dose level=(% BA/100)×dose administered, wherein % BA is percent bioavailability, which for intravenous and subcutaneous dosing is 100. For oral dosing the % BA is determined using method of Example 3. For intransal and other non-injection routes of administration, the percent bioavailability can be determined using analogous methods to those described in Example 3. By "dose level administered on Day 1" is meant the sum total of all echinocandin class compound administered to a subject over the first 24 hours of the initial administration. By "dosing day" is meant a day on which an echinocandin class compound is administered to a subject and the dose administered on a dosing day is the sum total of all echinocandin class compound administered over a 24 hour period beginning from the first administration on this day.

As used herein, "oral bioavailability" refers to the mean fraction of drug absorbed following oral administration to subjects as measured by the blood circulating concentration in comparison to the blood circulating concentration observed for the 100% bioavailability observed with intravenously or intraarterially administered drug. The oral bioavailability can be assessed for a particular formulation can be assessed as provided in Example 3.

By "polyglycolized glyceride" is meant a polyethylene glycol glyceride monoester, a polyethylene glycol glyceride diester, a polyethylene glycol glyceride triester, or a mixture thereof containing a variable amount of free polyethylene glycol, such as a polyethylene glycol-oil transesterification product. The polyglycolized glyceride can include either monodisperse (i.e., single molecular weight) or polydisperse polyethylene glycol moieties of a predetermined size or size range (e.g., PEG2 to PEG 40). Polyethylene glycol glycerides include, for example: PEG glyceryl caprate, PEG glyceryl caprylate, PEG-20 glyceryl laurate (TAGAT® L, Goldschmidt), PEG-30 glyceryl laurate (TAGAT® L2, Goldschmidt), PEG-15 glyceryl laurate (Glycerox L series, Croda), PEG-40 glyceryl laurate (Glycerox L series, Croda), PEG-20 glyceryl stearate (CAPMUL® EMG, ABITEC), and ALDO® MS-20 KFG, Lonza), PEG-20 glyceryl oleate (TAGAT® O, Goldschmidt), and PEG-30 glyceryl oleate (TAGAT® 02, Goldschmidt). Caprylocapryl PEG glycerides include, for example, caprylic/capric PEG-8 glyceride (LABRASOL®, Gattefosse), caprylic/capric PEG-4 glyceride (Labrafac® Hydro, Gattefosse), and caprylic/capric PEG-6 glyceride (SOFTIGEN®767, Huls). Oleoyl PEG glyceride include, for eaxmaple oleoyl PEG-6 glyceride, (Labrafil M1944 CS, Gattefosee). Lauroyl PEG glycerides include, for example, lauroyl PEG-32 glyceride (GELUCIRE® ELUCIRE 44/14, Gattefosse). Stearoyl PEG glycerides include, for example stearoyl PEG-32 glyceride (Gelucrire 50/13, Gelucire 53/10, Gattefosse). PEG castor oils include PEG-3 castor oil (Nikkol CO-3, Nikko), PEG-5, 9, and 16 castor oil (ACCONON CA series, ABITEC), PEG-20 castor oil, (Emalex C-20, Nihon Emulsion), PEG-23 castor oil (Emulgante EL23), PEG-30 castor oil (Incrocas 30, Croda), PEG-35 castor oil (Incrocas-35, Croda), PEG-38 castor oil (Emulgante EL 65, Condea), PEG-40 castor oil (Emalex C-40, Nihon Emulsion), PEG-50 castor oil (Emalex C-50, Nihon Emulsion), PEG-56 castor oil (EUMULGIN® PRT 56, Pulcra SA), PEG-60 castor oil (Nikkol CO-60TX, Nikko), PEG-100 castor oil, PEG-200 castor oil (EUMULGIN® PRT 200, Pulcra SA), PEG-5 hydrogenated castor oil (Nikkol HCO-5, Nikko), PEG-7 hydrogenated castor oil (Cremophor W07, BASF), PEG-10 hydrogenated castor oil (Nikkol HCO-10, Nikko), PEG-20 hydrogenated castor oil (Nikkol HCO-20, Nikko), PEG-25 hydrogenated castor oil (Simulsol® 1292, Seppic), PEG-30 hydrogenated castor oil (Nikkol HCO-30, Nikko), PEG-40 hydrogenated castor oil (Cremophor RH 40, BASF), PEG-45 hydrogenated castor oil (Cerex ELS 450, Auschem Spa), PEG-50 hydrogenated castor oil (Emalex HC-50, Nihon Emulsion), PEG-60 hydrogenated castor oil (Nikkol HCO-60, Nikko), PEG-80 hydrogenated castor oil (Nikkol HCO-80, Nikko), and PEG-100 hydrogenated castor oil (Nikkol HCO-100, Nikko). Additional polyethylene glycol-oil transesterification products include, for example, stearoyl PEG glyceride (GELUCIRE® 50/13, Gattefosse). The polyglycolized glycerides useful in the formulations of the invention can include polyethylene glycol glyceride monoesters, diesters, and/or triesters of acetic, propionic, butyric, valeric, hexanoic, heptanoic, caprylic, nonanoic, capric, lauric, myristic, palmitic, heptadecanoic, stearic, arachidic, behenic, lignoceric, α-linolenic, stearidonic, eicosapentaenoic, docosahexaenoic, linoleic, γ-linolenic, dihomo-γ-linolenic, arachidonic, oleic, elaidic, eicosenoic, erucic, or nervonic acid, or mixtures thereof. The polyglycol moiety in a polyglycolized glyceride can be polydisperse; that is, they can have a variety of molecular weights.

As used herein, the term "salt" refers to any pharmaceutically acceptable salt, such as a non-toxic acid addition salt, metal salt, or metal complex, commonly used in the pharmaceutical industry. Examples of acid addition salts include organic acids, such as acetic, lactic, palmoic, maleic, citric, cholic acid, capric acid, caprylic acid, lauric acid, glutaric, glucuronic, glyceric, glycocolic, glyoxylic, isocitric, isovaleric, lactic, malic, oxalo acetic, oxalosuccinic, propionic, pyruvic, ascorbic, succinic, benzoic, palmitic, suberic, salicylic, tartaric, methanesulfonic, toluenesulfonic, or trifluoroacetic acids, and inorganic acids, such as hydrochloric acid, hydrobromic acid, sulfuric acid, and phosphoric acid. Representative alkali or alkaline earth metal salts include sodium, lithium, potassium, calcium, and magnesium, among others.

By "soft capsule" is meant a capsule molded into a single container carrying a liquid payload of drug, additive(s), and, optionally, excipients.

By "subject" is meant an animal, e.g., a human, pet (e.g., dog or cat), farm animal (e.g., goat, cow, horse, sheep, or pig), and/or a mammal.

As used herein, the term "treating" refers to administering a pharmaceutical composition for prophylactic and/or therapeutic purposes. To "prevent disease" refers to prophylactic treatment of a subject who is not yet ill, but who is susceptible to, or otherwise at risk of, a particular disease. To "treat disease" or use for "therapeutic treatment" refers to administering treatment to a subject already suffering from a disease to improve or stabilize the subject's condition. Thus, in the claims and embodiments, treating is the administration to a subject either for therapeutic or prophylactic purposes.

The term "unit dosage form" refers to physically discrete units suitable as unitary dosages, such as a tablet, caplet, hard capsule, soft capsule, or sachet, each unit containing a predetermined quantity of drug.

In the generic descriptions of certain compounds, the number of atoms of a particular type in a substituent group may be given as a range, e.g., an alkyl group containing from 5 to 8 carbon atoms or $C_{5-8}$ alkyl. Reference to such a range is intended to include specific references to groups having each of the integer number of atoms within the specified range. For example, an alkyl group from 5 to 8 carbon atoms includes each of $C_5$, $C_6$, $C_7$, and $C_8$. A $C_{5-8}$ heteroalkyl, for example, includes from 5 to 8 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups. The $C_{1-8}$ alkyl group may be substituted or unsubstituted. Exemplary substituents include alkoxy, aryloxy, sulfhydryl, alkylthio, arylthio, halide, hydroxyl, fluoroalkyl, perfluoroalkyl, cyano, nitrilo, NH-acyl, amino, aminoalkyl, disubstituted amino, quaternary amino, hydroxyalkyl, carboxyalkyl, and carboxyl groups.

By "$C_{2-10}$ heterocyclyl" is meant a stable 3- to 7-membered monocyclic or 7- to 14-membered bicyclic heterocyclic ring which is saturated partially unsaturated or unsaturated (aromatic), and which consists of 2 to 10 carbon atoms and 1, 2, 3 or 4 heteroatoms independently selected from the group consisting of N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoroalkyl, cyano, nitrilo, NH-acyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another.

By "$C_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary substituents are alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "$C_{7-16}$ alkaryl" is meant an alkyl substituted by an aryl group (e.g., benzyl, phenethyl, or 3,4-dichlorophenethyl) having from 7 to 16 carbon atoms.

By "$C_{3-10}$ alkheterocyclyl" is meant an alkyl substituted heterocyclic group having from 3 to 10 carbon atoms in addition to one or more heteroatoms (e.g., 3-furanylmethyl, 2-furanylmethyl, 3-tetrahydrofuranylmethyl, or 2-tetrahydrofuranylmethyl).

Other features and advantages of the invention will be apparent from the following detailed description, the drawings, and the claims.

DETAILED DESCRIPTION

Figure 1:
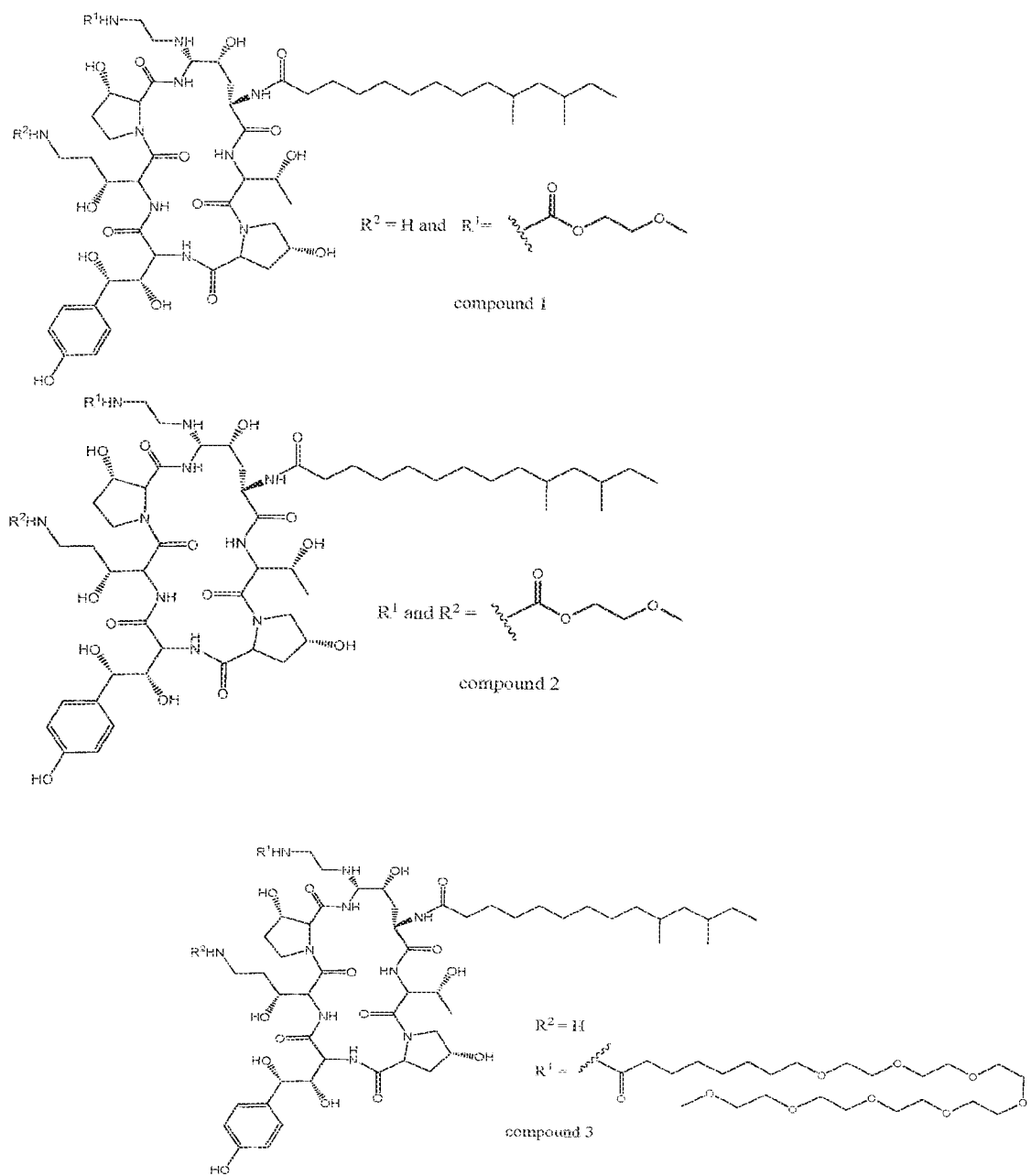
FIGS. 1-14 depict compounds of the invention.
Figure 2:
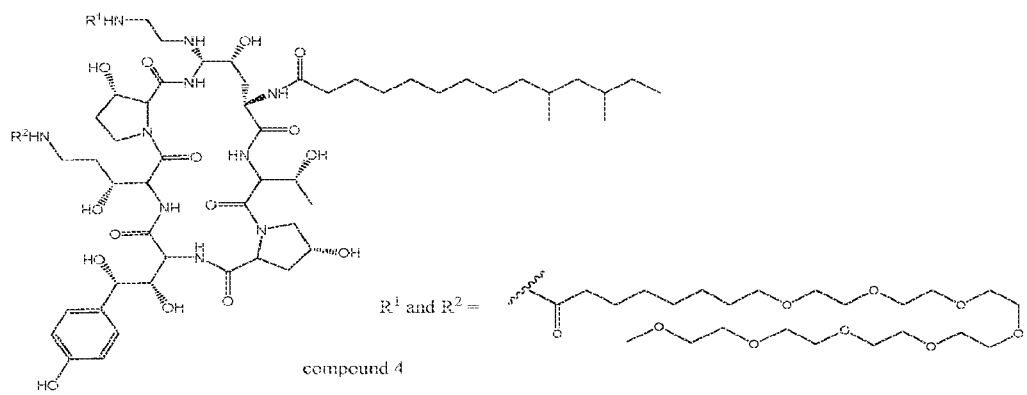
Figure 2:
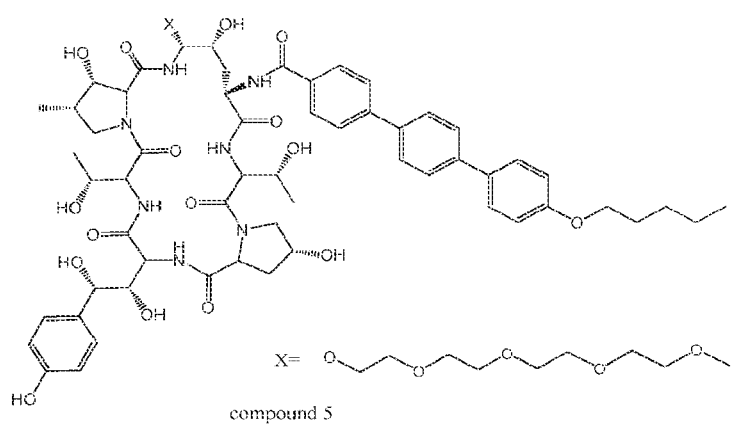
Figure 2:
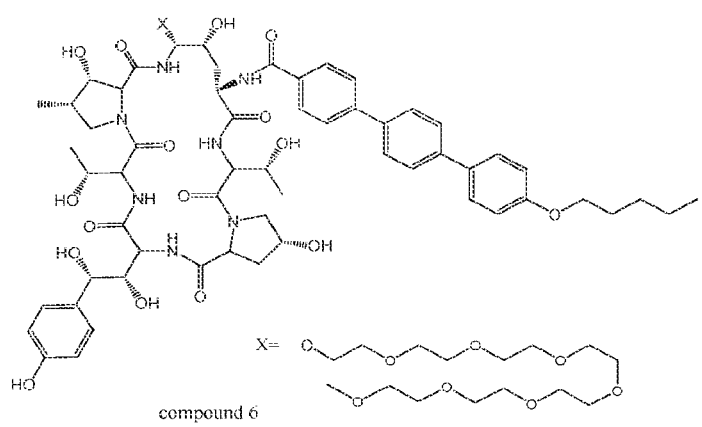
Figure 3:
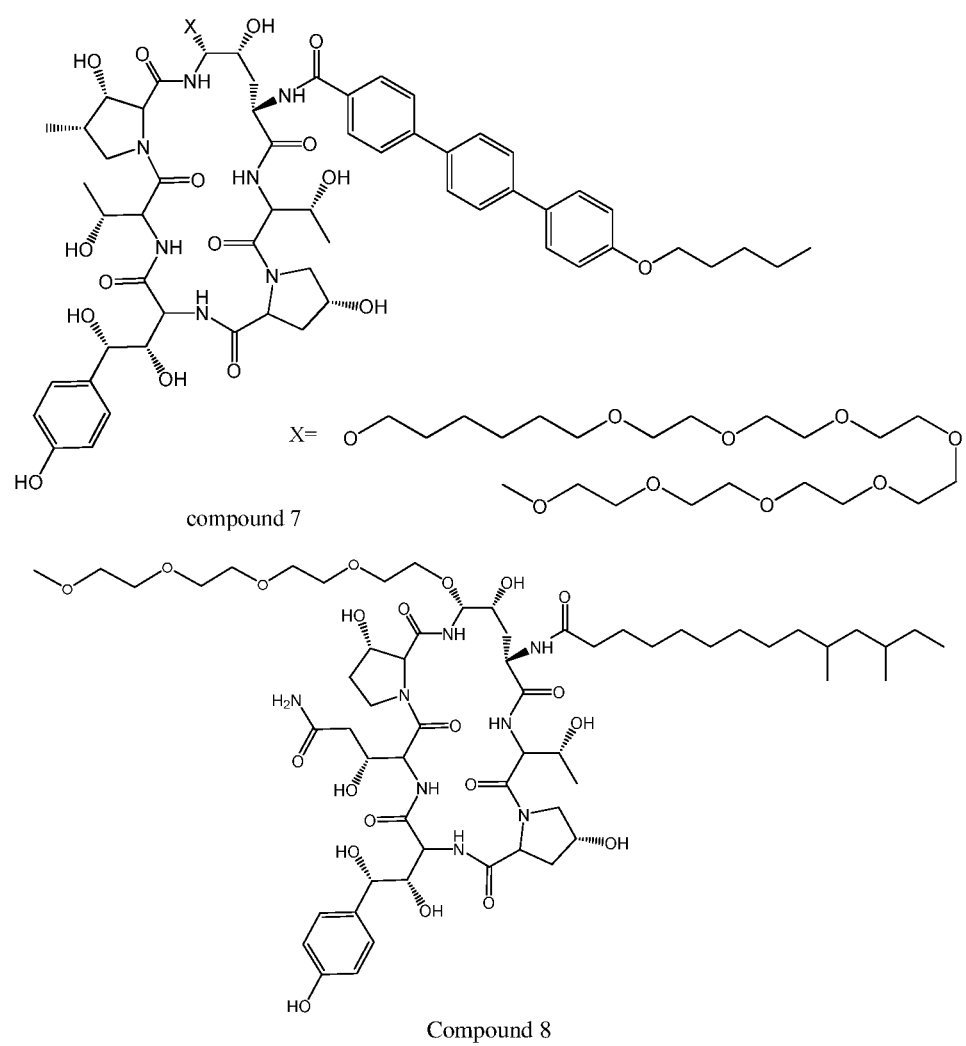
Figure 4:
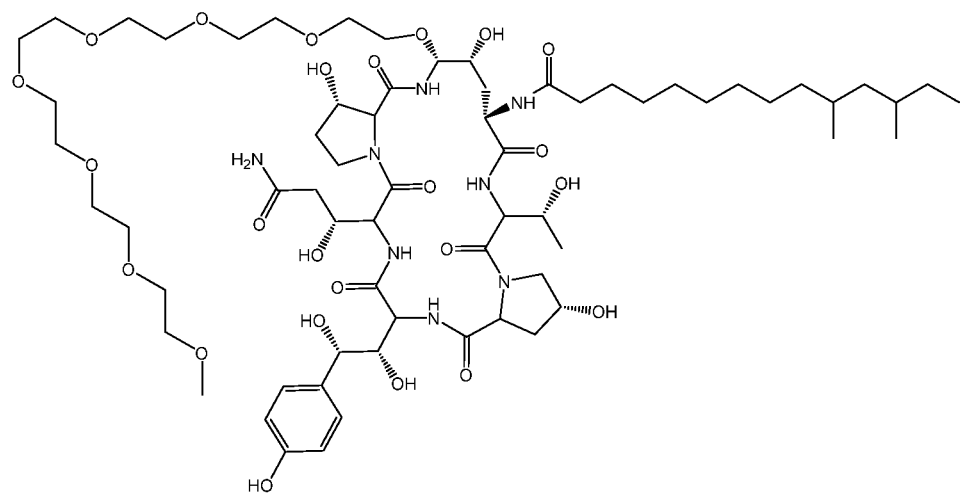
Figure 4:
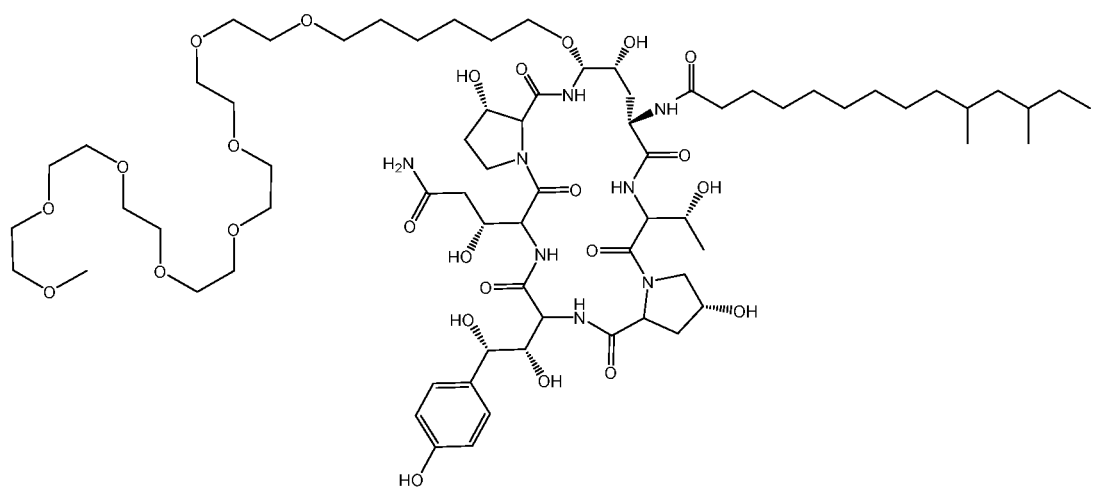
Figure 5:
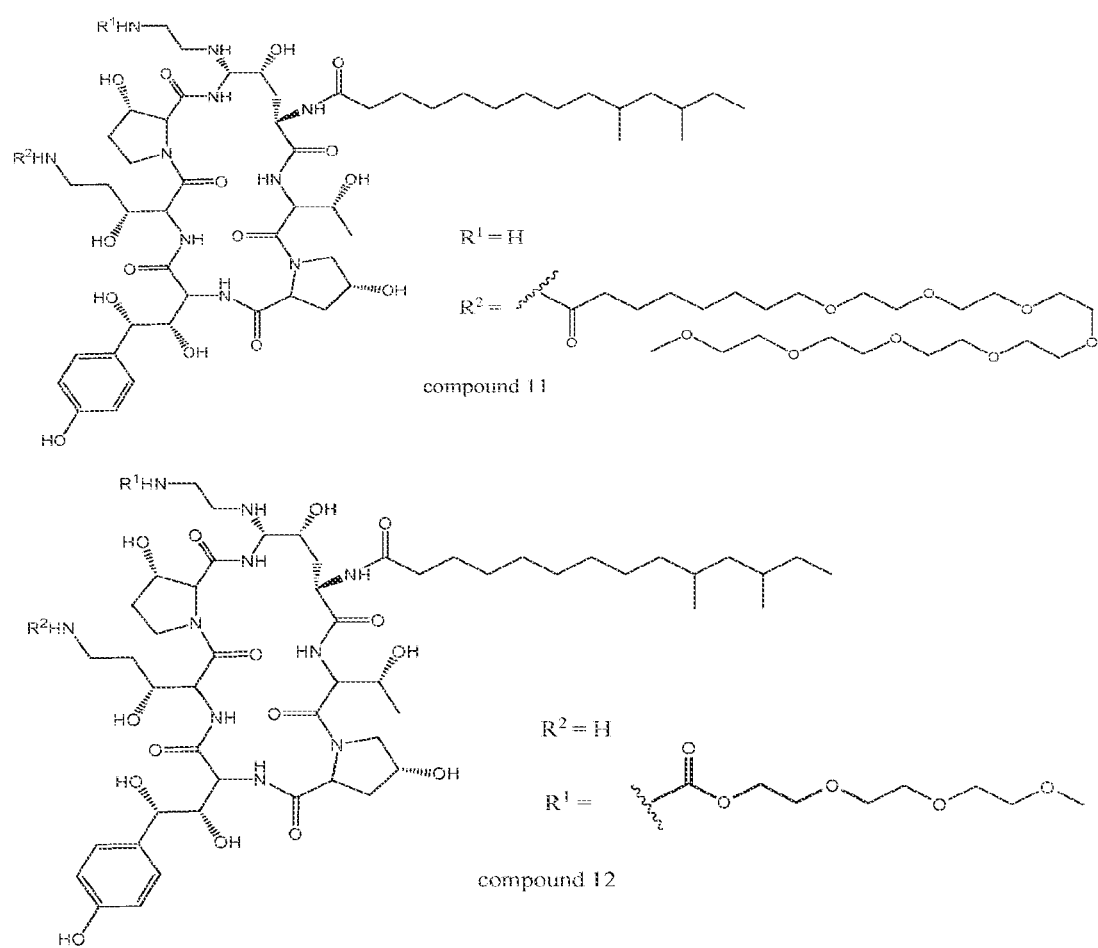
Figure 6:
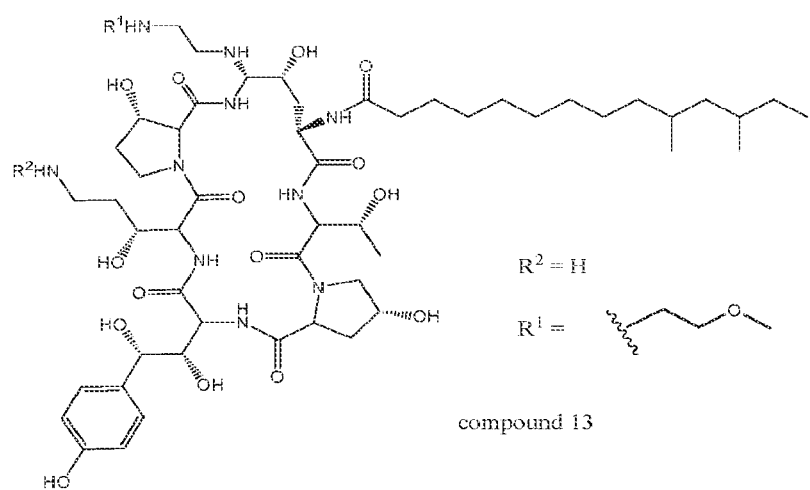
Figure 6:
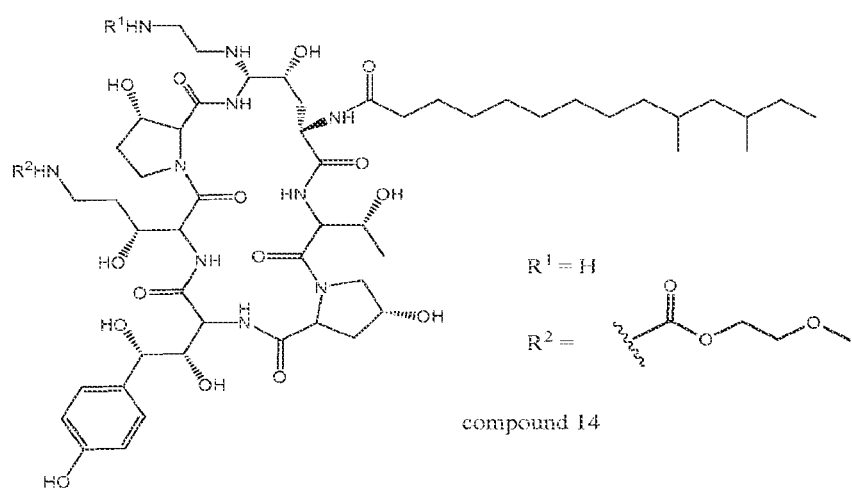
Figure 7:
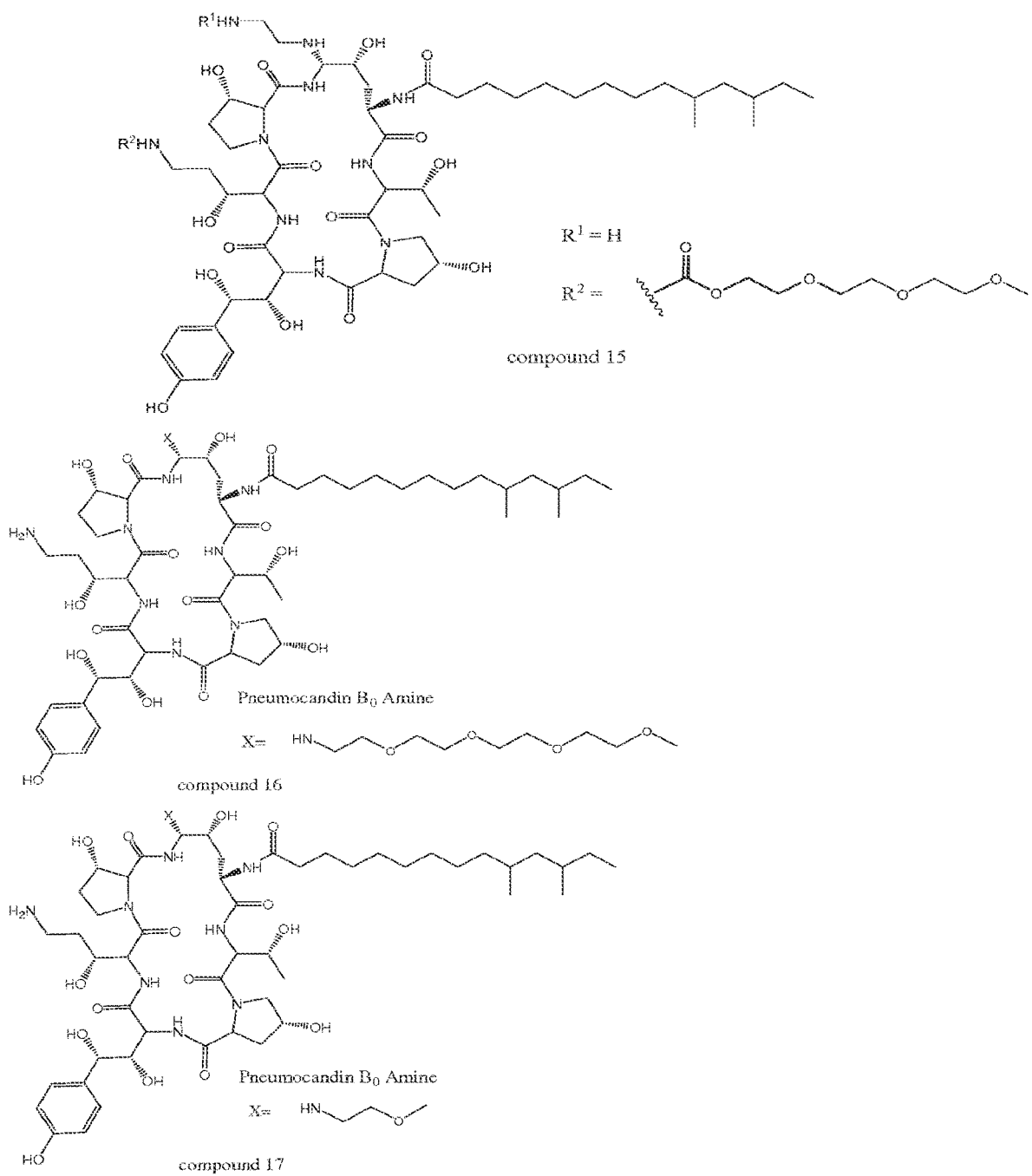
Figure 8:
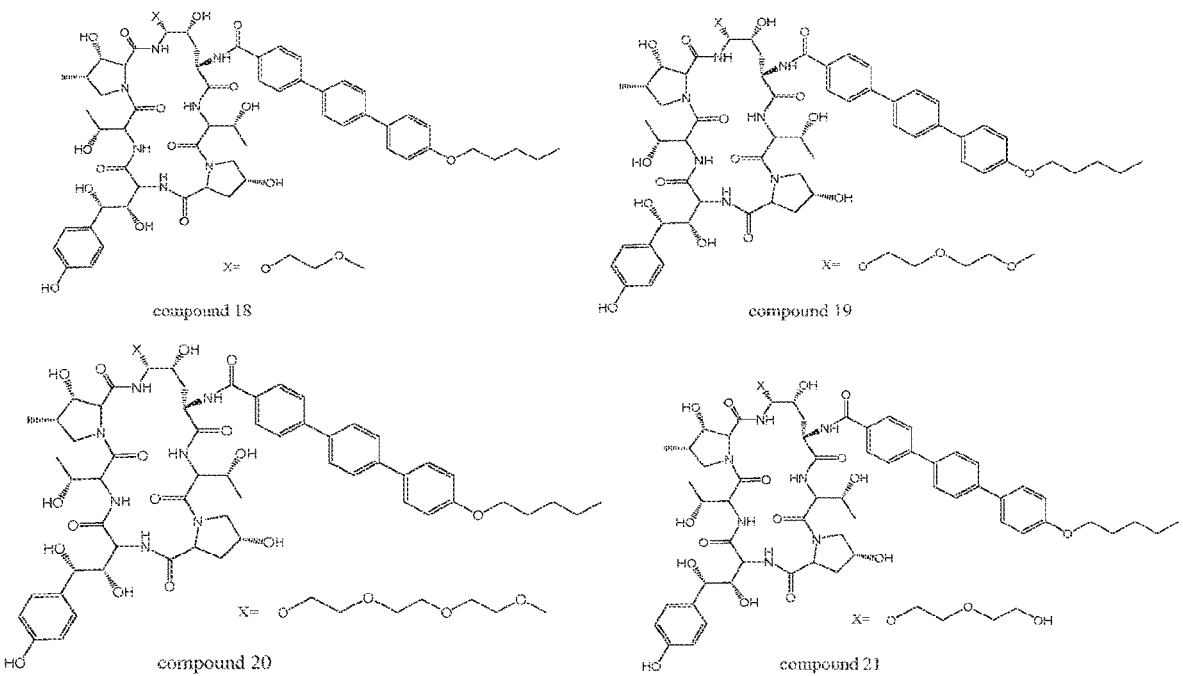
Figure 9:
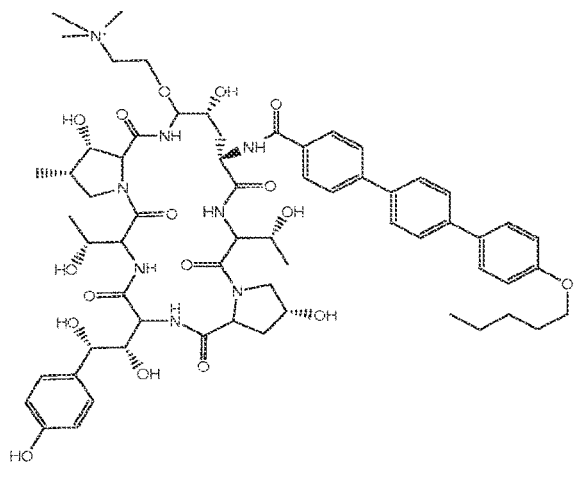
Figure 9:
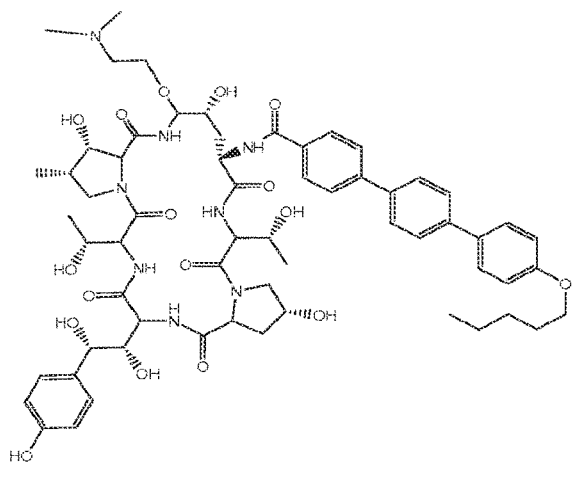
Figure 9:
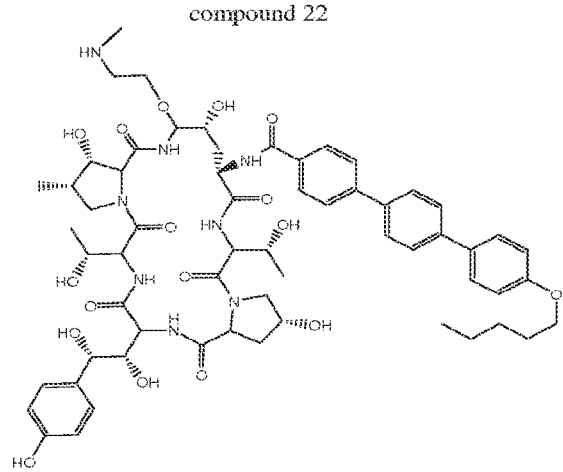
Figure 9:
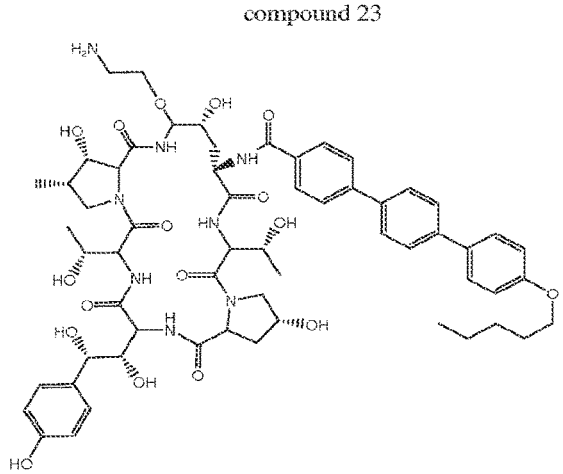
Figure 10:
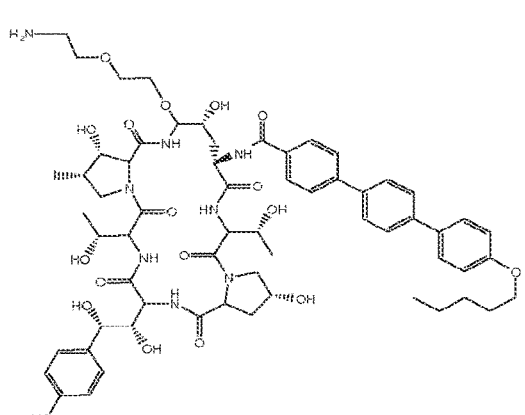
Figure 10:
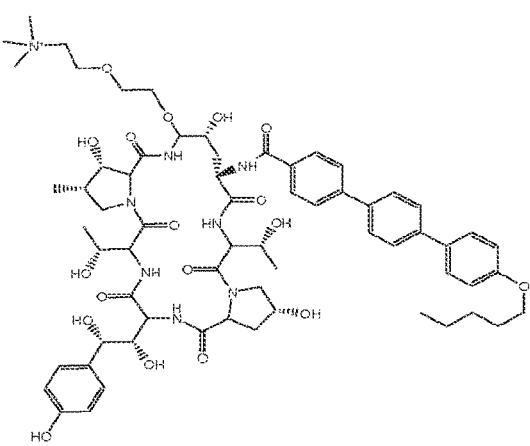
Figure 10:
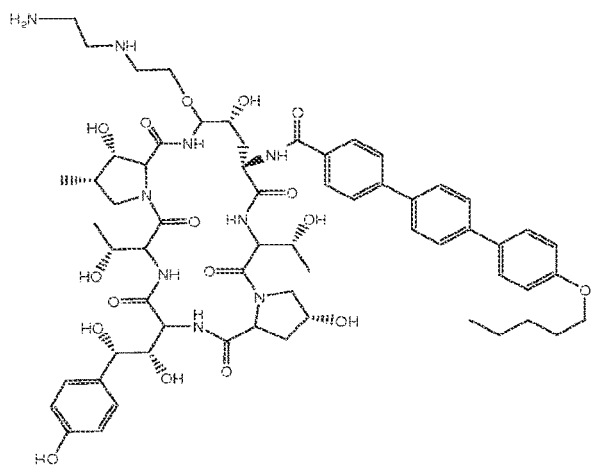
Figure 10:
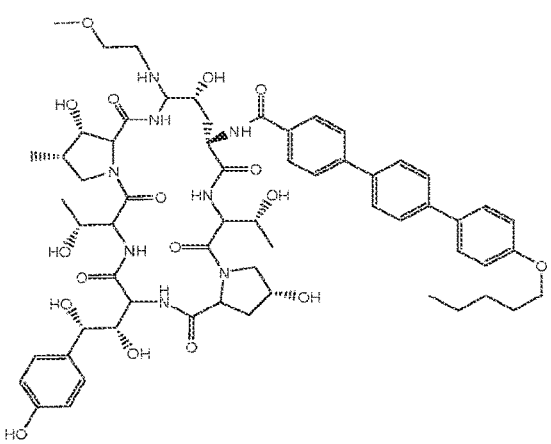
Figure 11:
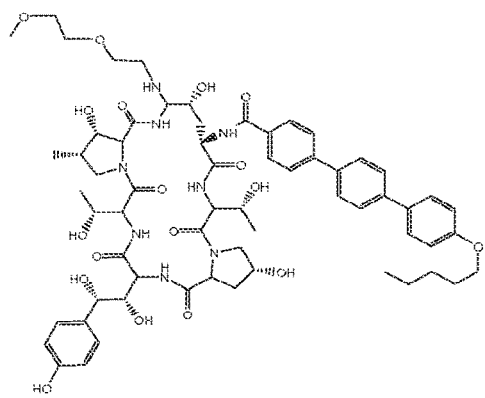
Figure 11:
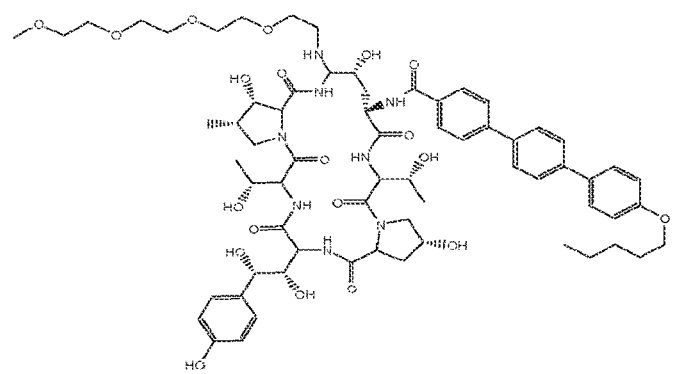
Figure 11:
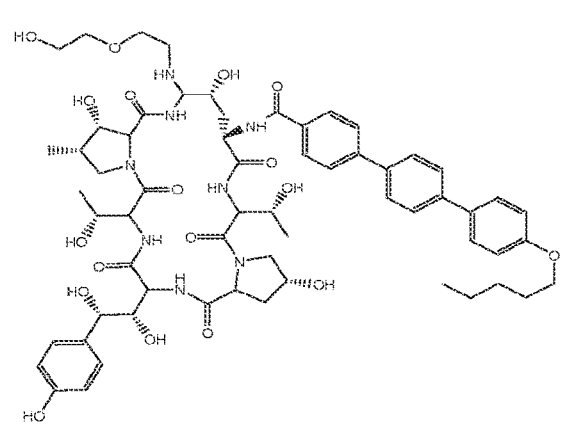
Figure 11:
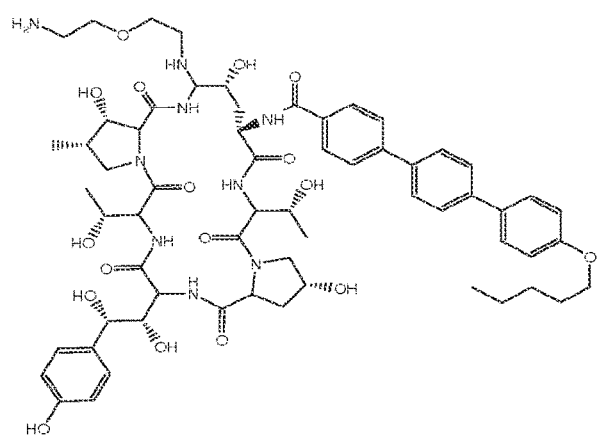
Figure 12:
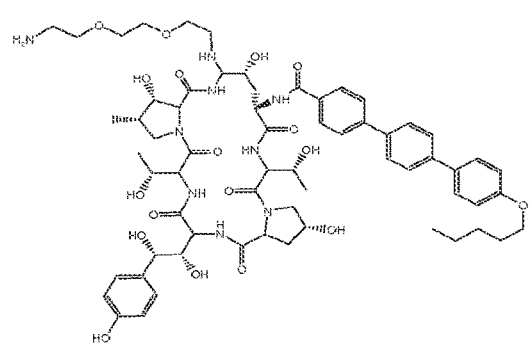
Figure 12:
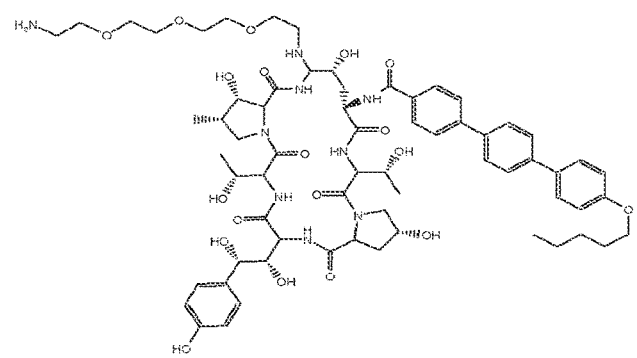
Figure 12:
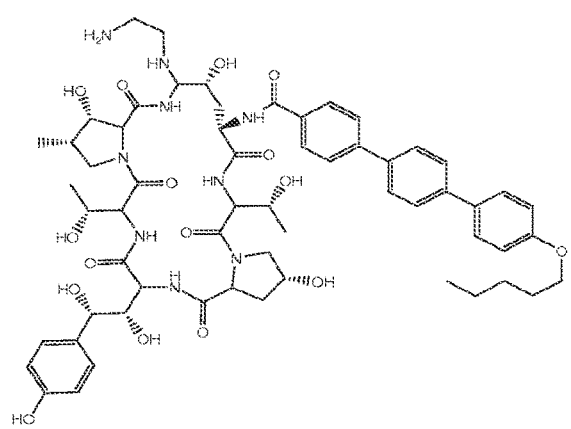
Figure 12:
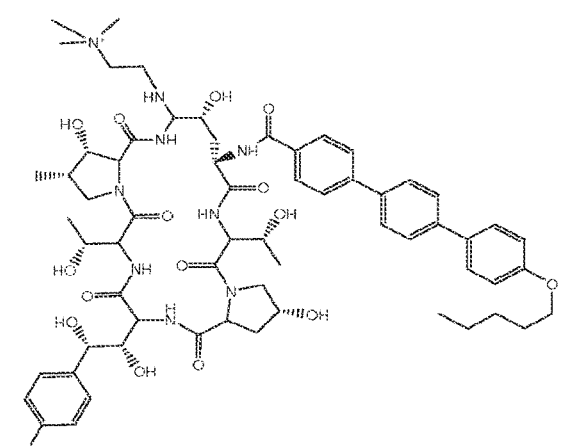
Figure 13:
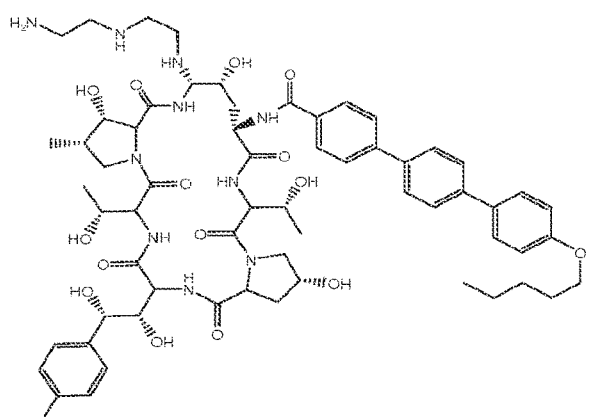
Figure 13:
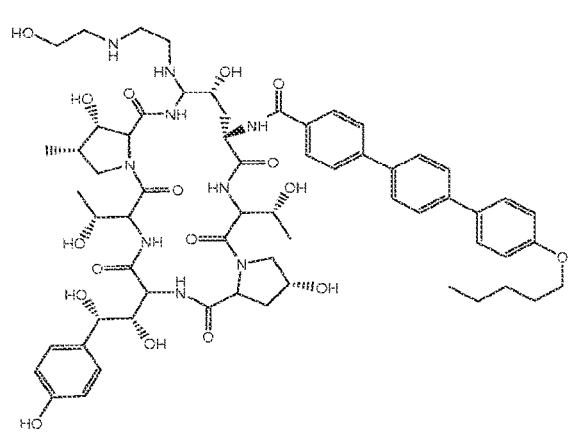
Figure 13:
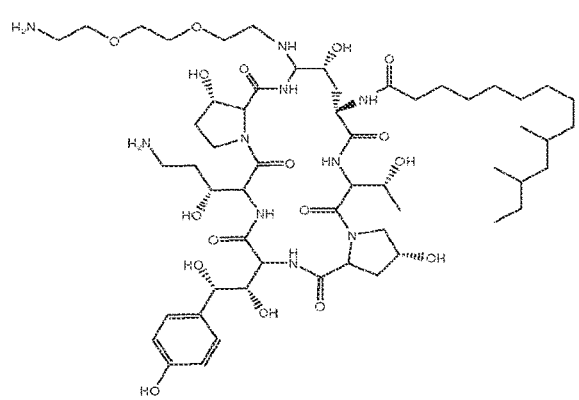
Figure 13:
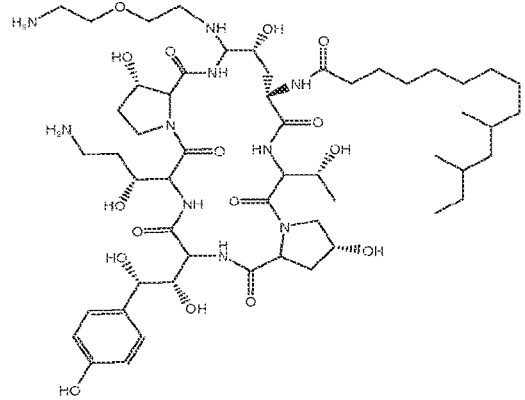
Figure 14:
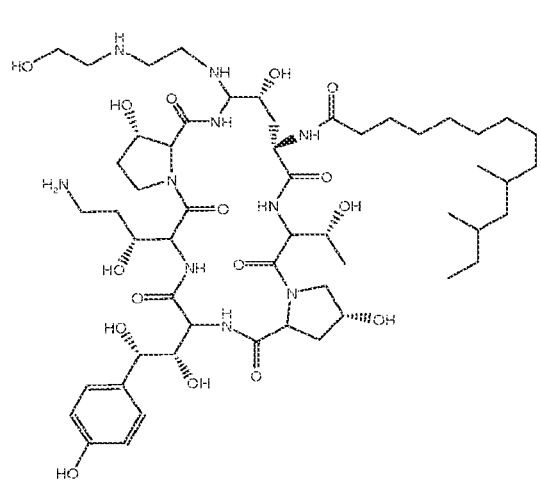
Figure 14:
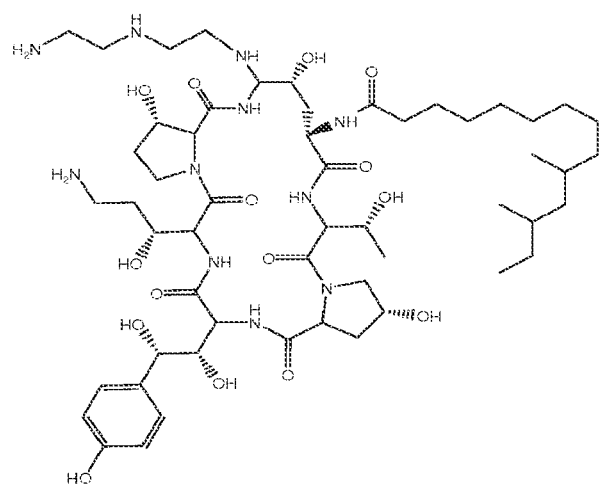
Figure 14:
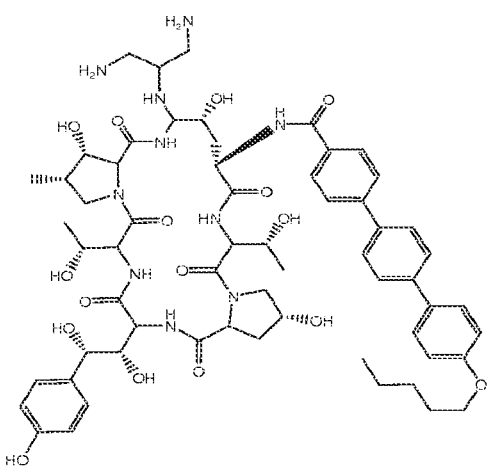
Figure 14:
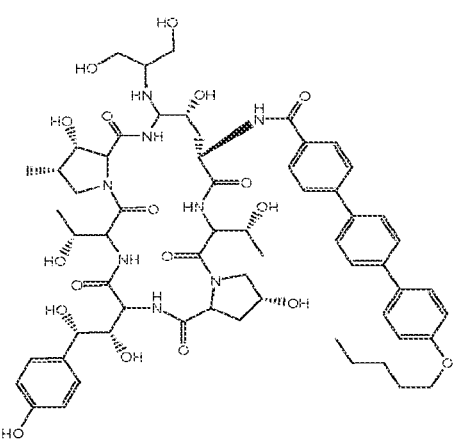
Figure 14:
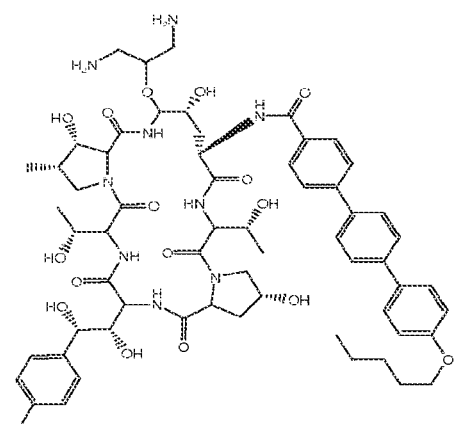
Figure 15A:
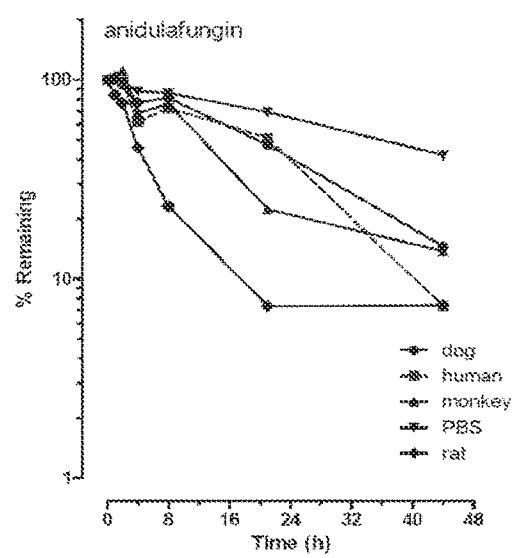
FIGS. 15A and 15B are graphs depicting the stability of compound 22 and anidulafungin in various mammalian plasmas and phosphate buffered saline as described in Example 7. Compound 22 is more stable than anidulafungin in all of the matrices tested.
Figure 15B:
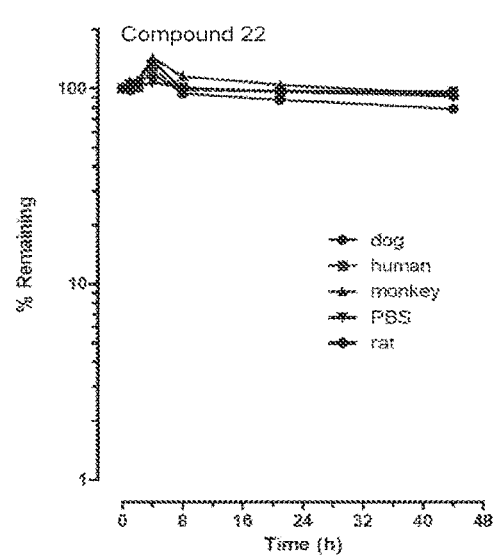

The invention features dosing regimens and pharmaceutical formulations for oral administration including a drug (e.g., an echinocandin class compound) formulated with a permeation enhancer. The formulations are useful for increasing the oral bioavailability of the drug. The invention also features dosing regimens for echinocandin class compounds, in particular compound 22, wherein the dosing frequency is reduced and/or the regimen permits self-administration (i.e., subcutaneous or oral administration), such that the regimen can be performed at least in part outside a hospital setting.

Echinocandin Class Compounds

The formulations of the invention can be used to increase the oral bioavailability of echinocandin class compounds. Echinocandin class compounds are inhibitors of the synthesis of 1,3-β-D-glucan and include an antibiotic cyclic lipohexapeptide having the backbone depicted in formula (I).

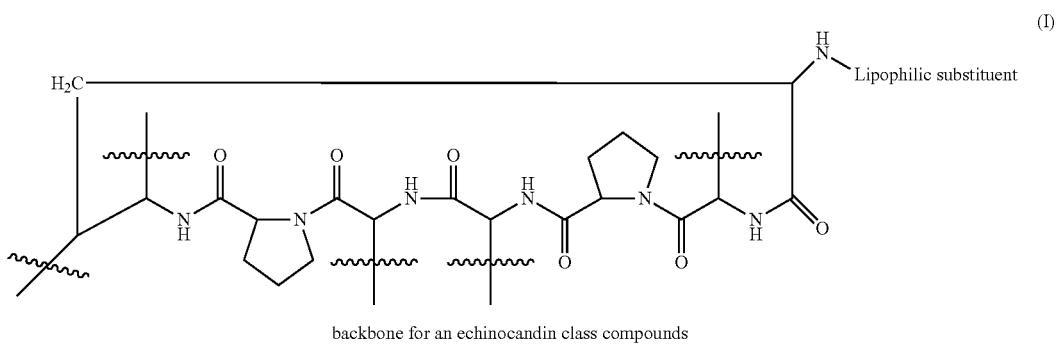

backbone for an echinocandin class compounds

Echinocandin class compounds include, without limitation, caspofungin, echinocandin B, anidulafungin, pneumocandin $B_0$, aculeacin $A_\gamma$, micafungin, and their derivatives.

Echinocandin class compounds can be synthesized, for example, by coupling functionalized or unfunctionalized echinocandin class compounds with the appropriate acyl, alkyl, hydroxyl, and/or amino groups under standard reaction conditions (see PCT Publication No. WO 2011/025875, and U.S. provisional Ser. No. 61/448,807, herein incorporated by reference). Typically, the semi-synthetic echinocandin class compounds are made by modifying the naturally occurring echinocandin scaffold. For example, pneumocandin $B_0$ is prepared by fermentation reactions; where fermentation and mixed broths produce a mixture of products which are then separated to produce pneumocandin $B_0$, which is used in the synthesis of caspofungin (see U.S. Pat. No. 6,610,822, which describes extractions of the echinocandin class compounds, such as, pneumocandin $B_0$, WF 11899 and echinocandin B by performing several extraction processes; and see U.S. Pat. No. 6,610,822, which describes methods for purifying the crude extracts). For semi-synthetic approaches to echinocandin class compounds of the invention, the stereochemistry of the compound will be dictated by the starting material. Thus, the stereochemistry of the unnatural echinocandin derivatives will typically have the same stereochemistry as the naturally occurring echinocandin scaffold from which they are derived. Accordingly, any of echinocandin B, anidulafungin, micafungin, and caspofungin, can be used as a starting material in the synthesis of echinocandin class compounds which share the same stereochemical configuration at each of the amino acid residues found in the naturally occurring compound.

The echinocandin class compound can be selected from those described in PCT Publication No. WO 2011/025875, and U.S. provisional Ser. No. 61/448,807, filed Mar. 3, 2011, each of are incorporated herein by reference.

The echinocandin class compound administered and/or formulated as described herein can be a compound of formula (II):

In formula (II), $R^1$ is $NHCH_2CH_2NBR^{A1}$, $NHCH_2CH_2NR^{A1}R^{A2}$, $NHCH_2CH_2NHC(O)R^{A1}$, $CH_2NHR^{A1}$, $CH_2NR^{A1}R^{A2}$, $CH_2NHC(O)R^{A1}$, or $OR^{A1}$; $R^2$ is H, $CH_3$, $CH_2CH_2NHR^{B1}$, $CH_2CH_2NR^{B1}R^{B2}$, $CH_2CH_2NHC(O)R^{B1}$, $CH_2C(O)NHR^{B1}$, $CH_2CH_2CH(OR^{B1})NHR^{B2}$, $CH_2CH_2CH(OR^{B1})NR^{B2}R^{B3}$, or $CH_2CH_2CH(OR^{B1})NHC(O)R^{B2}$; $R^3$ is H or $CH_3$; $R^4$ is H, $OSO_3H$, $CH_2NHR^{C1}$, $CH_2NR^{C1}R^{C2}$, $CH_2NHC(O)R^{C1}$; $R^5$ is a lipophilic group selected from: PEG; C(O)-PEG; PEG-alkyl; C(O)-PEG-alkyl; PEG-aryl; C(O)-PEG-aryl; PEG-alkaryl; C(O)-PEG-alkaryl; alkyl-PEG; C(O)-alkyl-PEG; aryl-PEG; C(O)-aryl-PEG; alkaryl-PEG; C(O)-alkaryl-PEG;

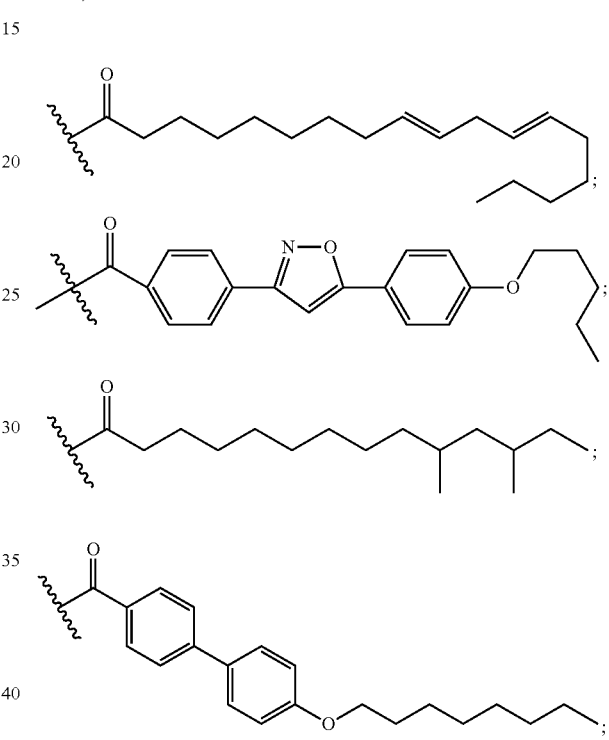

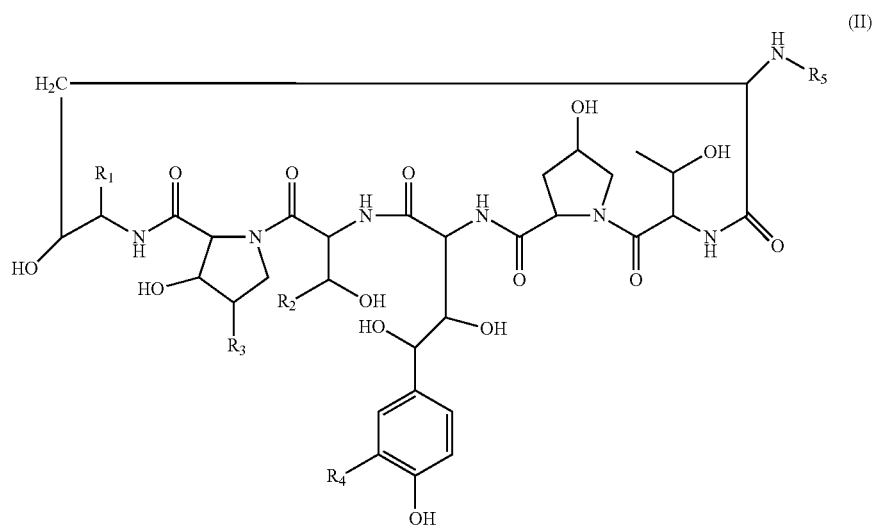

-continued

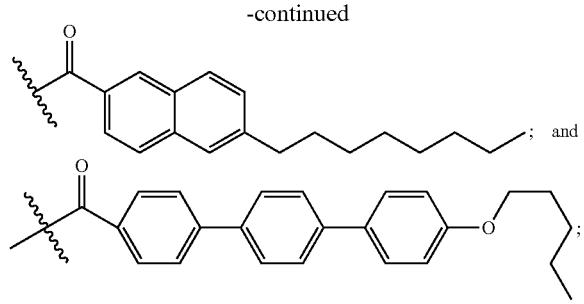

and each of $R^{A1}$, $R^{A2}$, $R^{B1}$, $R^{B2}$, $R^{B3}$, $R^{C1}$, and $R^{C2}$ is, independently, selected from H, $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, heteroalkyl, PEG, alkyl-PEG, aryl-PEG, alkaryl-PEG, PEG-alkyl, PEG-aryl, and PEG-alkaryl, and pharmaceutically acceptable salts thereof, provided that the echinocandin class compound includes at least one PEG, alkyl-PEG, aryl-PEG, alkaryl-PEG, PEG-alkyl, PEG-aryl, or PEG-alkaryl group. In particular embodiments of the echinocandin class compound of formula (II), $R^4$ is selected from: (i) —CH$_2$NH—(CH$_2$CH$_2$O)$_m$—(CH$_2$)$_n$-Me, (ii) —CH$_2$NH—(CH$_2$)$_q$—O—(CH$_2$CH$_2$O)$_m$-Me, (iii) —CH$_2$NH—(CH$_2$)$_p$—NH—(CO)—(CH$_2$)$_s$—O—(CH$_2$CH$_2$O)$_m$-Me, and (iv) —CH$_2$NHCH[(CH$_2$O(CH$_2$CH$_2$O)$_s$-Me)(CH$_2$O(CH$_2$CH$_2$O)$_t$-Me)], wherein n is an integer from 0 to 11 (e.g., 0 to 7, 1 to 7, 2 to 7, 3 to 9, or 4 to 11), q is an integer from 3 to 12 (e.g., 3 to 7, 5 to 9, or 7 to 12), p is an integer from 2 to 8 (e.g., 2 to 4, 3 to 6, or 4 to 8), s is an integer from 0 to 5 (e.g., 0, 1, 2, 3, 4, or 5), t is an integer from 0 to 5 (e.g., 0, 1, 2, 3, 4, or 5), and m is an integer from 1 to 10 (e.g., 1 to 7, 1 to 5, 2 to 7, 2 to 5, or 3 to 7). In still other embodiments of the echinocandin class compound of formula (II), $R^5$ is selected from: (i) —(CH$_2$CH$_2$O)$_m$—(CH$_2$)$_n$-Me, (ii) —C(O)—(CH$_2$CH$_2$O)$_m$—(CH$_2$)$_n$-Me, (iii) —C(O)CH$_2$—O—(CH$_2$CH$_2$O)$_m$—(CH$_2$)$_n$-Me, and (iv) —C(O)—O—(CH$_2$CH$_2$O)$_m$—(CH$_2$)$_n$-Me, wherein n is an integer from 0 to 11 (e.g., 0 to 7, 1 to 7, 2 to 7, 3 to 9, or 4 to 11), and m is an integer from 1 to 10 (e.g., 1 to 7, 1 to 5, 2 to 7, 2 to 5, or 3 to 7).

The echinocandin class compound administered and/or formulated as described herein can be a compound of formula (III):

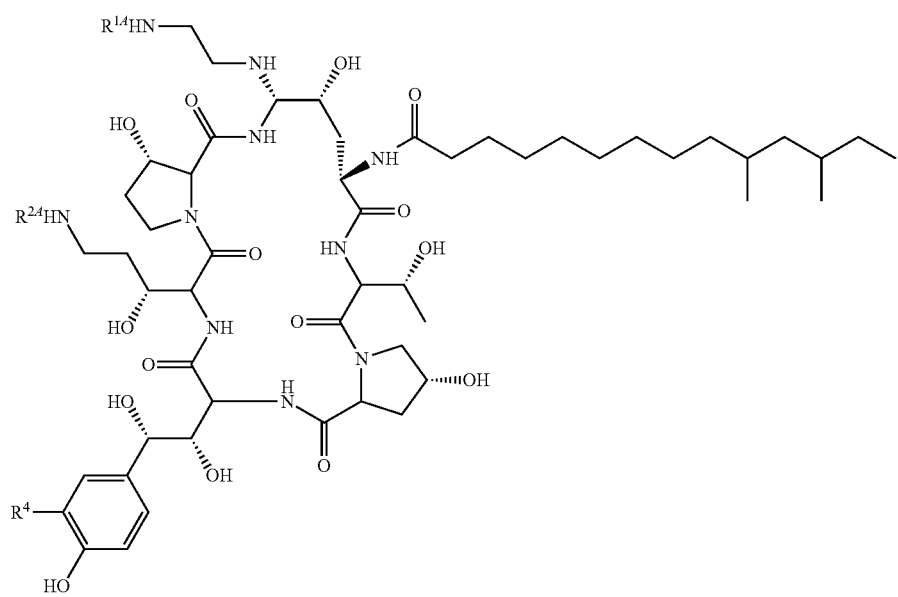

In formula (III), $R^{14}$ is H, $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, $C_{1-10}$ heteroalkyl, PEG, alkyl-PEG, aryl-PEG, alkaryl-PEG, PEG-alkyl, PEG-aryl, or PEG-alkaryl; $R^{2A}$ is H, $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, $C_{1-10}$ heteroalkyl, PEG, alkyl-PEG, aryl-PEG, alkaryl-PEG, PEG-alkyl, PEG-aryl, or PEG-alkaryl; $R^4$ is H, $OSO_3H$, $CH_2NHR^{ci}$, $CH_2NR^{C1}R^{C2}$, $CH_2NHC(O)R^{C1}$; and each of $R^{C1}$ and $R^{C2}$ is, independently, selected from H, $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, $C_{1-10}$ heteroalkyl, PEG, alkyl-PEG, aryl-PEG, alkaryl-PEG, PEG-alkyl, PEG-aryl, and PEG-alkaryl, and pharmaceutically acceptable salts thereof, provided that the echinocandin class compound includes at least one PEG, alkyl-PEG, aryl-PEG, alkaryl-PEG, PEG-alkyl, PEG-aryl, or PEG-alkaryl. In certain embodiments of the echinocandin class compound of formula (III), one of $R^{1A}$, $R^{2A}$, IC and $R^{C2}$ is selected from: (i) —$(CH_2)_p$—O—$(CH_2CH_2O)_m$-Me, and (ii) —$(CH_2CH_2O)_m$-Me, and (iii) —C(O)(CH_2), —$(OCH_2CH_2)_m$—OMe, wherein n is an integer from 0 to 11 (e.g., 0 to 7, 1 to 7, 2 to 7, 3 to 9, or 4 to 11), p is an integer from 3 to 12 (e.g., 3 to 8, 4 to 10, or 6 to 12), and m is an integer from 1 to 10 (e.g., 1 to 7, 1 to 5, 2 to 7, 2 to 5, or 3 to 7). In particular embodiments of the echinocandin class compound of formula (II), $R^{1A}$ is H and $R^{2A}$ is PEG, alkyl-PEG, aryl-PEG, alkaryl-PEG, PEG-alkyl, PEG-aryl, or PEG-alkaryl; $R^{1A}$ is PEG, alkyl-PEG, aryl-PEG, alkaryl-PEG, PEG-alkyl, PEG-aryl, or PEG-alkaryl and $R^{2A}$ is H; or each of $R^{1A}$ and $R^{2A}$ is, independently, selected from PEG, alkyl-PEG, aryl-PEG, alkaryl-PEG, PEG-alkyl, PEG-aryl, and PEG-alkaryl.

The echinocandin class compound administered and/or formulated as described herein can be a compound of formula (IV):

In formula (IV), $R^1$ is $NHCH_2CH_2NHR^{A1}$, $NHCH_2CH_2NR^{A1}R^{A2}$, $NHCH_2CH_2NHC(O)R^{A1}$, $CH_2NHR^{A1}$, $CH_2NR^{A1}R^{A2}$, $CH_2NHC(O)R^{A1}$, or $OR^{A1}$; $R^4$ is H, $OSO_3H$, $CH_2NHR^{C1}$, $CH_2NR^{C1}R^{C2}$, $CH_2NHC(O)R^{C1}$; and each of $R^{A1}$, $R^{A2}$, $R^{C1}$, and $R^{C2}$ is, independently, selected from H, $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, $C_{1-10}$ heteroalkyl, PEG, alkyl-PEG, aryl-PEG, alkaryl-PEG, PEG-alkyl, PEG-aryl, and PEG-alkaryl, and pharmaceutically acceptable salts thereof, provided that the echinocandin class compound includes at least one PEG, alkyl-PEG, aryl-PEG, alkaryl-PEG, PEG-alkyl, PEG-aryl, or PEG-alkaryl group. In certain embodiments of the echinocandin class compound of formula (IV), $R^1$ is selected from: (i) —O—$(CH_2CH_2O)_m$—$(CH_2)_n$-Me, (ii) —NH—$(CH_2CH_2O)_m$—$(CH_2)_n$-Me, (iii) —O—$(CH_2)_q$—O—$(CH_2CH_2O)_m$-Me, (iv) —NH—$(CH_2)_q$—O—$(CH_2CH_2O)_m$-Me, (v) —O—$(CH_2)_p$—NH—(CO)—$(CH_2)$, —O—$(CH_2CH_2O)_m$-Me, (vi) —NH—$(CH_2)_p$—NH—(CO)—$(CH_2)_n$—O—$(CH_2CH_2O)_m$-Me, (vii) —NHCH[$(CH_2O(CH_2CH_2O)_s$-Me)$(CH_2O(CH_2CH_2O)_t$-Me)], and (viii) —O—CH[$(CH_2O(CH_2CH_2O)_n$-Me)$(CH_2O(CH_2CH_2O)_t$-Me)], wherein n is an integer from 0 to 11 (e.g., 0 to 7, 1 to 7, 2 to 7, 3 to 9, or 4 to 11), q is an integer from 3 to 12 (e.g., 3 to 7, 5 to 9, or 7 to 12), p is an integer from 2 to 8 (e.g., 2 to 4, 3 to 6, or 4 to 8), s is an integer from 0 to 5 (e.g., 0, 1, 2, 3, 4, or 5), t is an integer from 0 to 5 (e.g., 0, 1, 2, 3, 4, or 5), and m is an integer from 1 to 10 (e.g., 1 to 7, 1 to 5, 2 to 7, 2 to 5, or 3 to 7).

The echinocandin class compound administered and/or formulated as described herein can be a compound of formula (V):

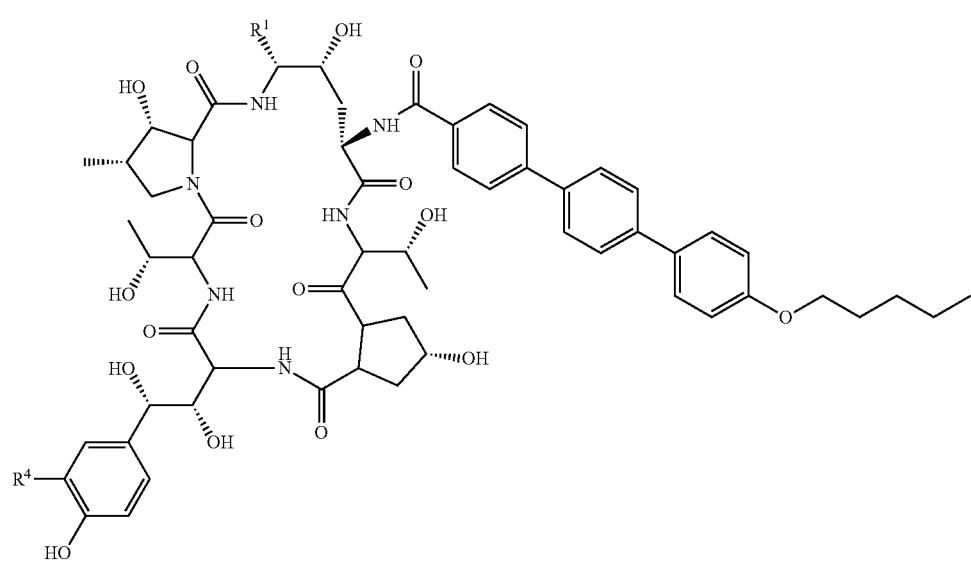

(IV)

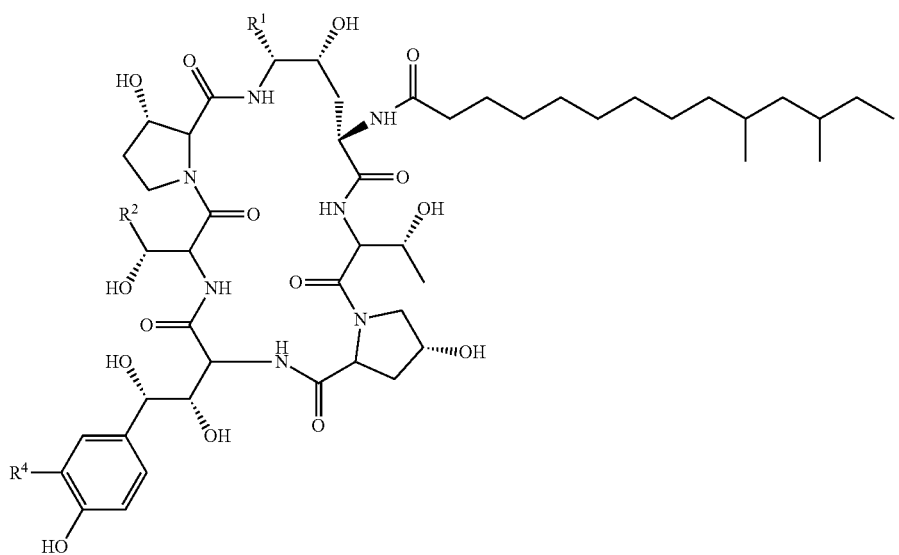

(V)

In formula (V), $R^1$ is $NHCH_2CH_2NHR^{A1}$, $NHCH_2CH_2NR^{A1}R^{A2}$, $NHCH_2CH_2NHC(O)R^{A1}$, $CH_2NHR^{A1}$, $CH_2NR^{A1}R^{A2}$, $CH_2NHC(O)R^{A1}$, or $OR^{A1}$; $R^2$ is H, $CH_3$, $CH_2CH_2NHR^{B1}$, $CH_2CH_2NR^{B1}R^{B2}$, $CH_2CH_2NHC(O)R^{B1}$, $CH_2C(O)NHR^{B1}$, $CH_2CH_2CH(OR^{B1})NHR^{B2}$, $CH_2CH_2CH(OR^{B1})NR^{B2}R^{B3}$, or $CH_2CH_2CH(OR^{B1})NHC(O)R^{B2}$; $R^4$ is H, $OSO_3H$, $CH_2NHR^{C1}$, $CH_2NR^{C1}R^{C2}$, $CH_2NHC(O)R^{C1}$; and each of $R^{A1}$, $R^{A2}$, $R^{B1}$, $R^{B2}$, $R^{B3}$, $R^{C1}$, and $R^{C2}$ is, independently, selected from H, $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, heteroalkyl, PEG, alkyl-PEG, aryl-PEG, alkaryl-PEG, PEG-alkyl, PEG-aryl, and PEG-alkaryl, and pharmaceutically acceptable salts thereof, provided that the echinocandin class compound includes at least one PEG, alkyl-PEG, aryl-PEG, alkaryl-PEG, PEG-alkyl, PEG-aryl, or PEG-alkaryl group. In certain embodiments of the echinocandin class compound of formula (V), $R^1$ is selected from: (i) —O—$(CH_2CH_2O)_m$—$(CH_2)_n$-Me, (ii) —NH—$(CH_2CH_2O)_m$—$(CH_2)_n$-Me, (iii) —O—$(CH_2)_q$—O—$(CH_2CH_2O)_m$-Me, (iv) —NH—$(CH_2)_q$—O—$(CH_2CH_2O)_m$-Me, (v) —O—$(CH_2)_p$—NH—(CO)—$(CH_2)_n$—O—$(CH_2CH_2O)_m$-Me, (vi) —NH—$(CH_2)_p$—NH—(CO)—$(CH_2)_n$—O—$(CH_2CH_2O)_m$-Me, (vii) —NHCH[$(CH_2O(CH_2CH_2O)_s$-Me)$(CH_2O(CH_2CH_2O)_t$-Me)], and (viii) —O—CH[$(CH_2O(CH_2CH_2O)_s$-Me)$(CH_2O(CH_2CH_2O)_t$-Me)], wherein n is an integer from 0 to 11 (e.g., 0 to 7, 1 to 7, 2 to 7, 3 to 9, or 4 to 11), q is an integer from 3 to 12 (e.g., 3 to 7, 5 to 9, or 7 to 12), p is an integer from 2 to 8 (e.g., 2 to 4, 3 to 6, or 4 to 8), s is an integer from 0 to 5 (e.g., 0, 1, 2, 3, 4, or 5), t is an integer from 0 to 5 (e.g., 0, 1, 2, 3, 4, or 5), and m is an integer from 1 to 10 (e.g., 1 to 7, 1 to 5, 2 to 7, 2 to 5, or 3 to 7).

The echinocandin class compound administered and/or formulated as described herein can be a compound of formula (VI):

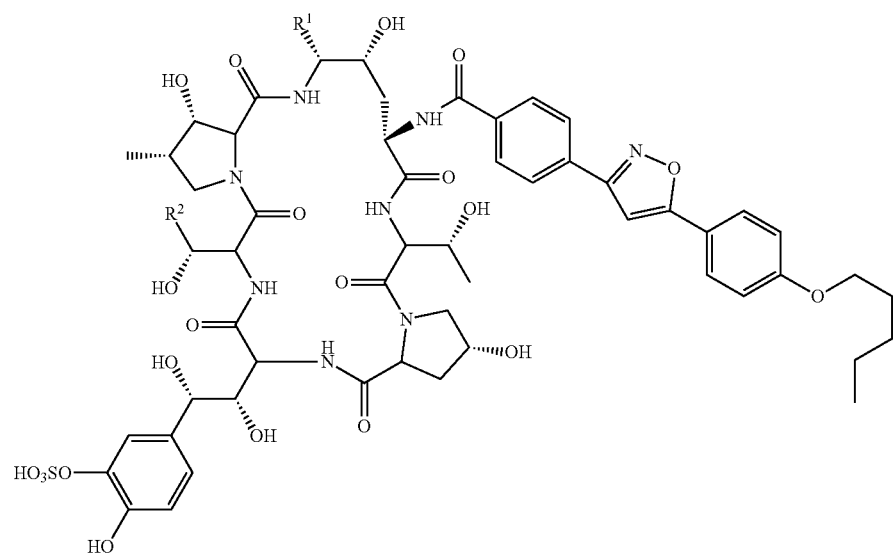

(VI)

In formula (VI), $R^1$ is $NHCH_2CH_2NBR^{A1}$, $NHCH_2CH_2NR^{A1}R^{A2}$, $NHCH_2CH_2NHC(O)R^{A1}$, $CH_2NHR^{A1}$, $CH_2NR^{A1}R^{A2}$, $CH_2NHC(O)R^{A1}$, or $OR^{A1}$; $R^2$ is H, $CH_3$, $CH_2CH_2NHR^{B1}$, $CH_2CH_2NR^{B1}R^{B2}$, $CH_2CH_2NHC(O)R^{B1}$, $CH_2C(O)NHR^{B1}$, $CH_2CH_2CH(OR^{B1})NHR^{B2}$, $CH_2CH_2CH(OR^{B1})NR^{B2}R^{B3}$, or $CH_2CH_2CH(OR^{B1})NHC(O)R^{B2}$; and each of $R^{A1}$, $R^{A2}$, $R^{B1}$, $R^{B2}$, and $R^{B3}$ is, independently, selected from H, $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, heteroalkyl, PEG, alkyl-PEG, aryl-PEG, alkaryl-PEG, PEG-alkyl, PEG-aryl, and PEG-alkaryl, and pharmaceutically acceptable salts thereof, provided that the echinocandin class compound includes at least one PEG, alkyl-PEG, aryl-PEG, alkaryl-PEG, PEG-alkyl, PEG-aryl, or PEG-alkaryl group. In certain embodiments of the echinocandin class compound of formula (VI), $R^1$ is selected from: (i) $-O-(CH_2CH_2O)_m-(CH_2)_n-Me$, (ii) $-NH-(CH_2CH_2O)_m-(CH_2)_n-Me$, (iii) $-O-(CH_2)_q-O-(CH_2CH_2O)_m-Me$, (iv) $-NH-(CH_2)_q-O-(CH_2CH_2O)_m-Me$, (v) $-O-(CH_2)_p-NH-(CO)-(CH_2)_n-O-(CH_2CH_2O)_m-Me$, (vi) $-NH-(CH_2)_p-NH-(CO)-(CH_2)_n-O-(CH_2CH_2O)_m-Me$, (vii) $-NHCH[(CH_2O(CH_2CH_2O)_s-Me)(CH_2O(CH_2CH_2O)_t-Me)]$, and (viii) $-O-CH[(CH_2O(CH_2CH_2O)_s-Me)(CH_2O(CH_2CH_2O)_t-Me)]$, wherein n is an integer from 0 to 11 (e.g., 0 to 7, 1 to 7, 2 to 7, 3 to 9, or 4 to 11), q is an integer from 3 to 12 (e.g., 3 to 7, 5 to 9, or 7 to 12), p is an integer from 2 to 8 (e.g., 2 to 4, 3 to 6, or 4 to 8), s is an integer from 0 to 5 (e.g., 0, 1, 2, 3, 4, or 5), t is an integer from 0 to 5 (e.g., 0, 1, 2, 3, 4, or 5), and m is an integer from 1 to 10 (e.g., 1 to 7, 1 to 5, 2 to 7, 2 to 5, or 3 to 7).

The echinocandin class compound administered and/or formulated as described herein can be a compound of formula (VII):

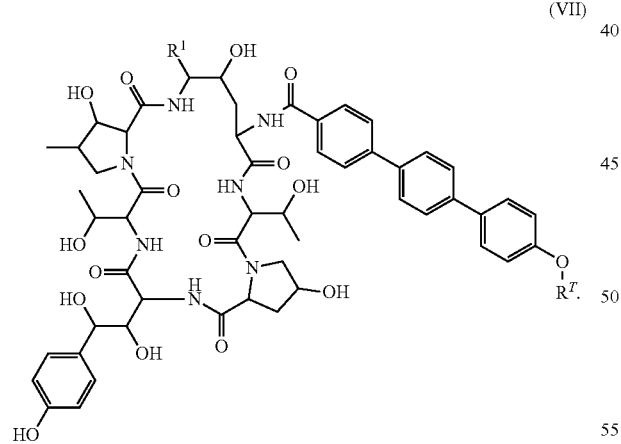

(VII)

In formula (VII), $R^1$ is $O(CH_2CH_2O)_nCH_2CH_2X_1$, $O(CH_2CH_2CH_2O)_nCH_2CH_2X_1$, $NHCH_2CH_2X_2$, $NH(CH_2CH_2O)_mCH_2CH_2X_2$, $NH(CH_2CH_2CH_2O)_mCH_2CH_2X_2$, $NH(CH_2CH_2O)_pCH_2CH_2X_3$, $NH(CH_2CH_2CH_2O)_pCH_2CH_2X_3$, $NHCH_2CH_2X_4$, $NH[CH_2(CH_2)_aO]_bCH\{CH_2[OCH_2(CH_2)_c]_dX_5\}_2$, $O[CH_2(CH_2)_aO]_bCH\{CH_2[OCH_2(CH_2)_c]_dX_5\}_2$, $NH(CH_2CH_2M)_rCH_2CH_2X_5$, $NHCH_2(CH_2)_qX_6$, or $OCH_2(CH_2)_qX_6$; $R^T$ is n-pentyl, sec-pentyl, or iso-pentyl; $X_1$ is $NH_2$, $NHR^{A1}$, $NR^{A1}R^{A2}$, $NR^{A1}R^{A2}R^{A3}$, or $NHCH_2(CH_2)_vZ_1$; $X_2$ is OH, $OR^{B1}$, or $OCH_2(CH_2)_vZ_1$; $X_3$ is $NH_2$, $NHR^{C1}$, $NR^{C1}R^{C2}$, or $NR^{C1}R^{C2}R^{C3}$, or $NHCH_2(CH_2)_vZ_1$; $X_4$ is $NR^{B1}R^{D2}R^{D3}$ or $NHCH_2(CH_2)_vZ_1$; each $X_5$ is, independently, selected from OH, $OR^{E1}$, $NH_2$, $NHR^{E1}$, $NR^{E1}R^{E2}$, $NR^{E1}R^{E2}R^{E3}$, $OCH_2(CH_2)_vZ_1$, and $NHCH_2(CH_2)_vZ_1$; $X_6$ is selected from $NR^{F1}R^{F2}R^{F3}$ or $Z_1$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); n is an integer from 1 to 5 (e.g., 1, 2, 3, 4, or 5); m is an integer from 1 to 5 (e.g., 1, 2, 3, 4, or 5); p is an integer from 1 to 5 (e.g., 1, 2, 3, 4, or 5); r is an integer from 1 to 5 (e.g., 1, 2, 3, 4, or 5); q is an integer from 1 to 3 (e.g., 1, 2, or 3); v is an integer from 1 to 3 (e.g., 1, 2, or 3); each of $R^{A1}$, $R^{A2}$, $R^{A3}$, $R^{B1}$, $R^{C1}$, $R^{C2}$, $R^{C3}$, $R^{D1}$, $R^{D2}$, $R^{D3}$, $R^{E1}$, $R^{E2}$, $R^{E3}$, $R^{F1}$, $R^{F2}$, and $R^{F3}$ is, independently, selected from $CH_3$, $CH_2CH_3$, $CH_2CH_2CH_3$, and $CH(CH_3)_2$; $Z_1$ is selected from:

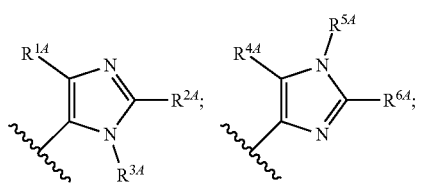

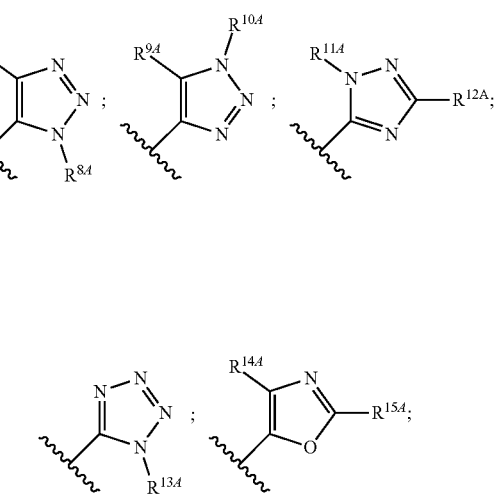

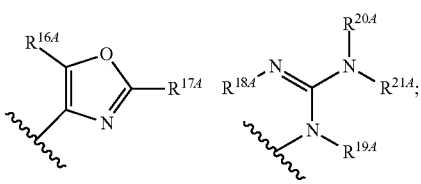

-continued

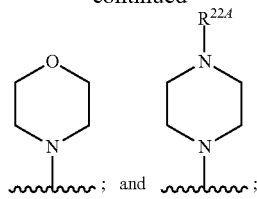
; and and each of 10, $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, and $R^{22A}$ is, independently, selected from H, $CH_3$, $CH_2CH_3$, $CH_2CH_2CH_3$, and $CH(CH_3)_2$, or a pharmaceutically acceptable salt thereof.

In certain embodiments, the compound of formula (VII) is further described by formula (VIIa):

(VIIa)

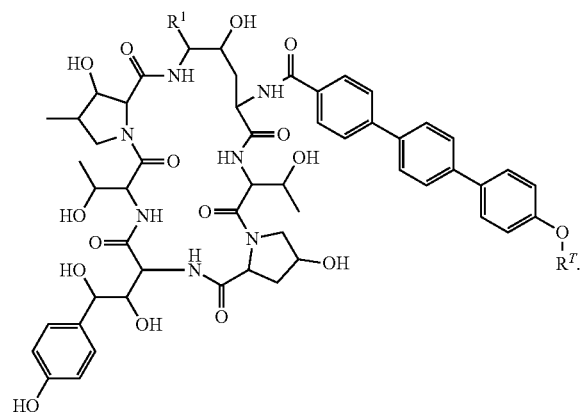

In formula (VIIa), $R^1$ is $O(CH_2CH_2O)_nCH_2CH_2X_1$, $O(CH_2CH_2CH_2O)_nCH_2CH_2X_1$, $NHCH_2CH_2X_2$, $NH(CH_2CH_2O)_mCH_2CH_2X_2$, $NH(CH_2CH_2CH_2O)_mCH_2CH_2X_2$, $NH(CH_2CH_2O)_pCH_2CH_2X_3$, $NH(CH_2CH_2CH_2O)_pCH_2CH_2X_3$, $NHCH_2CH_2X_4$, $NH[CH_2(CH_2)_aO]_bCH\{CH_2[OCH_2(CH_2)_c]_dX_5\}_2$, $O[CH_2(CH_2)_aC]_bCH\{CH_2[OCH_2(CH_2)_c]_dX_5\}_2$, $NH(CH_2CH_2NH)_rCH_2CH_2X_5$, $NHCH_2(CH_2)_qX_6$, or $OCH_2(CH_2)_qX_6$; $R^T$ is n-pentyl, sec-pentyl, or iso-pentyl; $X_1$ is $NH_2$, $NHR^{A1}$, $NR^{A1}R^{A2}$, or $NR^{A1}R^{A2}R^{A3}$; $X_2$ is OH or $OR^{B1}$; $X_3$ is $NH_2$, $NHR^{C1}$, $NR^{C1}R^{C2}$, or $NR^{C1}R^{C2}R^{C3}$; $X_4$ is $NR^{D1}R^{D2}R^{D3}$; each $X_5$ is, independently, selected from OH, $OR^{E1}$, $NH_2$, $NHR^{E1}$, $NR^{E1}R^{E2}$, and $NR^{E1}R^{E2}R^{E3}$; $X_6$ is selected from $NR^{F1}R^{F2}R^{F3}$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); n is an integer from 1 to 5 (e.g., 1, 2, 3, 4, or 5); m is an integer from 1 to 5 (e.g., 1, 2, 3, 4, or 5); p is an integer from 1 to 5 (e.g., 1, 2, 3, 4, or 5); r is an integer from 1 to 5 (e.g., 1, 2, 3, 4, or 5); q is an integer from 1 to 3 (e.g., 1, 2, or 3); and each of $R^{A1}$, $R^{A2}$, $R^{A3}$, $R^{B1}$, $R^{C1}$, $R^{C2}$, $R^{C3}$, $R^{D1}$, $R^{D2}$, $R^{D3}$, $R^{E1}$, $R^{E2}$, $R^{E3}$, $R^{F1}$, $R^{F2}$, and $R^{F3}$ is, independently, selected from $CH_3$, $CH_2CH_3$, $CH_2CH_2CH_3$, and $CH(CH_3)_2$, or a pharmaceutically acceptable salt thereof. In particular embodiments of the compounds of formula (I) and (Ia), one of $X_1$, $X_3$, $X_4$, and $X_5$ is selected from $N(CH_3)_3^+$ and $N(CH_2CH_3)_3^+$. In certain embodiments of the compounds of formula (I) and (Ia), $R^1$ is $NHCH[CH_2CH_2N(CH_3)_3^+]_2$, $NHCH_2CH_2OCH[CH_2CH_2N(CH_3)_3^+]_2$, or $NHCH_2CH_2OCH[CH_2CH_2N(CH_3)_3^+][CH_2CH_2OCH_2CH_2OH]$.

In still other embodiments, the compound of formula (VII) is further described by formula (VIIb):

(VIIb)

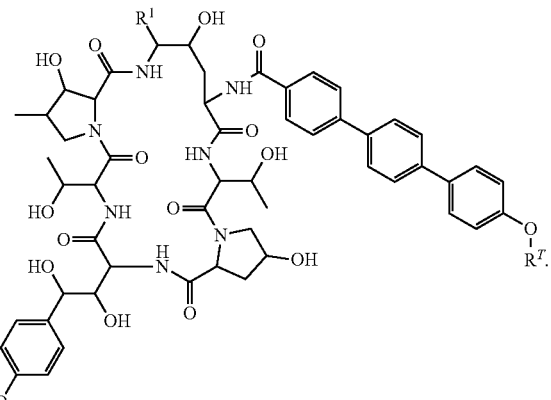

In formula (VIIb), $R^1$ is $O(CH_2CH_2O)_nCH_2CH_2X_1$, $O(CH_2CH_2CH_2O)_nCH_2CH_2X_1$, $NHCH_2CH_2X_2$, $NH(CH_2CH_2O)_mCH_2CH_2X_2$, $NH(CH_2CH_2CH_2O)_mCH_2CH_2X_2$, $NH(CH_2CH_2O)_pCH_2CH_2X_3$, $NH(CH_2CH_2CH_2O)_pCH_2CH_2X_3$, $NHCH_2CH_2X_4$, $NH[CH_2(CH_2)_aO]_bCH\{CH_2[OCH_2(CH_2)_c]_dX_5\}_2$, $O[CH_2(CH_2)_aC]_bCH\{CH_2[OCH_2(CH_2)_c]_dX_5\}_2$, $NH(CH_2CH_2NH)_rCH_2CH_2X_5$, $NHCH_2(CH_2)_qX_6$, or $OCH_2(CH_2)_qX_6$; $R^T$ is n-pentyl, sec-pentyl, or iso-pentyl; $X_1$ is $NHCH_2(CH_2)_vZ_1$; $X_2$ is $OCH_2(CH_2)_vZ_1$; $X_3$ is $NHCH_2(CH_2)_vZ_1$; $X_4$ is $NHCH_2(CH_2)_vZ_1$; each $X_5$ is, independently, selected from $OCH_2(CH_2)_vZ_1$ and $NHCH_2(CH_2)_vZ_1$; $X_6$ is $Z_1$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); n is an integer from 1 to 5 (e.g., 1, 2, 3, 4, or 5); m is an integer from 1 to 5 (e.g., 1, 2, 3, 4, or 5); p is an integer from 1 to 5 (e.g., 1, 2, 3, 4, or 5); r is an integer from 1 to 5 (e.g., 1, 2, 3, 4, or 5); q is an integer from 1 to 3 (e.g., 1, 2, or 3); v is an integer from 1 to 3 (e.g., 1, 2, or 3); $Z_1$ is selected from:

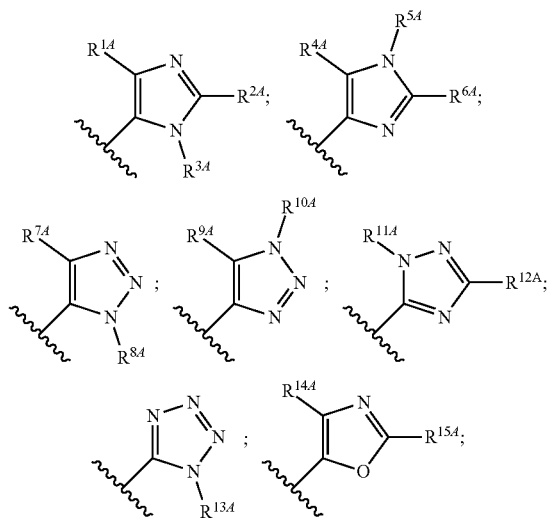

-continued

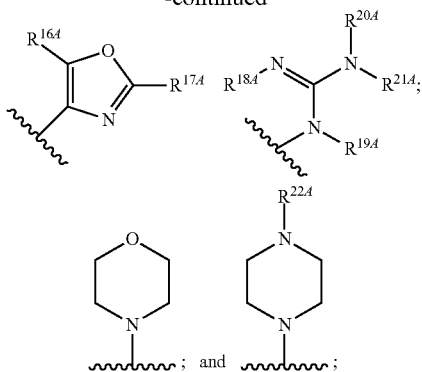

and each of $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, and $R^{22A}$ is, independently, selected from H, $CH_3$, $CH_2CH_3$, $CH_2CH_2CH_3$, and $CH(CH_3)_2$, or a pharmaceutically acceptable salt thereof.

In one particular embodiment of the compounds of formula (VII), (VIIa), and (VIIb), the compound is further described by one of the formulas:

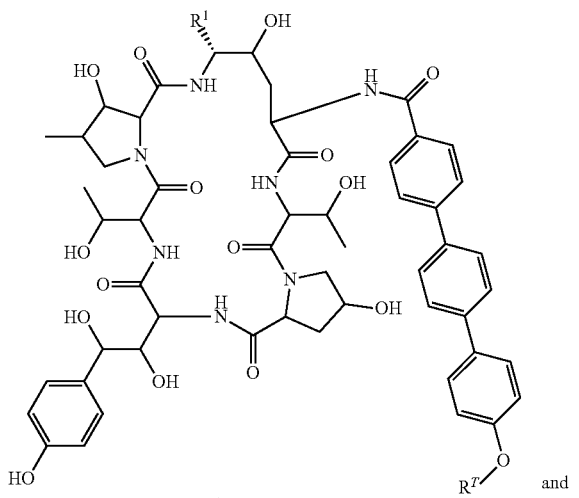

and

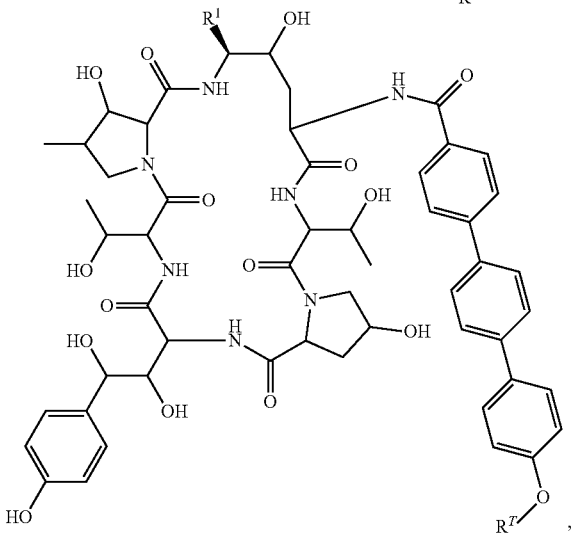

wherein $R^1$ and $R^T$ are as described in formula (VII).

The echinocandin class compound administered and/or formulated as described herein can be a compound of formula (VIII):

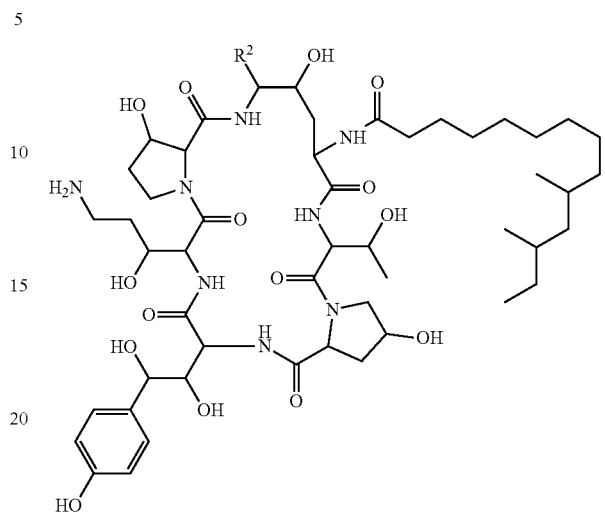

In formula (VIII), $R^2$ is $NH(CH_2CH_2O)_sCH_2$ $CH_2X_8$, $NH(CH_2CH_2CH_2O)_sCH_2CH_2X_8$, $NH(CH_2CH_2NH)_tCH_2CH_2X_9$, $NH[CH_2(CH_2)_aO]_bCH\{CH_2[OCH_2(CH_2)_c]_dX_9\}_2$, $O[CH_2(CH_2)_aC]_bCH\{CH_2[OCH_2(CH_2)_c]_dX_9\}_2$, $NHCH_2(CH_2)_uX_{10}$, or $OCH_2(CH_2)_uX_{10}$; $X_8$ is OH, $OR^{G1}$, $NH_2$, $NHR^{G1}$, $NR^{G1}R^{G2}$, $NR^{G1}R^{G2}R^{G3}$, $OCH_2(CH_2)_wZ_2$, or $NHCH_2(CH_2)_vZ_2$; each $X_9$ is independently, selected from OH, $OR^{H1}$, $NHR^{H1}$, $NR^{H1}R^{H2}$, $NR^{H1}R^{H2}R^{H3}$, $OCH_2(CH_2)_wZ_2$, and $NHCH_2(CH_2)_vZ_2$; $X_{10}$ is selected from $NR^{I1}R^{I2}R^{I3}$ or $Z_2$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); s is an integer from 1 to 5 (e.g., 1, 2, 3, 4, or 5); t is an integer from 1 to 5 (e.g., 1, 2, 3, 4, or 5); u is an integer from 1 to 3 (e.g., 1, 2, or 3); each of $R^{G1}$, $R^{G2}$, $R^{G3}$, $R^{H1}$, $R^{H2}$, $R^{H3}$, $R^{I1}$, $R^{I2}$, and $R^{I3}$ is, independently, selected from $CH_3$, $CH_2CH_3$, $CH_2CH_2CH_3$, and $CH(CH_3)_2$; w is an integer from 1 to 3 (e.g., 1, 2, or 3); $Z_2$ is selected from

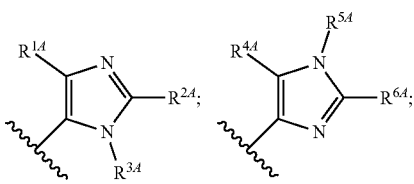
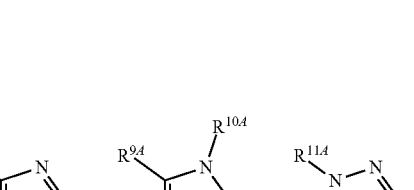
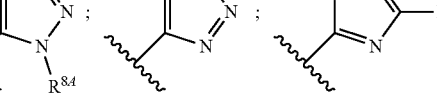
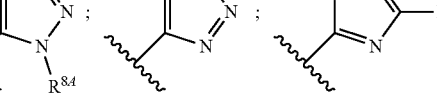

-continued

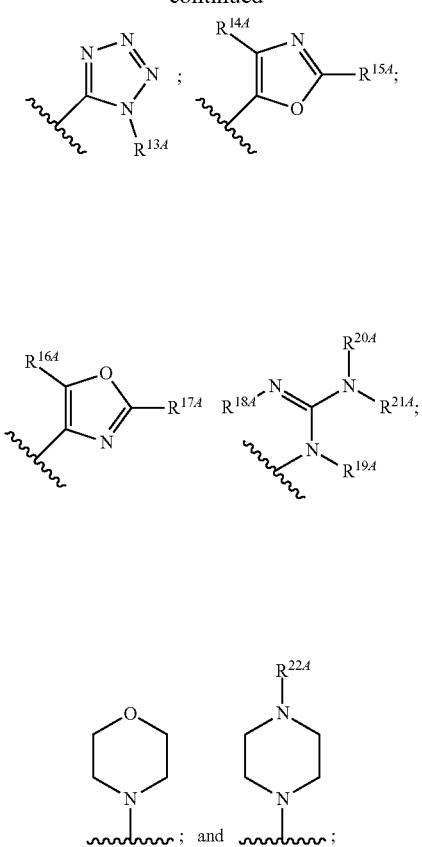

and each of $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, and $R^{22A}$ is, independently, selected from H, $CH_3$, $CH_2CH_3$, $CH_2CH_2CH_3$, and $CH(CH_3)_2$, or a pharmaceutically acceptable salt thereof.

In certain embodiments, the compound of formula (VIII) is further described by formula (VIIIa):

(VIIIa)

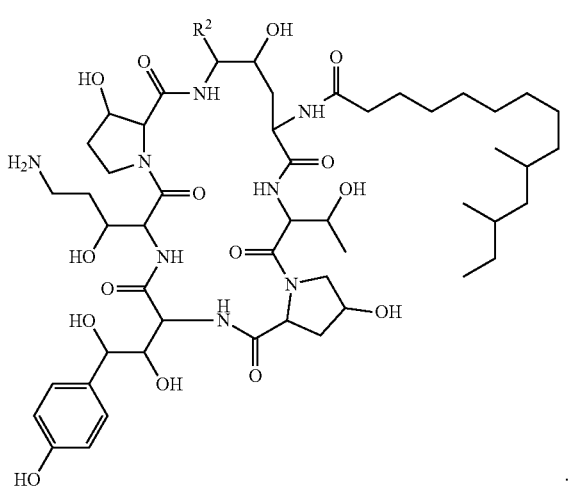

In formula (VIIIa), $R^2$ is $NH(CH_2CH_2O)_sCH_2CH_2X_8$, $NH(CH_2CH_2CH_2O)_sCH_2CH_2X_8$, $NH(CH_2CH_2NH)_tCH_2CH_2X_9$, $NH[CH_2(CH_2)_aO]_bCH\{CH_2[OCH_2(CH_2)_c]_dX_9\}_2$, $O[CH_2(CH_2)_aO]_bCH\{CH_2[OCH_2(CH_2)_c]_dX_9\}_2$, $NHCH_2(CH_2)_uX_{10}$, or $OCH_2(CH_2)_uX_{10}$; $X_8$ is OH, $OR^{G1}$, $NH_2$, $NHR^{G1}$, $NR^{G1}R^{G2}$, or $NR^{G1}R^{G2}R^{G3}$; each $X_9$ is, independently, selected from OH, $OR^{H1}$, $NHR^{H1}$, $NR^{H1}R^{H2}$, and $NR^{H1}R^{H2}R^{H3}$; $X_{10}$ is selected from $NR^{J1}R^{J2}R^{J3}$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); s is an integer from 1 to 5 (e.g., 1, 2, 3, 4, or 5); t is an integer from 1 to 5 (e.g., 1, 2, 3, 4, or 5); u is an integer from 1 to 3 (e.g., 1, 2, or 3); and each of $R^{G1}$, $R^{G2}$, $R^{G3}$, $R^{H1}$, $R^{H2}$, $R^{H3}$, $R^{J1}$, $R^{J2}$, and $R^{J3}$ is, independently, selected from $CH_3$, $CH_2CH_3$, $CH_2CH_2CH_3$, and $CH(CH_3)_2$, or a pharmaceutically acceptable salt thereof. In particular embodiments of the compounds of formula (II) and (IIa), one of $X_8$ and $X_9$ is selected from $N(CH_3)_3^+$ and $N(CH_2CH_3)_3^+$. In certain embodiments of the compounds of formula (II) and (IIa), $R^2$ is $NHCH[CH_2CH_2N(CH_3)_3^+]_2$, $NHCH_2CH_2OCH[CH_2CH_2N(CH_3)_3^+]_2$, or $NHCH_2CH_2OCH[CH_2CH_2N(CH_3)_3^+][CH_2CH_2OCH_2CH_2OH]$.

In still other embodiments, the compound of formula (I) is further described by formula (VIIIb):

(VIIIb)

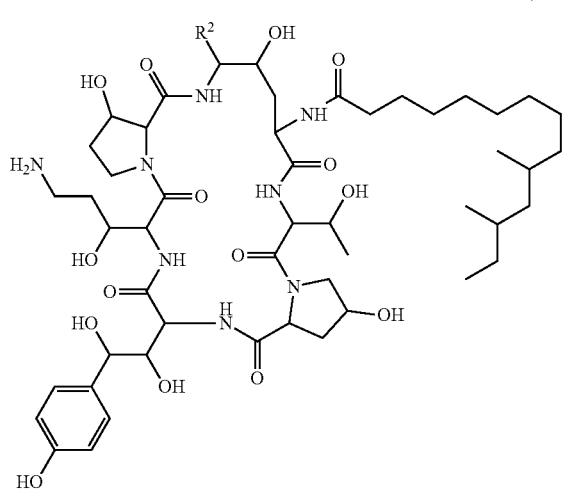

In formula (VIIIb), $R^2$ is $NH(CH_2CH_2O)_sCH_2CH_2X_8$, $NH(CH_2CH_2CH_2O)_sCH_2CH_2X_8$, $NH(CH_2CH_2NH)_tCH_2CH_2X_9$, $NH[CH_2(CH_2)_aO]_bCH\{CH_2[OCH_2(CH_2)_c]_dX_9\}_2$, $O[CH_2(CH_2)_aO]_bCH\{CH_2[OCH_2(CH_2)_c]_dX_9\}_2$, $NHCH_2(CH_2)_uX_{10}$, or $OCH_2(CH_2)_uX_{10}$; $X_8$ is $OCH_2(CH_2)_wZ_2$ or $NHCH_2(CH_2)_vZ_2$; each $X_5$ is, independently, selected from $OCH_2(CH_2)_wZ_2$ and $NHCH_2$ $(CH_2)_sZ_2$; $X_{10}$ is $Z_2$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); s is an integer from 1 to 5 (e.g., 1, 2, 3, 4, or 5); t is an integer from 1 to 5 (e.g., 1, 2, 3, 4, or 5); u is an integer from 1 to 3 (e.g., 1, 2, or 3); w is an integer from 1 to 3 (e.g., 1, 2, or 3); $Z_2$ is selected from

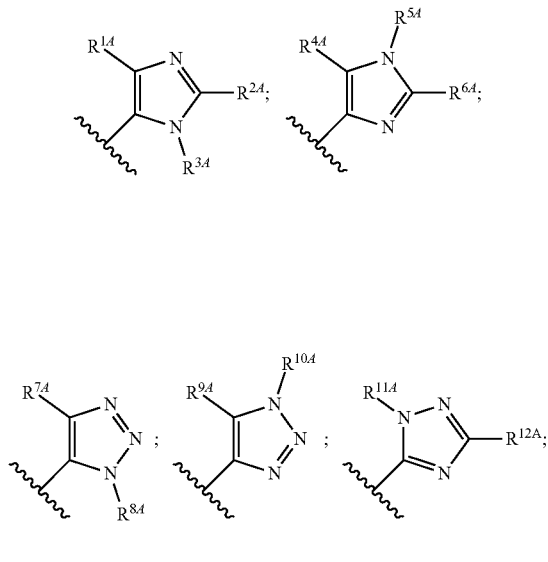

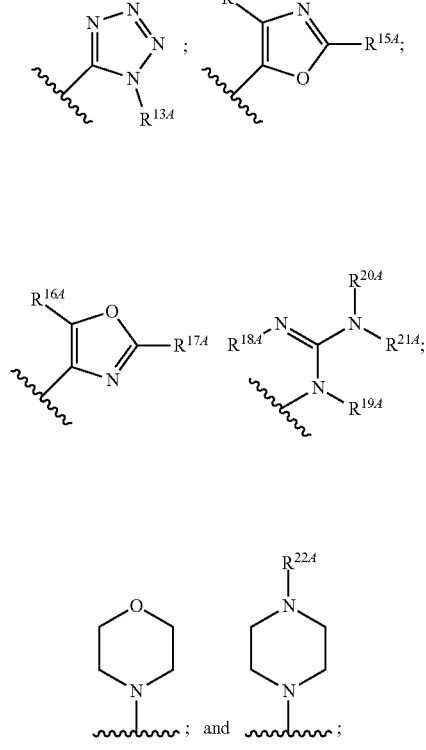

and each of $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, and $R^{22A}$ is, independently, selected from H, $CH_3$, $CH_2CH_3$, $CH_2CH_2CH_3$, and $CH(CH_3)_2$, or a pharmaceutically acceptable salt thereof.

In one particular embodiment of the compounds of formula (VIII), (VIIIa), and (VIIIb), the compound is further described by one of the formulas:

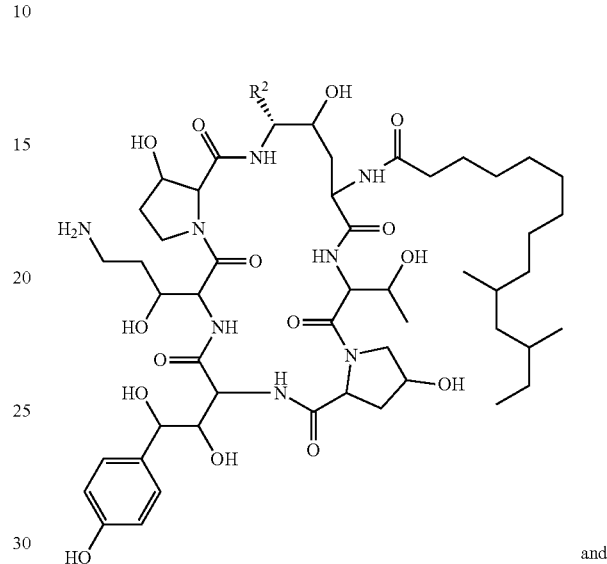

and

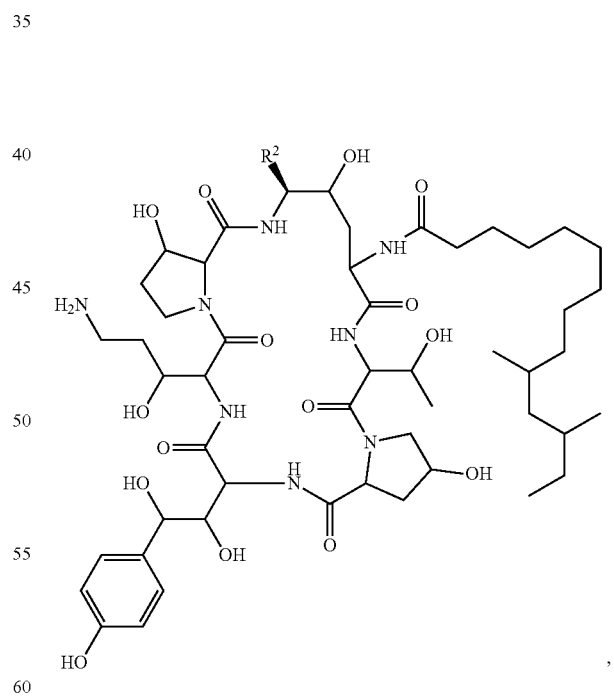

wherein $R^2$ is as described in formula (VIII).

The echinocandin class compound administered and/or formulated as described herein can be a compound of formula (IX):

(IX)

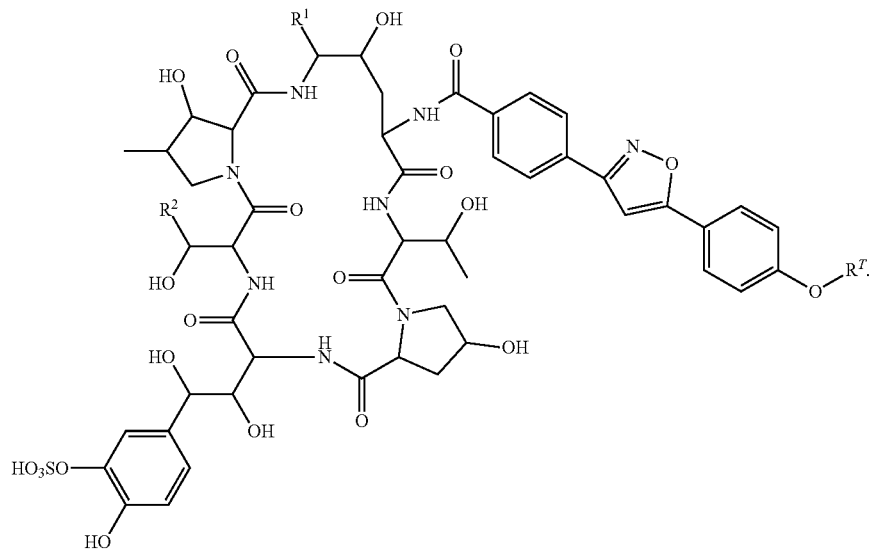

In formula (IX), $R^1$ is $O(CH_2CH_2O)_nCH_2CH_2X_1$, $O(CH_2CH_2CH_2O)_nCH_2CH_2X_1$, $NHCH_2CH_2X_2$, $NH(CH_2CH_2O)_nCH_2CH_2X_2$, $NH(CH_2CH_2CH_2O)_mCH_2CH_2X_2$, $NH(CH_2CH_2O)_pCH_2CH_2X_3$, $NH(CH_2CH_2CH_2O)_pCH_2CH_2X_3$, $NHCH_2CH_2X_4$, $NH[CH_2(CH_2)_aO]_bCH\{CH_2[OCH_2(CH_2)_c]_dX_5\}_2$, $O[CH_2(CH_2)_aC]_bCH\{CH_2[OCH_2(CH_2)_c]_dX_5\}_2$, $NH(CH_2CH_2NH)_rCH_2CH_2X_5$, $NHCH_2(CH_2)_qX_6$, or $OCH_2(CH_2)_qX_6$; $R^2$ is H, $CH_3$, $CH_2CH_2NH_2$, or $CH_2C(O)NH_2$; $R^T$ is n-pentyl, sec-pentyl, or iso-pentyl; $X_1$ is $NH_2$, $NHR^{A1}$, $NR^{A1}R^{A2}$, $NR^{A1}R^{A2}R^{A3}$, or $NHCH_2(CH_2)_vZ_1$; $X_2$ is OH, $OR^{B1}$, or $OCH_2(CH_2)_vZ_1$; $X_3$ is $NH_2$, $NHR^{C1}$, $NR^{C1}R^{C2}$, or $NR^{C1}R^{C2}R^{C3}$, or $NHCH_2(CH_2)_vZ_1$; $X_4$ is $NR^{D1}R^{D2}R^{D3}$ or $NHCH_2(CH_2)_vZ_1$; each $X_5$ is, independently, selected from OH, $OR^{E1}$, $NH_2$, $NHR^{E1}$, $NR^{E1}R^{E2}$, $NR^{E1}R^{E2}R^{E3}$, $OCH_2(CH_2)_vZ_1$, and $NHCH_2(CH_2)_vZ_1$; $X_6$ is selected from $NR^{F1}R^{F2}R^{F3}$ or $Z_1$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); n is an integer from 1 to 5 (e.g., 1, 2, 3, 4, or 5); m is an integer from 1 to 5 (e.g., 1, 2, 3, 4, or 5); p is an integer from 1 to 5 (e.g., 1, 2, 3, 4, or 5); r is an integer from 1 to 5 (e.g., 1, 2, 3, 4, or 5); q is an integer from 1 to 3 (e.g., 1, 2, or 3); v is an integer from 1 to 3 (e.g., 1, 2, or 3); each of $R^{A1}$, $R^{A2}$, $R^{A3}$, $R^{B1}$, $R^{C1}$, $R^{C2}$, $R^{C3}$, $R^{D1}$, $R^{D2}$, $R^{D3}$, $R^{E1}$, $R^{E2}$, $R^{E3}$, $R^{F1}$, $R^{F2}$, and $R^{F3}$ is, independently, selected from $CH_3$, $CH_2CH_3$, $CH_2CH_2CH_3$, and $CH(CH_3)_2$; $Z_1$ is selected from:

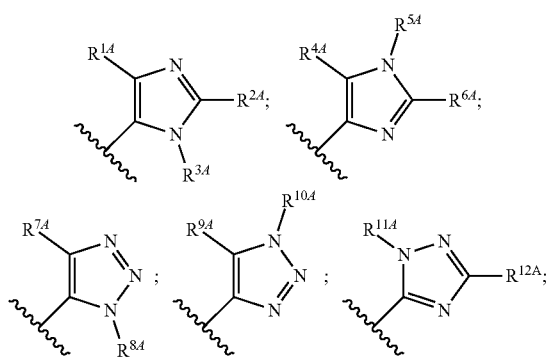

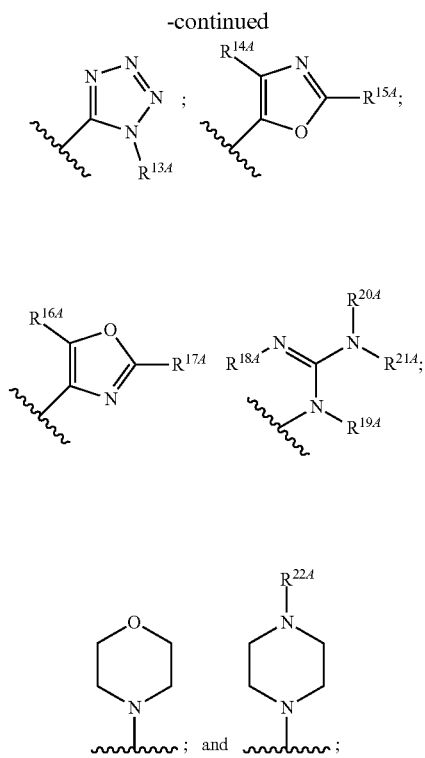

and each of $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, and $R^{22A}$ is, independently, selected from H, $CH_3$, $CH_2CH_3$, $CH_2CH_2CH_3$, and $CH(CH_3)_2$, or a pharmaceutically acceptable salt thereof. In particular embodiments of the compounds of formula (IX), one of $X_1$, $X_3$, $X_4$, $X_5$, and $X_6$ is selected from $N(CH_3)_3^+$ and $N(CH_2CH_3)_3^+$.

In one particular embodiment of the compounds of formula (IX), the compound is further described by one of the formulas:

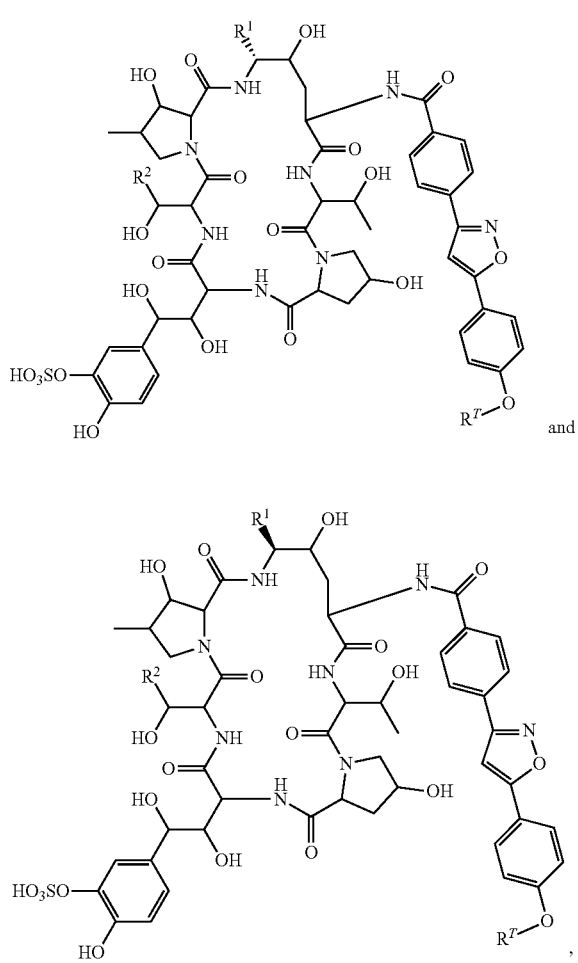

wherein $R^1$, $R^2$, and $R^T$ are as described in formula (IX).

Any of compounds 1-46 (depicted in FIGS. 1-14), or a pharmaceutically acceptable salt thereof, can be used in the methods and compositions of the invention.

Oral Dosage Formulations

The present invention features oral dosage formulations having additives including acyl carnitines, alkyl saccharides, ester saccharides, amido fatty acids, ammonium sulfonate surfactants, bile acids and salts (including cholic acid and salts thereof), chitosan and derivatives thereof, fatty acids and salts or esters thereof, glycerides, hydrophilic aromatic alcohols, pegylated phospholipids, peptide epithelial tight junction modulators, phospholipids, polyethylene glycol alkyl ethers, polyglycolized glycerides, polyglycerol fatty acid esters, polysorbate surfactants, carboxylic acids, polyethylene glycols, or a mixture thereof. These additives can increase the oral bioavailability of echinocandin class compounds, and pharmaceutically acceptable salts thereof.

Acyl Carnitines

Acyl carnitines can be used in the oral dosage forms of the invention, in either their zwitter ion form or salt form. Acyl carnitines can be derived carnitine (D or L form, or a mixture thereof) and a fatty acid including, without limitation, fatty acids having 16 carbon atoms and 0, 1 or 2 double bonds (C16:0; C16:1 and C16:2), those with 18 carbon atoms and 1, 2 or 3 double bonds (C18:1; C18:2; and C18:3), those with 20 carbon atoms and 1, 2 or 4 double bonds (C20:1; C20:2; and C20:4) and those with 22 carbon atoms and 4, 5 or 6 double bonds (C22:4; C22:5 and C22:6). Exemplary acyl carnitines which are useful additives in the formulations of the invention include oleoyl carnitine, palmitoyl carnitine, decanoyl carnitine, dodecanoyl carnitine, myristoyl carnitine, and stearoyl carnitine.

Alkyl Saccharides

Alkyl saccharides can be used in the oral dosage forms of the invention. Alkyl saccharides are sugar ethers of a hydrophobic alkyl group (e.g., typically from 9 to 24 carbon atoms in length). Alkyl saccharides include alkyl glycosides and alkyl glucosides. In particular embodiments, the echinocandin class compound is formulated with a $C_{8-14}$ alkyl ether of a sugar. Alkyl glycosides that can be used in the oral dosage forms of the invention include, without limitation, $C_{8-14}$ alkyl (e.g., octyl-, nonyl-, decyl-, undecyl-, dodecyl-, tridecyl-, or tetradecyl-) ethers of α or β-D-maltoside, -glucoside or -sucroside, alkyl thiomaltosides, such as heptyl, octyl, dodecyl-, tridecyl-, and tetradecyl-β-D-thiomaltoside; alkyl thioglucosides, such as heptyl- or octyl 1-thio α- or β-D-glucopyranoside; alkyl thiosucroses; and alkyl maltotriosides. For example, the echinocandin class compound can be formulated with octyl maltoside, dodecyl maltoside, tridecyl maltoside, or tetradecyl maltoside. Alkyl glucosides that can be used in the oral dosage forms of the invention include, without limitation, $C_{8-14}$ alkyl (e.g., octyl-, nonyl-, decyl-, undecyl-, dodecyl-, tridecyl-, or tetradecyl-) ethers of glucoside, such as dodecyl glucoside or decyl glucoside.

Amido Fatty Acids

Amido fatty acids can be used in the oral dosage forms of the invention. Amido fatty acids are long chain amino acid amides of formula (A), and salts thereof:

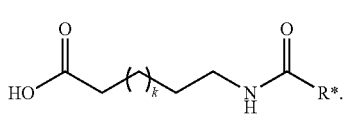

(A)

In formula (A), k is an integer from 1 to 10 and R* is $C_{5-8}$ alkyl, $C_{6-12}$ aryl, $C_{7-16}$ alkaryl, $C_{3-10}$ alkheterocyclyl, and $C_{2-10}$ heterocyclyl. Amido fatty acids include those described in U.S. Pat. Nos. 5,650,386 and 8,110,547, each of which is incorporated herein by reference. In particular embodiments, k is an integer from 1 to 7 and R* is $C_{6-12}$ aryl or $C_{7-16}$ alkaryl. Exemplary amido fatty acids which are useful additives in the formulations of the invention include (i) N-[8-(2-hydroxybenzoyl)amino]caprylic acid (also known as "NAC"), and salts thereof, including its sodium salt (also known as "SNAC"); (ii) 8-(N-2-hydroxy-4-methoxybenzoyl)-aminocaprylic acid (also known as "4-MOAC"), and salts thereof, including its sodium salt; (iii) N-(8-[2-hydroxybenzoyl]-amino)decanoic acid (also known as "NAD"), and salts thereof, including its sodium salt (also known as "SNAD"); (iv) N-(8-[2-hydroxy-5-chlorobenzoyl]-amino)octanoic acid (also known as "5-CNAC"), and salts thereof, including its sodium salt; and (iv) 4-[(2-hydroxy-4-chlorobenzoyl)amino]butanoate (also known as "4-CNAB"), and salts thereof, including its sodium salt.

Ammonium Sulfonate Surfactants

Ammonium sulfonate surfactants can be used in the oral dosage forms of the invention. Ammonium sulfonate surfactants are zwitterionic additives of formula (B):

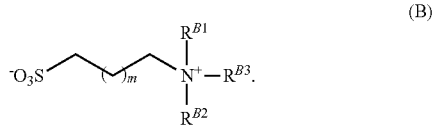

(B)

In formula (B), m is an integer from 0 to 3, each of $R^{B1}$ and $R^{B2}$ are, independently, selected from methyl, ethyl, and propyl; and $R^{B3}$ is a saturated or unsaturated alkyl of 6 to 18 carbons in length. Exemplary ammonium sulfonate surfactants which can be useful additives in the formulations of the invention include N-alkyl-N,N-dimethylammonio-1-propanesulfonates, such as dimethylpalmityl-amino propanesulfonate (DPPS).

Bile Acids and Salts

Bile acids and salts can be used in the oral dosage forms of the invention. For example, the formulations can include, without limitation, bile acids and salts such as sodium cholate, sodium glycocholate, sodium glycodeoxycholate, taurodeoxycholate, sodium deoxycholate, sodium taurodihydrofusidate, taurocholate, and ursodeoxycholate, sodium lithocholate, chenocholate, chenodeoxycholate, ursocholate, ursodeoxycholate, hyodeoxycholate, dehydrocholate, glycochenocholate, taurochenocholate, taurochenodeoxycholate, or their corresponding acids.

Chitosan and Derivatives Thereof

Chitosan and derivatives thereof can be used in the oral dosage forms of the invention. Chitosan is prepared by the deacetylation of chitin. For use in the formulations of the invention, the degree of deacetylation, which represents the proportion of N-acetyl groups which have been removed through deacetylation, should be in the range of from about 40 to about 100%, (e.g., 60 to about 96% or 70 to 95%). Desirably, the chitosan, or chitosan derivative, should have a molecular weight of from about 3,000 to about 1,000,000 Da (e.g., from about 10,000 to about 800,000 Da, from about 15,000 to about 600,000 Da, or from 30,000 or 50,000 to about 600,000 Da). Chitosan derivatives include pharmaceutically acceptable organic and inorganic salts (e.g., nitrate, phosphate, acetate, hydrochloride, lactate, citrate and glutamate salts, among others). Chitosan derivatives can be prepared by bonding moieties to the hydroxyl or amino groups of chitosan and may confer the polymer with changes in properties such as solubility characteristics and charge density. Examples include O-alkyl ethers of chitosan and O-acyl esters of chitosan. Other examples of chitosan derivatives include carboxymethyl chitosan (see Thanou et al, J. Pharm. Sci., 90:38 (2001)) and N-carboxymethyl chitosan derivatives, trimethylchitosan (see Thanou et al, Pharm. Res., 17:27 (2000)), thiolated chitosans (see Bernkop-Schnurch et al, Int. J. Pharm., 260:229 (2003)), piperazine derivatives (see PCT Publication No. WO 2007/034032 and Holappa et al, Macromol. Biosci., 6:139 (2006)), PEG-conjugated chitosan (see PCT Publication No. WO 99/01498), and those derivatives disclosed in Roberts, Chitin Chemistry, MacMillan Press Ltd., London (1992). Exemplary chitosan and chitosan derivatives which are useful additives in the formulations of the invention include chitosan, trimethylchitosan, and chitosan-4-thio-butylamidine (see Sreenivas et al., International Journal of PharmTech Research 1:670 (2009)).

Ester Saccharides

Ester saccharides can be used in the oral dosage forms of the invention. Ester saccharides are sugar esters of a hydrophobic alkyl group (e.g., typically from 8 to 24 carbon atoms in length). Ester saccharides include ester glycosides and ester glucosides. In particular embodiments, the echinocandin class compound is formulated with a $C_{8-14}$ alkyl ester of a sugar. Ester glycosides that can be used in the oral dosage forms of the invention include, without limitation, $C_{8-14}$ alkyl (e.g., octyl-, nonyl-, decyl-, undecyl-, dodecyl-, tridecyl-, or tetradecyl-) esters of a or β-D-maltoside, -glucoside or -sucroside. For example, the echinocandin class compound can be formulated with sucrose mono-dodecanoate, sucrose mono-tridecanoate, or sucrose mono-tetradecanoate. Ester glucosides that can be used in the oral dosage forms of the invention include, without limitation, $C_{8-14}$ alkyl (e.g., octyl-, nonyl-, decyl-, undecyl-, dodecyl-, tridecyl-, or tetradecyl-) esters of glucoside, such as glucose dodecanoate or glucose decanoate.

Fatty Acids

Fatty acids can be used in the oral dosage forms of the invention. Fatty acids which can be used in the oral dosage forms of the invention, in either their acid form, salt form, monoester form, or glyceride form, include caprylic acid (octanoic acid), pelargonic acid (nonanoic acid), capric acid (decanoic acid) and lauric acid (dodecanoic acid), and their primary hydroxyl forms 8-hydroxy octanoic acid, 9-hydroxy nonanoic acid, 10-hydroxy decanoic acid, and 12-hydroxy dodecanoic acid.

Fatty acids are commonly derived from natural fats, oils, and waxes by hydrolysis of esters and the removal of glycerol. Fatty acids can be titrated with sodium hydroxide solution using phenophthalein as an indicator to a pale-pink endpoint. This analysis is used to determine the free fatty acid content of fats; i.e., the proportion of the triglycerides that have been hydrolyzed.

Short-chain fatty acids such as acetic acid (pKa=4.76 in water) are miscible with water and dissociate to form acids. As its chain length increases, fatty acids do not substantially increase in $pK_a$. However, as the chain length increases the solubility of fatty acids in water decreases very rapidly. However, most fatty acids that are insoluble in water will dissolve in warm ethanol.

Any alcohol can be used to produce a corresponding fatty acid ester. The alcohols may be polyalcohols such as ethylene glycol or glycerol. The alcohol may carry a permanent positive charge, which makes the ester mucoadhesive (that is, adhesive to musoca). Methods of esterification are well-known in the art (e.g., Fischer esterification in acid). Fatty acid esters include fatty acid ethyl esters and fatty acid methyl esters.

Glycerides

Glycerides can be used in the oral dosage forms of the invention. Glycerides are fatty acid mono-, di-, and tri-esters of glycerol. A variety of glycerides can be used as a sustained release fatty acid for the formulation of an echinocandin class compound. Glycerides include saturated and unsaturated monoglycerides, diglyceridies (1,2- and 1,3-diglycerides), and triglycerides, with mixed and unmixed fatty acid composition. Each glyceride is herein designated as (Cn:m), where n is the length of the fatty acid side chain and m is the number of double bonds (cis- or trans-) in the fatty acid side chain. Examples of commercially available monoglycerides include: monocaprylin (C8; i.e., glyceryl monocaprylate) (Larodan), monocaprin (C10; i.e., glyceryl monocaprate) (Larodan), monolaurin (C12; i.e., glyceryl monolaurate) (Larodan), monopalmitolein (C16:1) (Larodan), glyceryl monomyristate (C14) (Nikkol MGM, Nikko), glyceryl monooleate (C18:1) (PECEOL, Gattefosse), glyceryl monooleate (Myverol, Eastman), glycerol monooleate/linoleate (OLICINE, Gattefosse), glycerol monolinoleate (Maisine, Gattefosse), and monoelaidin (C18:1) (Larodan). Examples commercially available mono/di and tri glycerides include Capmul MCM C8EP, (C8:C10 mono/di glycerides) and Capmul MCM C10 (mono/di glycerdies). Examples commercially available diglycerides include: glyceryl laurate (Imwitor® 312, Huls), glyceryl caprylate/caprate (Capmul® MCM, ABITEC), caprylic acid diglycerides (Imwitor® 988, Huls), caprylic/capric glycerides (Imwitor® 742, Huls), dicaprylin (C8) (Larodan), dicaprin (C10) (Larodan), dilaurin (C12) (Larodan), glyceryl dilaurate (C12) (Capmul® GDL, ABITEC). Examples commercially available triglycerides include: tricaprylin (C8; i.e., glyceryl tricaprylate) (Larodan), capatex 100 (C10), tricaprin (C10; i.e., glyceryl tricaprate) (Larodan), trilaurin (C12; i.e., glyceryl trilaurate) (Larodan), dimyristin (C14) (Larodan), dipalmitin (C16) (Larodan), distearin (Larodan), glyceryl dilaurate (C12) (Capmul® GDL, ABITEC), glyceryl dioleate (Capmul® GDO, ABITEC), glycerol esters of fatty acids (GELUCIRE 39/01, Gattefosse), dipalmitolein (C16:1) (Larodan), 1,2 and 1,3-diolein (C18:1) (Larodan), dielaidin (C18:1) (Larodan), and dilinolein (C18:2) (Larodan).

Hydrophilic Aromatic Alcohols

Hydrophilic aromatic alcohols can be used in the oral dosage forms of the invention. Hydrophilic aromatic alcohols include, without limitation, phenoxyethanol, benzyl alcohol, phenylethanol, and additive described in U.S. Pat. No. 7,303,762, incorporated herein by reference.

Pegylated Phospholipids

Pegylated phospholipids can be used in the oral dosage forms of the invention. Pegylated phospholipids are additives that include a polyethylene oxide group (i.e., polyethylene glycol group) covalently coupled to the phospholipid, typically through a carbamate or an ester bond. Phospholipids are derived from glycerol and include a phosphate ester group and two fatty acid ester groups. Suitable fatty acids include saturated and unsaturated fatty acids having from eight (8) to twenty-two (22) carbons atoms (i.e., any fatty acid described herein). Representative polyethylene oxide-containing phospholipids include C8-C22 saturated fatty acid esters of a phosphatidyl ethanolamine polyethylene glycol salt. Representative average molecular weights for the polyethylene oxide groups can be from about 200 to about 5000 (e.g., PEG 200 to PEG 5000). Pegylated phospholipids include, without limitation, distearoyl phosphatidyl ethanolamine polyethylene glycol salts, such as distearoylphosphatidyl ethanolamine polyethylene glycol 350 (DSPE-PEG-350) salts, distearoylphosphatidyl ethanolamine polyethylene glycol 550 (DSPE-PEG-550) salts, distearoylphosphatidyl ethanolamine polyethylene glycol 750 (DSPE-PEG-750) salts, distearoylphosphatidyl ethanolamine polyethylene glycol 1000 (DSPE-PEG-1000) salts, distearoylphosphatidyl ethanolamine polyethylene glycol 1500 (DSPE-PEG-1500) salts, and distearoylphosphatidyl ethanolamine polyethylene glycol 2000 (DSPE-PEG-2000) salts. Mixtures can also be used. For the distearoylphosphatidyl ethanolamine polyethylene glycol salts above, the number (e.g., 350, 550, 750, 1000, and 2000) designates the average molecular weight of the polyethylene oxide group. Suitable distearoylphosphatidyl ethanolamine polyethylene glycol salts include ammonium and sodium salts.

Peptide Epithelial Tight Junction Modulators

Peptide epithelial tight junction modulators can be used in the oral dosage forms of the invention. The oral dosage formulations of the invention can include a peptide epithelial tight junction modulator. The tight junction or zonula occludens (hereinafter "ZO") are one of the hallmarks of absorptive and secretory epithelia (Madara, J. Clin. Invest., 83:1089-1094 (1989); and Madara, Textbook of Secretory Diarrhea Eds, Lebenthal et al, Chapter 11, pages 125-138 (1990)). As a barrier between apical and basolateral compartments, they selectively regulate the passive diffusion of ions and water-soluble solutes through the paracellular pathway (Gumbiner, Am. J. Physiol., 253 (Cell Physiol. 22): C749-C758 (1987)). This barrier maintains any gradient generated by the activity of pathways associated with the transcellular route (Diamond, Physiologist, 20:10-18 (1977)). Variations in transepithelial conductance can usually be attributed to changes in the permeability of the paracellular pathway, since the resistances of enterocyte plasma membranes are relatively high. The ZO represents the major barrier in this paracellular pathway, and the electrical resistance of epithelial tissues depends on the number of transmembrane protein strands, and their complexity in the ZO, as observed by freeze-fracture electron microscopy (Madara et al, J. Cell Biol., 101:2124-2133 (1985)). Six proteins have been identified in a cytoplasmic submembranous plague underlying membrane contacts. ZO-1 and ZO-2 exist as a heterodimer (Gumbiner et al, Proc. Natl. Acad. Sci., USA, 88:3460-3464 (1991)) in a detergent-stable complex with ZO-3. Two other proteins, cingulin (Citi et al, Nature (London), 333:272-275 (1988)) and the 7H6 antigen (Zhong et al, J. Cell Biol., 120:477-483 (1993)) are localized further from the membrane. Rab 13, a small GTP binding protein has also recently been localized to the junction region (Zahraoui et al, J. Cell Biol., 124:101-115 (1994)). Certain peptide modulators acting at ZO-1, ZO-2, ZO-3, cingulin, and/or 7H6 have been shown to be capable of reversibly opening tight junction in the intestinal mucosa, and so, when co-administered with a therapeutic agent, are able to effect intestinal delivery of the therapeutic agent, when employed in an oral dosage composition for intestinal drug delivery (see PCT Publication No. WO 96/37196; U.S. Pat. Nos. 5,665,389, 5,945,510, 6,458,925, and 6,733,762; and Fasano et al., J. Clin. Invest., 99:1158 (1997); each of which is incorporated herein by reference). An exemplary peptide epithelial tight junction modulator is the peptide known as pn159 (see U.S. Patent Publication No. US 2006/0062758 A1, incorporated herein by reference)

Phospholipids

Phospholipids can be used in the oral dosage forms of the invention. Phospholipids are additives that include a di-fatty acid ester of a phosphorylated glycerol. Suitable fatty acids include saturated and unsaturated fatty acids having from eight (8) to twenty-two (22) carbons atoms (i.e., any fatty acid described herein). Representative phospholipids include C8-C22 saturated fatty acid esters of phosphatidyl choline and 1-palmtoyl-2-glutaroyl-sn-glycero-3-Phosphocholine (PGPC).

Polyethylene Glycol Alkyl Ethers

Ethers of polyethylene glycol and alkyl alcohols can be used in the oral dosage forms of the invention. Preferred polyethylene glycol alkyl ethers include Laureth 9, Laureth 12 and Laureth 20. Other polyethylene glycol alkyl ethers include, without limitation, PEG-2 oleyl ether, oleth-2 (Brij 92/93, Atlas/ICI); PEG-3 oleyl ether, oleth-3 (Volpo 3, Croda); PEG-5 oleyl ether, oleth-5 (Volpo 5, Croda); PEG-10 oleyl ether, oleth-10 (Volpo 10, Croda, Brij 96/97 12, Atlas/ICI); PEG-20 oleyl ether, oleth-20 (Volpo 20, Croda, Brij 98/99 15, Atlas/ICI); PEG-4 lauryl ether, laureth-4 (Brij 30, Atlas/ICI); PEG-9 lauryl ether; PEG-23 lauryl ether, laureth-23 (Brij 35, Atlas/ICI); PEG-2 cetyl ether (Brij 52, ICI); PEG-10 cetyl ether (Brij 56, ICI); PEG-20 cetyl ether (Brij 58, ICI); PEG-2 stearyl ether (Brij 72, ICI); PEG-10 stearyl ether (Brij 76, ICI); PEG-20 stearyl ether (Brij 78, ICI); and PEG-100 stearyl ether (Brij 700, ICI).

Polyglycolized Glycerides

Polyglycolized glycerides can be used in the oral dosage forms of the invention. Polyglycolized glycerides are mono-, di-, and tri-fatty acid esters of glycerol having at least one polyglycol (e.g., polyethylene glycol or polypropylene glycol) moiety. Polyglycolized glycerides often occur as mixtures that result from the transesterification of natural oils with the corresponding polyglycol.

The polyglycolized glycerides useful in the formulations of the invention can include polyethylene glycol or polypropylene glycol glyceride monoesters, diesters, and/or triesters of acetic, propionic, butyric, valeric, hexanoic, heptanoic, caprylic, nonanoic, capric, lauric, myristic, palmitic, heptadecanoic, stearic, arachidic, behenic, lignoceric, α-linolenic, stearidonic, eicosapentaenoic, docosahexaenoic, linoleic, γ-linolenic, dihomo-γ-linolenic, arachidonic, oleic, elaidic, eicosenoic, erucic, or nervonic acid, C12 fatty acids, C14 fatty acids, C16 fatty acids, and C18 fatty acids, and mixtures thereof Polyglycerol Fatty Acid Esters Polyglycerol fatty acid esters can be used in the oral dosage forms of the invention. Polyglycerol fatty acid esters are fatty acid esters of polyglycerol (e.g., diglycerol, triglycerol, tetraglycerol, hexaglycerol). The polyglycerol fatty acid esters useful in the formulations of the invention can include, without limitation, polyglycerol bearing 1 to 12 fatty acid esters of valeric, hexanoic, heptanoic, caprylic, nonanoic, capric, lauric, myristic, palmitic, heptadecanoic, stearic, arachidic, behenic, lignoceric, α-linolenic, stearidonic, eicosapentaenoic, docosahexaenoic, linoleic, γ-linolenic, dihomo-γ-linolenic, arachidonic, oleic, elaidic, eicosenoic, erucic, or nervonic acid, C12 fatty acids, C14 fatty acids, C16 fatty acids, and C18 fatty acids, and mixtures thereof. Exemplary polyglycerol fatty acid esters include polyglyceryl oleate (Plurol Oleique), polyglyceryl-2 dioleate (Nikkol DGDO), polyglyceryl-10 trioleate, polyglyceryl-10 laurate (Nikkol Decaglyn 1-L), polyglyceryl-10 oleate (Nikkol Decaglyn 1-O), polyglyceryl polyricinoleates (Polymuls), polyglyceryl-2 stearate (Nikkol DGMS), polyglyceryl-2 oleate (Nikkol DGMO), polyglyceryl-2 isostearate Nikkol DGMIS (Nikko), polyglyceryl-3 oleate (Caprol, ABITEC), polyglyceryl-4 oleate (Nikkol Tetraglyn 1-O), polyglyceryl-4 stearate (Nikkol Tetraglyn 1-S), polyglyceryl-6 oleate, polyglyceryl-10 laurate (Nikkol Decaglyn 1-L), polyglyceryl-10 oleate (Nikkol Decaglyn 1-O), polyglyceryl-10 stearate (Nikkol Decaglyn 1-S), polyglyceryl-6 ricinoleate (Nikkol Hexaglyn PR-15), polyglyceryl-10 linoleate (Nikkol Decaglyn 1-LN), and polyglyceryl-6 dioleate (PLUROL OLEIQUE).

Polysorbate Surfactants

Polysorbate surfactants can be used in the oral dosage forms of the invention. Polysorbate surfactants are oily liquids derived from pegylated sorbitan esterified with fatty acids. Common brand names for Polysorbates include Alkest, Canarcel and Tween. Polysorbate surfactants include, without limitation, polyoxyethylene 20 sorbitan monolaurate (TWEEN 20), polyoxyethylene (4) sorbitan monolaurate (TWEEN 21), polyoxyethylene 20 sorbitan monopalmitate (TWEEN 40), polyoxyethylene 20 sorbitan monostearate (TWEEN 60); and polyoxyethylene 20 sorbitan monooleate (TWEEN 80).

Carboxylic Acids

Carboxylic acids can be used in the oral dosage forms of the invention. Preferred carboxylic acids include citric acid, succinic acid, tartaric acid, fumaric acid, maleic acid, malonic acid, glutaric acid, adipic acid, lactic acid, malic acid, L-glutamic acid, L-aspartic acid, gluconic acid, glucuronic acid, salicylic acid, and mixtures thereof Polyethylene Glycols Polyethylene glycols can be used in the oral dosage forms of the invention. Preferred polyethylene glycols include PEG2 to PEG 5000 (e.g., PEG 200, PEG 400, PEG 800, PEG 1,200, and mixtures thereof.

Taste-Masked Formulations

Taste-masked formulations can be prepared by adsorbing the additive and drug onto a matrix (e.g., an organic matrix or inorganic matrix) to form a solid complex containing the liquid additive and drug. Exemplary organic matrices that can be used in the taste-masked formulations of the invention include, without limitation, cellulose acetate, amorphous cellulose, starch, polyurethanes, polyvinyl alcohol, polyacrylates, mannitol, Avicel PH101, and Avicel PH102. Exemplary inorganic matrices that can be used in the taste-masked formulations of the invention include, without limitation, silica (e.g., Aerosil, Aeroperl, amorphous silica, colloidal silica), silicates (e.g., Neusilin, hectrorite), carbonates (e.g., magnesium carbonate), and metal oxides (e.g., magnesium oxide).

For example, taste-masked formulations can be prepared by adsorbing the additive and drug onto a porous silicate (see PCT Publication No. WO 00/38655). The porous silicate can be a swelling clay of the smectite type (e.g., bentonite, veegum, laponite), hydrous aluminium silicates or alkaline earth silicates (e.g., Neusilin, hectrorite, among others), or a porous silica gel (e.g., Syloid, Porasil, Lichrosorp). In a typical taste-masked formulation the additive and drug are adsorbed onto silicate selected from sodium silicate, potassium silicate, magnesium silicate, calcium silicate (including synthetic calcium silicate such as, e.g., Hubersorp), zinc silicate, aluminum silicate, sodium aluminosilicate such as, for example, Zeolex, magnesium aluminum silicate, magnesium aluminum metasilicate, aluminum metasilicate, Neusilin UFL2 (type 1-A), Neusilin (SG2), Neusilin (F1), and Neusilin (US2), or mixtures thereof.

The taste-masked formulation can be designed to form a powder that is reconstitutable in water. The incorporation of the additive and drug into the matrix minimizes contact with the taste buds of the subject and allows the taste of the formulation to be controlled with one or more additional flavorings (e.g., lemon, menthol, etc.) and sweeteners (e.g., sugars, sugar alcohols, aspartame, etc.).

Methods for making formulations for oral administration are found, for example, in "Remington: The Science and Practice of Pharmacy" (20th ed., ed. A. R. Gennaro, 2000, Lippincott Williams & Wilkins). Formulations for oral administration (e.g., tablets, pills, caplets, hard capsules, soft capsules, sachets, and liquid dosage forms) may, for example, contain any one or combination of the additives described above along with other additives and/or excipients as needed. Liquid-filled capsules can include any of the additives described herein. The capsule will contain from, for example, 10 to about 1,000 mg of an echinocandin class compound. Liquid-filled capsules may, for example, contain either solutions or suspensions of an echinocandin class compound, depending upon the concentration of echinocandin class compound within the capsule and the additives used in the formulation.

A particular formulation of the invention can include multiple additives (e.g., a combination two or three) to achieve not only an enhancement in oral bioavailability, but also a reduced weight percentage of additives in the formulation, allowing higher drug loadings. Thus, a combination of (i) a fatty acid, or a salt or ester thereof, with an alkyl saccharide or ester saccharide; (ii) a glyceride with an acyl carnitine; (iii) a fatty acid, or a salt or ester thereof, with an acyl carnitine; or (iv) a glyceride with a pegylated phospholipid can be used in the oral dosage forms of the invention. These combinations of enhancers can work synergistically to increase oral absorption of the drug over longer window of time, increase the overall bioavailability of the unit dosage form, and/or reduced the overall weight percentage of additive needed in the formulation.

The echinocandin class compounds of the invention can be formulated as a clear aqueous dispersion as described in U.S. Pat. No. 6,309,663 and U.S. Patent Publication Nos. 2005/0096296, 2005/0171193, 2003/104048, 2006/003493, and 2003/0215496, each of which are incorporated herein by reference. For example, a formulation of the invention can include (i) at least one hydrophilic surfactant selected from ionized ionizable surfactants, non-ionic hydrophilic surfactants having an HLB value greater than or equal to about 10, and combinations thereof, and (ii) at least one hydrophobic surfactant selected from hydrophobic (a) alcohols, polyoxyethylene alkylethers, bile acids, glycerol fatty acid monoesters, glycerol fatty acid diesters, acetylated glycerol fatty acid monoesters, acetylated glycerol fatty acid diesters, lower alcohol fatty acid monoesters, lower alcohol fatty acid diesters, polyethylene glycol fatty acid esters, polyethylene glycol glycerol fatty acid esters, polypropylene glycol fatty acid esters, polyoxyethylene glycerides, lactic acid derivatives of mono- and diglycerides, propylene glycol diglycerides, sorbitan fatty acid esters, polyoxyethylene sorbitan fatty acid esters, polyoxyethylene-polyoxypropylene block copolymers, transesterified vegetable oils, sugar esters, sugar ethers, sucroglycerides, polyoxyethylene vegetable oils, polyoxyethylene hydrogenated vegetable oils, reaction products of polyols and at least one member of the group consisting of fatty acids, glycerides, vegetable oils, and hydrogenated vegetable oils, and hydrophobic, (b) unionized fatty acids, carnitine fatty acid esters, alkylsulfates, acyl lactylates, mono-acetylated tartaric acid esters of mono- and diglycerides, diacetylated tartaric acid esters of mono- and diglycerides, succinylated monoglycerides, glyceryl stearate, citric acid esters of mono- and diglycerides, and mixtures thereof. The hydrophilic and hydrophobic surfactants are present in amounts such that upon mixing with an aqueous diluent at 100 times dilution, the composition forms a clear aqueous dispersion having an absorbance of less than about 0.3 at 400 nm. The clear aqueous dispersion can include bile acids and/or bile salts. The composition can be included in a solid carrier, such as a suspension in carrier in a capsule. Hyrdophilic surfactants that can be used in this type of formulation include PEG20 sorbitan monolaurate, PEG20 sorbitan monooleate, and/or polyoxyethyl glycerided (e.g., PEG8 caprylic/capric glycerides).

The echinocandin class compounds of the invention can be formulated with an aryl amido C8-C10 fatty acid, or salt thereof, as described in U.S. Pat. No. 8,110,547, incorporated herein by reference. For example, a formulation of the invention can include (i) N-[8-(2-hydroxybenzoyl)amino] caprylic acid (also known as "NAC"), and salts (SNAC) thereof, including its sodium salt; (ii) 8-(N-2-hydroxy-4-methoxybenzoyl)-aminocaprylic acid (also known as "4-MOAC"), and salts thereof, including its sodium salt; (iii) N-(8-[2-hydroxybenzoyl]-amino)decanoic acid (also known as "NAD"), and salts (SNAD) thereof, including its sodium salt; (iv) N-(8-[2-hydroxy-5-chlorobenzoyl]-amino) octanoic acid (also known as "5-CNAC"), and salts thereof, including its sodium salt; (iv) 4-[(2-hydroxy-4-chlorobenzoyl)amino]butanoate (also known as "4-CNAB"), and salts thereof, including its sodium salt, or mixtures thereof.

The echinocandin class compounds of the invention can be formulated using a transient permeability enhancer (TPE) system as described in U.S. Pat. No. 8,241,670 and U.S. Patent Publication Nos. 2012/0009229, 2010/0105627, 2011/0257095, and 2011/0311621, each of which is incorporated herein by reference. For example, a formulation of the invention can be prepared by (i) by combining the echinocandin class compound with a fatty acid salt (e.g., sodium octanoate, sodium decanoate, sodium dodecanoate, or combinations thereof) in water to form an aqueous solution; (ii) lyophilizing the aqueous solution to produce a lyophilizate; and (iii) suspending the lyophilizate in a hydrophobic medium (e.g., aliphatic molecules, cyclic molecules, di and tri glycerides of long chain fatty acids, di and tri glycerides of medium chain fatty acids, mineral oil, paraffin, fatty acid distearate (e.g., 2-oleoyl-distearate), mono ethylene glycol distearate, cholesterol esters of fatty acids, aromatic molecules (e.g., benzyl benzolate), or combinations thereof) to produce a suspension. The suspension can optionally include a lecithin, a bile salt, medium chain fatty acid salts, triglycerides, diglycerides, castor oil, and/or a non-ionic detergent (e.g., cremophore, pegylated ethers, solid HS15, poloxamer, sorbitan fatty acid esters, glyceryl tri/mono caprylates, castor oil, triglycerides). The therapeutic composition can further include linear alcohols, branched alcohols, cyclic alcohols and combination thereof. For example, the echinocandin class compound as the sodium octanoate salt as a lyophilizate suspended in a medium including glycerol monocaprylate, glyceryl tricaprylate, castor oil, and/or tween 80. The composition can be formulated as a dry blend, optionally in a capsule or form of a tablet.

The echinocandin class compounds of the invention can be formulated with an aromatic alcohol as described in U.S. Pat. No. 7,303,762 and U.S. Patent Publication Nos. 2006/0223746, 2006/0122097, 20004/0028736, 2002/0015592, and 2012/0017602, each of which are incorporated herein by reference. Aromatic alcohols useful as absorption enhancers in formulations of the invention can include hydrophilic molecules containing at least one aromatic ring and at least one hydroxyl group. Exemplary aromatic alcohols that can be used in the formulations of the invention include phenoxyethanol, benzyl alcohol, phenyl ethanol, and derivatives thereof in which one or more ring protons is substituted by one or more halogen atoms, $C_{1-4}$ alkyl, $C_{1-4}$ alkoxy, $C_{1-4}$ alkylthio or $C_{2-4}$ alkenyl groups. Aromatic alcohols useful in the formulations of the invention include, without limitation, butylated hydroxyl toluene, butylated hydroxyl anisole, propyl gallate, and analogues thereof. The formulation can optionally include an amphiphile, such as polyoxyethylene-containing surfactants with a high HLB such as polyoxyethylene 40 monostearate, PEG200, PEG 300, PEG 400, partial glycerides (i.e., a combination of glycerol, mono-glycerides, and diglycerides), polyoxyethylene 20 cetyl ether, polysorbate 80; block co-polymers such as Lutrol F68; bile salts such as chelate, glycholate, deoxycholate, glycodeoxycholate, chenodeoxycholate, taurodeoxycholate, ursodeoxycholate and fusidate; or amphiphilic polymers such as polyvinyl pyrrolidone. The formulation can further include one or more solubilizers capable of increasing the solubility of aromatic absorption enhancer, such as biguanide, monoglycerides, or a linear alcohol (e.g., ethanol). The formulation can include from 5-85%, 10-85%, 25-85%, 15-70%, or 20-60% (w/w) aromatic alcohol. The formulation can be included in a dosage form that is enteric coated, and/or formulated as a microdispersion in a capsule.

The echinocandin class compounds of the invention can be formulated with an omega-3 fatty acid as described in U.S. Patent Publication No. 2007/0087957, incorporated herein by reference. Omega-3 fatty acids useful as absorption enhancers in formulations of the invention can be selected from (i) DHA (an omega-3, polyunsaturated, 22-carbon fatty acid also referred to as 4,7,10,13,16,19-docosahexaenoic acid); (ii) alpha-linolenic acid (9,12,15-octadecatrienoic acid); (iii) stearidonic acid (6, 9, 12, 15-octadecatetraenoic acid); (iv) eicosatrienoic acid (ETA; 11,14, 17-eicosatrienoic acid); (v) eicsoatetraenoic acid (8,11,14, 17-eicosatetraenoic acid); (vi) eicosapentaenoic acid (EPA; 5,8,11,14,17-eicosapentaenoic acid); (vii) eicosahexaenoic acid (5,7,9,11,14,17-eicosahexaenoic acid); (viii) docosapentaenoic acid (DPA; 7,10,13,16,19-docosapenatenoic acid); (ix) tetracosahexaenoic acid (6,9,12,15,18,21-tetracosahexaenoic acid); and mixtures thereof. The formulation can include from 5-85%, 10-85%, 25-85%, 15-70%, or 20-60% (w/w) omega-3 fatty acid. The formulation can further include a bile acid, such as cholic acid, chenodeoxycholic acid, taurocholic acid, taurochenodeoxycholic acid, glycocheocholic acid, 3-13 monohydroxy cholic acid, lithocholic acid, 3-α hydroxyl-12-ketocholic acid, 3-0 hydroxy-12-ketocholic acid, 12-α-3-β-dihydrocholic acid, ursodesooxycholic acid, or salts thereof.

The echinocandin class compounds of the invention can be formulated with an alkyl saccharide or ester saccharide as described in U.S. Pat. No. 5,661,130, or in U.S. Patent Publication Nos. 2008/0200418, 2006/0046962, 2006/0045868, 2006/0024577, 2007/0298010, 2010/0209485, and 2008/0194461, each of which is incorporated herein by reference. Alkyl saccharides or ester saccharides useful as absorption enhancers in formulations of the invention can be selected from dodecyl maltoside, tridecyl maltoside, tetradecyl maltoside, sucrose mono-dodecanoate, sucrose mono-tridecanoate, sucrose mono-tetradecanoate, and mixtures thereof. The formulation can include from 0.1-1.5%, 0.5-5%, 0.75-6.5%, 1.5-6.5%, or 2-10% (w/w) alkyl saccharide or ester saccharide. The weight ratio of drug:absorption enhancer can be from 1:0.5 to 1:8.

The echinocandin class compounds of the invention can be formulated with (i) an absorption enhancer selected from acyl carnitines, acyl cholines, acyl aminoacids, phospholipids, and bile acids, or their salts; and (ii) a pH lowering agent as described in U.S. Pat. Nos. 8,093,207 and 6,086,918, each of which is incorporated herein by reference. The absorption enhancer can be selected from lauroylcarnitine, myristoylcarnitine, palmitoylcarnitine, lauroylcholine, myristoylcholine, palmitoylcholine, hexadecyllysine, N-acylphenylalanine, N-acylglycine, and mixtures thereof. For example, the formulation can include acyl carnitine and a second absorption enhancer selected from phospholipids, bile acids, or salts thereof. The pH-lowering agent can be selected from citric acid, tartaric acid and amino acids. The formulation can include from 1-15%, 5-25%, 1.5-9.5%, 15-25%, or 8-30% (w/w) absorption enhancer. The weight ratio of the pH-lowering agent to the absorption enhancer can be between 3:1 and 20:1. Desirably, the pH-lowering agent is present in an amount such that if a pharmaceutical composition in unit dosage form were added to ten milliliters of 0.1M aqueous sodium bicarbonate solution, the amount would be sufficient to lower the pH of the solution to no higher than 5.5. The weigh ratio of drug:absorption enhancer can be 0.5:1 to 1:20. The formulation can further include bile acids, cationic and/or anionic cholesterol derivatives, monoglycerides, and/or linear alcohols (e.g., ethanol).

The echinocandin class compounds of the invention can be formulated as a solid oral dosage form including (i) from about 0.5 to 70% (e.g., 0.5 to 20%, 10 to 40%, 20 to 50%, or 30 to 70%) (w/w) echinocandin class compound, or a pharmaceutically acceptable salt thereof, and (ii) from about 5 to 80% (e.g., 5 to 20%, 10 to 30%, 15 to 40%, or 20 to 80%) (w/w) glyceride. The glyceride can be any glyceride described herein, but preferably is selected from a mono- or di-glyceride of capric acid, a mono- or di-glyceride of caprylic acid, or a mixture of mono- and di-glycerides of caprylic and capric acids, or a mixture of two or more thereof. The solid oral dosage form can further include a surfactant and/or oil (e.g., a non-ionic surfactant, such as ethoxylated castor oil; ethoxylated derivatives of $C_{5-29}$ mono-glycerides; polyoxyethylene derivatives of $C_{15-60}$ diglycerides having 1 to 90 oxyethylene (POE) repeating units; $C_{8-96}$ ethoxylated fatty esters; $C_{14-130}$ sucrose fatty esters; and polyoxyethylene derivatives of $C_{20-130}$ sorbitol and sorbitan monoesters and triesters having 0 to 90 POE repeating units, or an anionic surfactant, such as salts of $C_{8-32}$ fatty acids; deoxycholate salts; ursodeoxycholate salts; taurocholate salts; and sodium lauryl sulfate). In the solid oral dosage forms the echinocandin class compound, or a pharmaceutically acceptable salt thereof, is in the form of solid uniformly dispersed particles having a mean particle size of from about 1 nm to about 1 mm. The solid dosage forms can be prepared using the methods described in U.S. Pat. No. 7,670,626, incorporated herein by reference. The composition can further include a biocompatible oil.

The echinocandin class compounds of the invention can be formulated a particle including the echinocandin class compound, wherein the particle has an effective average diameter of less than about 2000 nm (i.e., as determined using light scattering methods) as described in U.S. Patent Publication No. 2009/0238867, incorporated herein by reference. The particulate formulation can include at least one surface stabilizer absorbed on a surface of the particle (e.g., a surface stabilizer selected from a non-ionic surface stabilizers, ionic surface stabilizers, cationic surface stabilizers, zwitterionic surface stabilizers, and anionic surface stabilizers, including those identified in U.S. Patent Publication No. 2009/0238867, incorporated herein by reference.

Echinocandin class of compounds can be formulated with one or more ion pairing agents (e.g., cationic or anionic agents) for oral delivery. For example compound 22 can be modified using anionic groups of citric acid or fatty acids or bile acids to form an ion-paired composition. The resulting complex can be formulated into biodegradable nano particles by spontaneous emulsion and solvent diffusion methods. (see Yoo et al., J. Pharmaceut. Sci. 90:194, 2001; and Quintanar-Guerrero et al., Pharmaceut. Res. 14:119, 1997). Ion-paired formulations can be prepared from organic acids, such as acid salts of amino acids, or acid addition salts (e.g., acetic, lactic, palmoic, maleic, citric, cholic acid, capric acid, caprylic acid, lauric acid, glutaric, glucuronic, glyceric, glycocolic, glyoxylic, isocitric, isovaleric, lactic, malic, oxalo acetic, oxalosuccinic, propionic, pyruvic, ascorbic, succinic, benzoic, palmitic, suberic, salicylic, tartaric, methanesulfonic, toluenesulfonic, or trifluoroacetic acid addition salts). In certain preferred formulations, the ion-paired composition includes an absorption enhancer, such as citric, capric, caprylic, phopsholipids and cholic acid addition salts.

Transdermal Administration

Compounds and formulations of the invention can be administered transdermally. To increase the rate at which the compound penetrates through the skin, the compound can be administered with a physical penetration enhancer or a chemical penetration enhancer. Physical enhancement of skin permeation includes, for example, electrophoretic techniques, such as iontophoresis or electroporation (see U.S. Pat. Nos. 6,148,232; 6,597,946; 6,611,706; 6,708,060; 6,711,435; and 6,275,728, each of which is incorporated herein by reference), including radiofrequency cell ablation technology to enable the creation of microchannels on the skin surface (see Levin et al., Pharmaceutical Research, 22:550 (2005)). Chemical enhancers can be administered along with the compound to increase the permeability of the stratum corneum, and thereby provide for enhanced penetration of the compound through the skin.

Formulations for Injection

For use in the dosing regiments of the invention, echinocandin class compounds can be formulated for intravenous infusion, bolus injection, and/or subcutaneous administration. Such formulations can optionally include a bulking agent and, optionally include a surfactant excipient packaged in a vial. The formulations are optionally reconstitutable dry formulations (e.g., freeze dried dosage forms). For example, echinocandin class compounds can be formulated for injection in saline, optionally with 0.1 to 1% (w/w) polysorbate surfactant, added as a surfactant agent. For example, the echinocandin class compounds can be formulated for injection in sterile water or aqueous buffer (e.g., phosphate, acetate, lactate, tatarate, citrate, among others). For example, compound 22 can be packaged in a infusion bag containing 5% dextrose or saline solution, or prepackaged as a solid or liquid concentrate for reconstitution prior to administration.

Alternatively, the echinocandin class compounds can be incorporated into pharmaceutically-acceptable nanoparticle, nanosphere, or nanocapsule formulations. Nanocapsules can generally entrap compounds in a stable and reproducible way. To avoid side effects due to intracellular polymeric overloading, ultrafine particles (sized around 0.1 μm) can be designed using polymers able to be degraded in vivo (e.g., biodegradable polyalkyl-cyanoacrylate nanoparticles). Such particles are described in the prior art (see, for example, U.S. Pat. No. 5,145,684, incorporated herein by reference). The nanoparticulate formulations typically are between about 5 nM and 400 nM across the largest dimension of the structure and can be formed using a natural or artificial polymer. The polymers may be biodegradable, bioresorbable, or bioerodable polymers and can include, without limitation, albumin, collagen, gelatin and prolamines such as zein, polysaccharides such as alginate, cellulose derivatives and polyhydroxyalkanoates such as polyhydroxybutyrate aliphatic polyesters; poly(glycolic acid) and/or copolymers thereof (e.g., poly(glycolide trimethylene carbonate); poly(caprolactone glycolide); poly(lactic acid) and/or isomers thereof (e.g., poly-L(lactic acid) and/or poly-D (lactic acid) and/or copolymers thereof (e.g., DL-PLA), with and without additives (e.g., calcium phosphate glass), and/or other copolymers (e.g., poly(caprolactone lactide), poly(lactide glycolide), poly(lactic acid ethylene glycol); poly(ethylene glycol) (in its various weights, i.e. 2000 D, 4000 D, 6000 D, 8000 D, etc.); poly(ethylene glycol) diacrylate; poly(lactide); polyalkylene succinate; polybutylene diglycolate; polyhydroxybutyrate (PHB); polyhydroxyvalerate (PHV); polyhydroxybutyrate/polyhydroxyvalerate copolymer (PHB/PHV); poly(hydroxybutyrate-co-valerate); polyhydroxyalkaoates (PHA); polycaprolactone; poly(caprolactone-polyethylene glycol) copolymer; poly(valerolactone); polyanhydrides; poly(orthoesters) and/or blends with polyanhydrides; poly(anhydride-co-imide); polycarbonates (aliphatic); poly(hydroxyl-esters); polydioxanone; polyanhydrides; polyanhydride esters; polycyanoacrylates; poly(alkyl 2-cyanoacrylates); poly(amino acids); poly(phosphazenes); poly(propylene fumarate); poly(propylene fumarate-co-ethylene glycol); poly(fumarate anhydrides); fibrinogen; fibrin; gelatin; cellulose and/or cellulose derivatives and/or cellulosic polymers (e.g., cellulose acetate, cellulose acetate butyrate, cellulose butyrate, cellulose ethers, cellulose nitrate, cellulose propionate, cellophane); chitosan and/or chitosan derivatives (e.g., chitosan NOCC, chitosan NOOC-G); alginate; polysaccharides; starch; amylase; collagen; polycarboxylic acids; poly(ethyl ester-co-carboxylate carbonate) (and/or other tyrosine derived polycarbonates); poly (iminocarbonate); poly(BPA-iminocarbonate); poly(trimethylene carbonate); poly(iminocarbonate-amide) copolymers and/or other pseudo-poly(amino acids); poly (ethylene glycol); poly(ethylene oxide); poly(ethylene oxide)/poly(butylene terephthalate) copolymer; poly(epsilon-caprolactone-dimethyltrimethylene carbonate); poly(ester amide); poly(amino acids) and conventional synthetic polymers thereof; poly(alkylene oxalates); poly(alkylcarbonate); poly(adipic anhydride); nylon copolyamides; NO-carboxymethyl chitosan NOCC); carboxymethyl cellulose; copoly(ether-esters) (e.g., PEO/PLA dextrans); polyketals; biodegradable polyethers; biodegradable polyesters; polydihydropyrans; polydepsipeptides; polyarylates (L-tyrosine-derived) and/or free acid polyarylates; polyamides (e.g., Nylon 66, polycaprolactam); poly(propylene fumarate-co-ethylene glycol) (e.g., fumarate anhydrides); hyaluronates; poly-p-dioxanone; polypeptides and proteins; polyphosphoester; polyphosphoester urethane; polysaccharides; pseudo-poly(amino acids); starch; terpolymer; (copolymers of glycolide, lactide, or dimethyltrimethylene carbonate); rayon; rayon triacetate; latex; and/pr copolymers, blends, and/or composites of above. The nanoparticulate formulations can be used for controlled, delayed, or sustained delivery of an echinocandin class compound administered to a subject using a dosing regimen of the invention (see, for example, Chan et al., Biomaterials, 30:1627, 2009; and Gupta et al., Int. J. Res. Pharm. Sci. 1:163, 2010).

The formulations for injection can be administered, without limitation, intravenously, intramuscularly, or subcutaneously.

The formulations for injection can be stored in single unit or multi-dose containers, for example, sealed ampules, pre-filled syringes, or vials, as an aqueous solution or as a lyophilized formulation (i.e., freeze dried) for reconstitution. The containers may any available containers in the art and filled using conventional methods. Optionally, the formulation may be included in an injection pen device (or a cartridge which fits into a pen device), such as those available in the art (see, e.g., U.S. Pat. No. 5,370,629), which are suitable for injection delivery of the formulation. The formulations for injection can be administered using pen-injector devices, such as EasyJect®, GONAL-F® Pen, Humaject®, Novopen®, B-D® Pen, AutoPen®, Follistim®-Pen, Puregon®-Pen and OptiPen®, or Ypsomed SevoPens.

Therapy

The treatment regimens and pharmaceutical compositions described herein can be used to treat or prevent fungal infections.

The fungal infection being treated can be an infection selected from tinea capitis, tinea corporis, tinea pedis, onychomycosis, perionychomycosis, *pityriasis versicolor*, oral thrush, vaginal candidosis, respiratory tract candidosis, biliary candidosis, eosophageal candidosis, urinary tract candidosis, systemic candidosis, mucocutaneous candidosis, aspergillosis, mucormycosis, paracoccidioidomycosis, North American blastomycosis, histoplasmosis, coccidioidomycosis, sporotrichosis, fungal sinusitis, or chronic sinusitis. For example, the infection being treated can be an infection by *Candida albicans, C. parapsilosis, C. glabrata, C. guilliermondii, C. krusei, C. lusitaniae, C. tropicalis, Aspergillus fumigatus, A. flavus, A. terreus, A. niger, A. candidus, A. clavatus*, or *A. ochraceus*.

The treatment regimens and pharmaceutical compositions described herein can be administered intravenously, subcutaneously, topically, orally, or by any other route described herein. In one approach, a loading-dose of echinocandin class compound is administered to a subject in need thereof, followed by maintenance dosing administered orally.

The treatment regimens and pharmaceutical compositions described herein can be administered to prevent a fungal infection in a subject in need thereof. For example, subjects may receive prophylaxis treatment while being prepared for an invasive medical procedure (e.g., preparing for surgery, such as receiving a transplant, stem cell therapy, a graft, a prosthesis, receiving long-term or frequent intravenous catheterization, or receiving treatment in an intensive care unit), in immunocompromised subjects (e.g., subjects with cancer, with HIV/AIDS, or taking immunosuppressive agents), or in subjects undergoing long term antibiotic therapy. Alternatively, the treatment regimens and pharmaceutical compositions described herein can be administered to treat a blood stream infection or invasive infection (e.g., lung, kidney, or liver infections) in a subject.

The following examples are put forth so as to provide those of ordinary skill in the art with a complete disclosure and description of how the methods and compounds claimed herein are performed, made, and evaluated, and are intended to be purely exemplary of the invention and are not intended to be limiting.

Example 1. Pharmacokinetics Following Intravenous Administration in Beagle Dogs Echinocandin class compounds were administered to beagle dogs weighing approximately 6-10 kg. Each compound was dosed at 1.4 mg/kg in aqueous saline (with or without 0.5% Tween) over course of 1-10 minutes. Diphenhydramine was kept on hand in case the dogs demonstrated a histamine response. The dogs were fasted at least 12 hours prior to each dosing and offered food after the 4-hour blood sample was taken; water was withheld for 1 hour prior to and 4 hours following each dosing event. The dose for each animal was based on its most recent body weight. The test article was injected intravenously via a catheter placed in the cephalic vein as a slow bolus.

Blood was collected via the jugular vein. All blood samples (1 mL each) were collected into $K_3$EDTA tubes. Following blood collection, the samples were immediately inverted several times and were held on wet ice pending centrifugation. The samples were centrifuged within 30 minutes of collection under refrigeration (~5° C. for 10 minutes at 2000 g) to obtain plasma. The plasma was frozen immediately on dry ice after separation. The plasma samples were stored at approximately ~70° C. until analysis.

Plasma (100 µL) was precipitated with 400 µL of 0.1% formic acid in acetonitrile containing the internal standard (100 ng/mL pneumocandin). The samples were then capped and vortexed for about 30 seconds followed by centrifugation at 14,000 rpm at room temperature for 10 minutes. Following centrifugation 200 µL of supernatant was transferred to plastic autosampler vials containing 200 µL of 0.1% formic acid in water and vortexed. Samples were then analyzed by LCMSMS.

All pharmacokinetic calculations were performed using WinNonlin version 4.1 (Pharsight Corp) by noncompartmental analysis. The results are provided in Table 1, below.

TABLE 1

PK Values following intravenous dosing in dogs.

| Compound | AUC (hr · ng/mL) | Cmax (ng/mL) | $T_{1/2}$ (Hr) | Volume of Distribution (mL/kg) | Mean clearance (mL/min/kg) |
|---|---|---|---|---|---|
| Anidulafungin | 27833 | 3230 | 11.6 | 779 | 0.785 |
| Compound 22 | 48700 | 1570 | 53.1 | 1360 | 0.301 |
| Compound 26 | 67167 | 4080 | 33.7 | 627 | 0.219 |
| Compound 37 | 46200 | 2660 | 27.6 | 874 | 0.365 |
| Compound 19 | 96100 | 7700 | 18.9 | 331 | 0.202 |
| Compound 21 | 113000 | 6740 | 28.9 | 361 | 0.145 |
| Compound 39 | 50800 | 3630 | 21.0 | 687 | 0.377 |

Example 2. Formulation for Oral Administration

The following formulations can be used in the methods, kits, and compositions of the invention.

Exemplary oral formulations of the invention are described in Table 2.

TABLE 2

| Formulation | Composition | Concentration |
|---|---|---|
| Formulation 1 | Echinocandin class compound | 10.0 mg/mL |
|  | Dodecyl Maltoside | 3% (w/w) |
|  | Tween 20 | 1% (w/w) |
|  | Saline | 96% (w/w) |
| Formulation 2 (emulsion) | Echinocandin class compound | 10.0 mg/mL |
|  | Labrasol ® | 40% (w/w) |
|  | Plurol Oleique | 10% (w/w) |
|  | Labrafac ® | 6.25% (w/w) |
|  | Propylene glycol | 6.25% (w/w) |
|  | Water | 37.5% (w/w) |
| Formulation 3 | Echinocandin class compound | 10.0 mg/mL |
|  | Mono glyceryl decanoate | 4% (w/w) |
|  | Tricparin | 4% (w/w) |
|  | Tween 20 | 1.5% (w/w) |
|  | Tween 80 | 0-0.8% (w/w) |
|  | NaOAc buffer (0.1M, pH 5-6) | 90.5% (w/w) |
| Formulation 4 | Echinocandin class compound | 10.0 mg/mL |
|  | Laureth 12 | 6.07% (w/w) |
|  | Tween 20 | 1.16% (w/w) |
|  | Saline | 92.8% (w/w) |
| Formulation 5 | Echinocandin class compound | 10.0 mg/mL |
|  | Sodium caprate | 3% (w/w) |
|  | Sodium laurate | 3% (w/w) |
|  | Phosphate buffer (0.1M, pH 7.4) | 94% (w/w) |

TABLE 2-continued

| Formulation | Composition | Concentration |
|---|---|---|
| Formulation 6 | Echinocandin class compound | 7.5 mg/mL |
|  | Chitosan (low MW) | 3% (w/w) |
|  | NaOAc buffer (0.1M, pH 5-6) | 90.5% (w/w) |
| Formulation 7 | Echinocandin class compound | 10.0 mg/mL |
|  | DL Palmitoyl carnitine | 5% (w/w) |
|  | NaOAc buffer (0.1M, pH 5-6) | 95% (w/w) |
| Formulation 8 | Echinocandin class compound | 10.0 mg/mL |
|  | DPPS | 5% (w/w) |
|  | NaOAc buffer (0.1M, pH 5-6) | 95% (w/w) |
| Formulation 9 | Echinocandin class compound | 2.2% (w/w) |
|  | Propylene glycol | 19.3% (w/w) |
|  | Peceol | 67.6% (w/w) |
|  | DSPE-PEG2000 | 13% (w/w) |
| Formulation 10 | Echinocandin class compound | 2.2% (w/w) |
|  | Capmul MCM C8, EP | 25.5% (w/w) |
|  | Glycerol | 55.7% (w/w) |
|  | Propylene glycol | 15.3% (w/w) |
| Formulation 11 (saline) | Echinocandin class compound | 10.0 mg/mL |
|  | Tween 20 | 0-0.5% (w/w) |
|  | Saline | 99.5% (w/w) |
| Formulation 12 | Echinocandin class compound | 11.4 mg/mL |
|  | Sodium caprate | 6% (w/w) |
|  | Phosphate buffer (0.1M, pH 7.8) | 94% (w/w) |
| Formulation 13 (liquid filled gel) | Echinocandin class compound | 1.9% (w/w) |
|  | Propylene glycol | 18.8% (w/w) |
|  | Peceol | 75.1% (w/w) |
|  | DSPE-PEG2000 | 4.2% (w/w) |
| Formulation 14 (gelfilled dry blend) | Echinocandin class compound | 15% (w/w) |
|  | DL Palmitoyl carnitine | 75% (w/w) |
|  | Sodium citrate | 10% (w/w) |
| Formulation 15 (liquid filled gel) | Echinocandin class compound | 4.3% (w/w) |
|  | Capric acid | 32.8% (w/w) |
|  | Propylene glycol | 18.1% (w/w) |
|  | Trolamine | 31.8% (w/w) |
|  | PEG200 | 11.4% (w/w) |
| Formulation 16 (immediate release tablet) | Echinocandin class compound | 17.7% (w/w) |
|  | Sodium caprate | 29.9% (w/w) |
|  | Sodium laurate | 29.4% (w/w) |
|  | Mannitol | 17.7% (w/w) |
|  | Explotab | 4.8% (w/w) |
|  | Na Stearyl Fumarate | 0.4% (w/w) |
| Formulation 17 (immediate release tablet) | Echinocandin class compound | 17.2% (w/w) |
|  | DL Palmitoyl carnitine | 60.1% (w/w) |
|  | Mannitol | 17.3% (w/w) |
|  | Explotab | 5.1% (w/w) |
|  | Na Stearyl Fumarate | 0.3% (w/w) |
| Formulation 18 | Echinocandin class compound | 1.5% (w/w) |
|  | Sesame oil | 71.5% (w/w) |
|  | Glyceryl monostearate | 1.5% (w/w) |
|  | Tween 20 | 0.8% (w/w) |
|  | NaOAc, 0.1M, pH 5-6 | 24.8% (w/w) |
| Formulation 19 | Echinocandin class compound | 1.0% (w/w) |
|  | Citric acid | 5.0% (w/w) |
|  | Sterile water | 96.0% (w/w) |
| Formulation 20 | Echinocandin class compound | 1.0% (w/w) |
|  | PEG400 | 99.0% (w/w) |

Example 3. Pharmacokinetics Following Oral Administration in Beagle Dogs

Echinocandin class compounds were administered to beagle dogs weighing approximately 6-10 kg. Each animal received the appropriate prepared test article in a single oral capsule dose at a target dose level of about 7-10 mg/kg. Immediately after dosing, each animal was offered 20 mL-30 mL of water orally (Groups 1-4) or 30 mL of water orally to assist in swallowing the capsule.

Animals were treated and blood samples were drawn and analyzed as provided in Example 1.

The bioavailability of each oral dose formulation was estimated by comparison to intravenous plasma concentration data in dogs from Example 1. The results provided in Table 3 show the oral bioavailability for the echinocandin class compound in saline (formulation 11), and the improvement over saline with the use of a formulation of the invention.

TABLE 3

Oral Dosing Results[1]

| Compound | % BA in saline[2] | Formulation | Improvement[3] (% BA) |
|---|---|---|---|
| Anidulafungin | 7.80% | 5 | 2.1 (16.5%) |
|  |  | 1 | 1.8 (14.3%) |
|  |  | 3 | 1.3 (9.80%) |
|  |  | 4 | NI[4] |
|  |  | 2 | NI |
|  |  | 6 | NI |
| Compound 22 | 3.50% | 5 | 3.5 (12.3%) |
|  |  | 1 | 2.3 (8.21%) |
|  |  | 3 | 2.8 (9.76%) |
|  |  | 7 | 3.5 (12.2%) |
|  |  | 8 | NI |
|  |  | 9 | NI |
|  |  | 10 | NI |
|  |  | 16 | 1.5 (5.50%) |
|  |  | 17 | 3.3 (11.8%) |
|  |  | 12 | NI |
|  |  | 13 | 2.5 (8.80%) |
|  |  | 14 | 4.3 (15.0%) |
|  |  | 15 | 3.8 (13.4%) |
| Compound 26 | NA[5] | 6 | NI |
|  |  | 5 | NI |
|  |  | 7 | NI |
| Compound 37 | NA[5] | 5 | NI |
|  |  | 1 | NI |
|  |  | 3 | NI |
|  |  | 7 | NI |
| Compound 19 | 5.74% | 5 | NI |
|  |  | 1 | NI |
| Compound 21 | 4.70% | 5 | NI |
|  |  | 1 | 1.3 (6.42%) |
|  |  | 7 | NI |
| Compound 39 | 5.15% | 5 | NI |
|  |  | 1 | NI |

[1]All percent oral bioavailabilities are calculated from AUC data.
[2]Percent oral bioavailability in formulation 11.
[3]Improvement reported as the ratio of the percent oral bioavailability for a formulation divided by the oral bioavailability when formulated in saline.
[4]NI = no improvement in oral bioavailability in comparison to saline.
[5]NA = not available. Improvement evaluated based on observed oral bioavailability for other compounds of Table 3 in saline.

Improvements in oral bioavailability were observed for formulations including fatty acids or salts thereof (formulations 5, 14, 15, and 16), glycerides (formulations 3 and 13), acyl carnitines (formulations 7, 14, and 17), alkyl saccharides (formulation 1), and pegylated phospholipids (formulation 13).

The largest improvements in oral bioavailability were observed for anidulafungin and compound 22.

Example 4. Dissolution Profile of Tableted Formulation 17

A dissolution study of the tablet of formulation 17 was performed using 500 mL of 100 mM Acetate Buffer pH 5.2 as the medium. The method utilized Apparatus 2 with a paddle speed of 50 rpm, a tablet sinker, and the run time was 60 minutes. After the dissolution was complete, the samples were analyzed for compound 22 content using HPLC. The HPLC method was a gradient method using an Agilent Zorbax Bonus-RP column (250×4.6 mm) (column temperature of 60° C., wavelength of 300 nm, with Mobile Phase A=33 mM sodium pentanesulfonate pH 4.0 and Mobile Phase B=acetonitrile). The samples were injected neat with an injection volume of 15 µL.

The results of the dissolution study are provided in Table 4.

TABLE 4

| Sample Time (Minutes) | % Compound 22 Dissolved |
|---|---|
| 5 | 23 |
| 10 | 48 |
| 15 | 62 |
| 30 | 93 |
| 45 | 96 |
| 60 | 97 |

The tablet of formulation 17 has an immediate release profile (i.e., over 80% dissolved within 30 minutes). Thus, formulation 17 allows for the simultaneous release of permeation enhancing additive and compound 22. The substantially simultaneous release of both the active and excipients is necessary to achieve an increase in oral bioavailability.

Example 5. Aqueous Formulation of Compound 22 for Injection

The solubility of compound 22 was measured in aqueous buffers of varying pH to assess this compound's suitability for formulation in an aqueous carrier for administration by injection (e.g., intravenous bolus, intravenous infusion, subcutaneous, or intramuscular injection).

The results are provided in Table 5 (below) along with anidulafungin as a comparison. Compound 22 was found to have dramatically greater aqueous solubility than anidulafungin in a variety of aqueous mediums.

TABLE 5

| | Solubility (mg/mL)[1] | |
|---|---|---|
| Aqueous Medium | Anidulafungin | Compound 22 |
| Sterile Water for injection | <0.01 | >142 |
| 90% Water:10% glycerol | <0.01 | >102.3 |
| Acetate buffer (0.01M, pH 4.5) | <0.01 | >145 |
| Acetate buffer (0.01M, pH 5.5) | <0.01 | >141 |
| Tris buffer (0.01M, pH 8.5) | <0.01 | >138 |

[1]Solubility in mg/mL of salt free equivalent of compound 22. All measurements made at ambient temperature for acetate salt. Point of saturation was not achieved in these measurements for compound 22.

Example 6. Intravenous Infusion of Compound 22

Compound 22 can be supplied in a single-use vial of sterile lyophilized material. Compound 22 can be reconstituted in sterile water and subsequently diluted with 5% dextrose injection or 0.9% sodium chloride injection, USP (normal saline) for infusion into a subject.

A vial containing a quantity of compound 22 can be reconstituted with a volume of sterile water, or another suitable aqueous carrier, to provide a concentration of about 3.3 mg/mL.

Content of the reconstituted vial(s) can be transferred into an appropriately sized IV infusion bag containing either 5% dextrose injection, USP or 0.45% to 0.9% sodium chloride.

Exemplary doses and volumes are provided in Table 6 (below)

TABLE 6

| Dose (mg) | Reconstituted volume (mL) | Infusion volume (mL) | Total infusion volume (mL) | Infusion solution concentration (mg/mL) |
|---|---|---|---|---|
| 50 | 15 | 50 | 65 | 0.77 |
| 100 | 30 | 100 | 130 | 0.77 |
| 200 | 60 | 200 | 260 | 0.77 |

Example 7. Stability of Compound 22 and Anidulafungin in Various Mammalian Plasmas and in PBS Stock solutions of compound 22 and anidulafungin were prepared in DMSO at a concentration of 1 mg/mL. Plasma samples were prepared by mixing plasma with 10% volume of 1 M sodium phosphate, pH 7.4, to minimize pH fluctuation, and stock solution to produce plasma samples containing approximately 10,000 ng/mL compound 22 or anidulafungin. For the stability experiments in PBS buffer, plasma was replaced with phosphate buffered saline, pH 7.4. The DMSO concentration was 1% in the final incubation. Multiple individual aliquots (0.5 mL each) were prepared, capped, and incubated at 37° C. At each stability time point, the reaction was stopped by removing the sample from the incubator and adding 0.5 mL of acetonitrile containing internal standard. Samples were centrifuged for approximately 5 minutes at 10000 rpm to precipitate the proteins. Stability was measured in five different matrices (i.e. rat plasma, dog plasma, monkey plasma, human plasma, and PBS). An aliquot (100 µL) of supernatant of each sample was assayed by HPLC. The percentage of anidulafungin and compound 22 remaining at each time point was calculated by dividing the peak area ratio at each time point by the peak area ratio at time zero.

TABLE 7

| | Anidulafungin (% remaining) | | | | |
|---|---|---|---|---|---|
| Time (h) | Dog plasma | Human plasma | Monkey plasma | PBS | Rat plasma |
| 0 | 100% | 100% | 100% | 100% | 100% |
| 1 | 100% | 102% | 106% | 100% | 84.3% |
| 2 | 94.8% | 98.0% | 111% | 97.8% | 76.5% |
| 4 | 77.1% | 61.8% | 68.1% | 87.4% | 45.6% |
| 8 | 81.1% | 72.0% | 76.0% | 86.0% | 23.2% |
| 21 | 47.2% | 51.2% | 22.4% | 68.9% | 7.3% |
| 44 | 14.6% | 7.3% | 13.8% | 41.9% | 7.4% |

TABLE 8

Compound 22 (% remaining)

| Time (h) | Dog plasma | Human plasma | Monkey plasma | PBS | Rat plasma |
|---|---|---|---|---|---|
| 0 | 100% | 100% | 100% | 100% | 100% |
| 1 | 97.9% | 98.5% | 109% | 105% | 103% |
| 2 | 107% | 101% | 110% | 103% | 106% |
| 4 | 119% | 125% | 143% | 107% | 138% |
| 8 | 94.0% | 97.5% | 115% | 101% | 99.3% |
| 21 | 87.3% | 95.7% | 104% | 96.3% | 96.5% |
| 44 | 78.6% | 93.3% | 93.5% | 96.1% | 91.2% |

In all test systems (plasma from rat, dog, monkey, human and PBS), compound 22 showed greater stability than anidulafungin. Considering a primary mechanism of clearance for anidulafungin in vivo is chemical degradation, and considering that compound 22 displays slower degradation both in plasma and in buffer, this greater stability of compound 22 in various matrices is likely a contributing factor in the slower clearance observed for this compound. Thus, the increased stability may ultimately enable a less frequent dosing regimen than what is required of echinocandins with less stability.

The stability in plasma observed for compound 22 is necessary, but not sufficient, to permit its use in a dosing regimen in which a therapeutically effective steady state concentration is achieved with less frequent dosing.

Example 8. Pharmacokinetics of Compound 22 and Anidulafungin in Chimpanzee

Figure 16A:
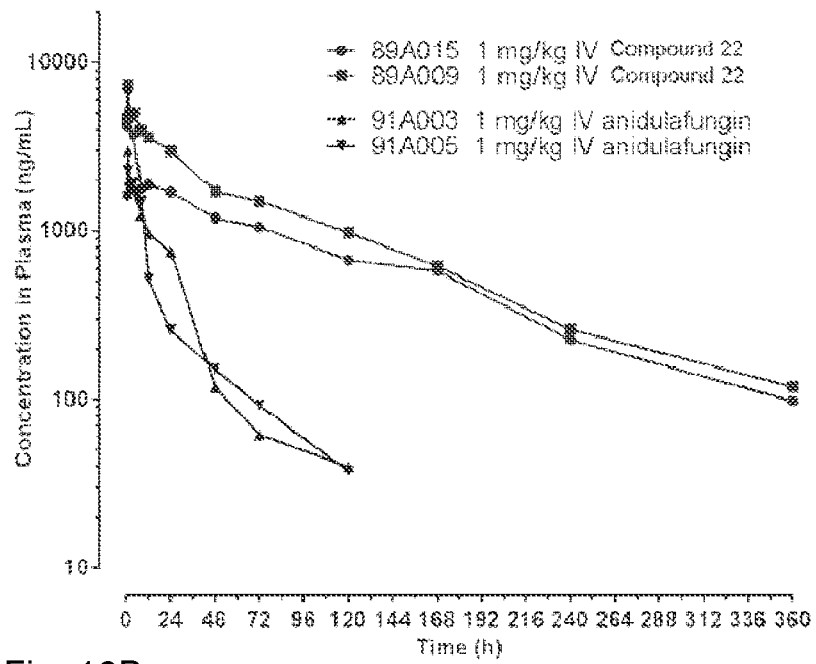
FIGS. 16A and 16B are graphs depicting the pharmacokinetic curves observed in chimpanzees for compound 22 and anidulafungin both administered intravenously (FIG. 16A) and for compound 22 administered orally and anidulafungin administered intravenously (FIG. 16B).
Figure 16B:
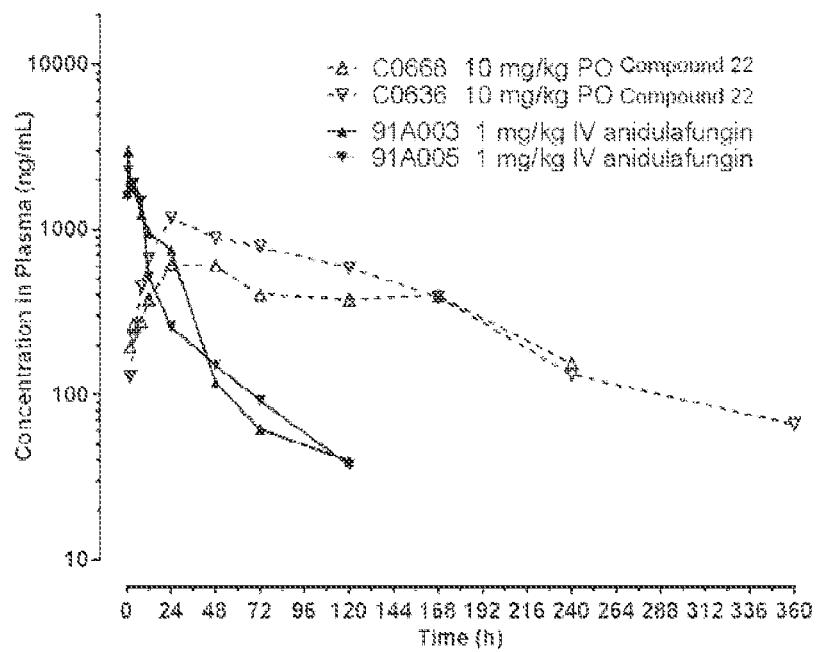
Figure 18:
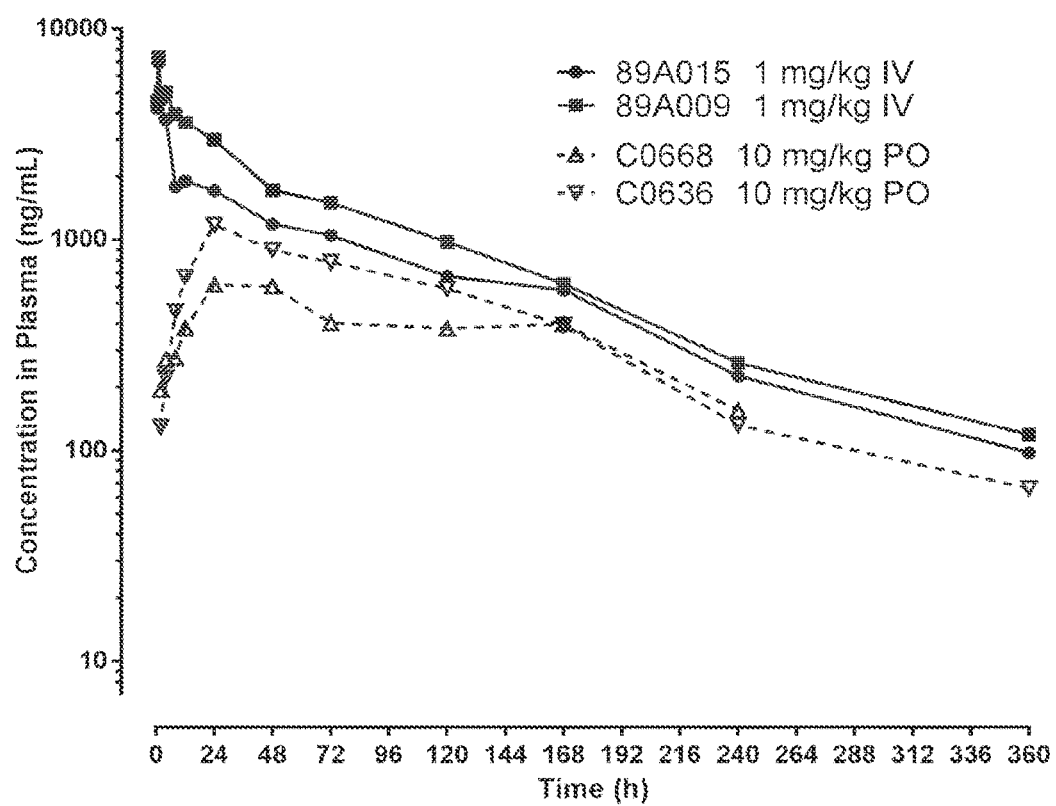
FIG. 18 is a graph depicting the pharmacokinetic curves observed in chimpanzees for compound 22 administered intravenously at 1 mg/kg and compound 22 administered orally at 10 mg/kg.

Pharmacokinetic studies were performed in six adult female chimpanzees. Two chimpanzees received 1-mg/kg IV dose of compound 22 formulated in 5% dextrose (60-minute infusion). Two chimpanzees received 10-mg/kg oral dose of compound 22 formulated in 5% citric acid (oral bolus). Two chimpanzees received 1-mg/kg IV dose of anidulafungin formulated as package label (5% dextrose, 60-minute infusion). Plasma samples were collected from all chimps for 10 days to 22 days. PK curves are depicted in FIGS. 16A, 16B, and 18. All pharmacokinetic calculations were performed using WinNonlin version 4.1 (Pharsight Corp) by noncompartmental analysis. The results are provided in Table 9 and 10, below.

TABLE 9

Compound 22 IV and Oral PK in Chimpanzees

PK parameters (mean of 2 chimps)

| Clearance | 3.4 mL/h/kg |
|---|---|
| Volume of distribution | 0.4 L/kg |
| Plasma half-life | 81 h (IV) |
|  | 99 h (PO) |
| Oral bioavailability | 4.5% |

TABLE 10

Anidulafungin IV PK Data in Chimpanzees

PK parameters (mean of 2 chimps)

| Clearance | 25 mL/h/kg |
|---|---|
| Volume of distribution | 1.1 L/kg |
| Plasma half-life (IV) | 30 h |
| Oral bioavailability | — |

Figure 17A:
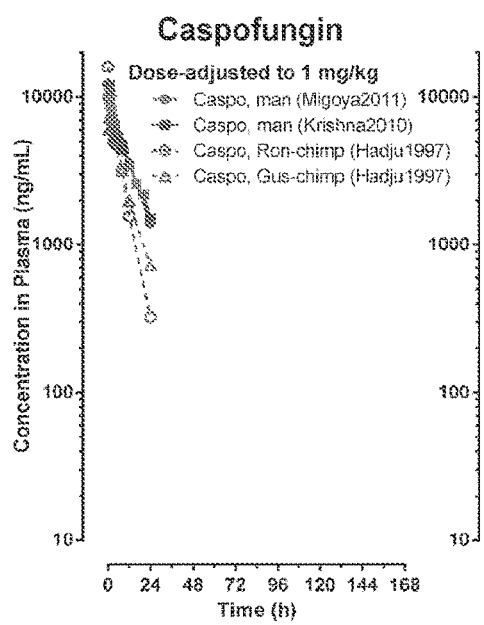
FIGS. 17A-17C are graphs depicting the pharmacokinetic curves observed for IV administered caspfungin (FIG. 17A, chimpanzee and man, see Haj du et al., Antimicrobial Agents and Chemotherapy, 41:2339 (1997)), IV administered anidulafungin (FIG. 17B, chimpanzee and man, see CDER package submitted to the FDA for Eraxis), and IV administered compound 22 (FIG. 17C, chimpanzee, see Example 8).
Figure 17B:
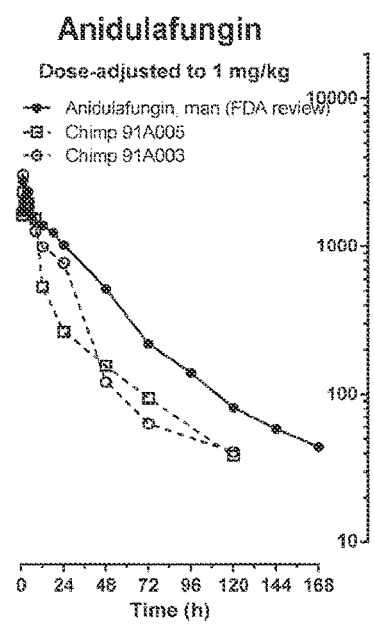
Figure 17C:
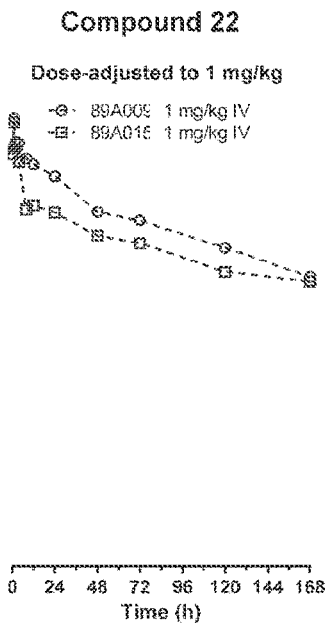

Compound 22 exhibits a longer half-life and lower clearance (higher AUC for given dose) than does anidulafungin in chimpanzees. Based on PK data for caspofungin (literature) and anidulafungin (Seachaid), it appears that the chimp is a good model for echinocandin PK (see FIGS. 17A-17C, human (solid lines) and chimp (dotted lines) from 1-mg/kg IV dose). Existing studies on this class of compounds in humans and chimpanzees suggest that the human clearance will be equal or lower (i.e. "better") than values observed from the chimpanzee.

The PK performance of compound 22 administered orally to chimpanzees was also evaluated. Compound 22 formulated with 5% citric acid resulted in an oral bioavailability of 4-5%. Levels of 600 to 1200 ng/mL were achieved after a single oral dose in chimps (see FIG. 18). The low clearance and long half-life of compound 22 should enable QD/BID oral dosing that permits accumulation or maintenance of therapeutic plasma concentrations. For example, compound 22 can be administered every 5-8 days as an intravenous infusion or bolus. Alternatively, compound 22 can be administered in an intravenous loading dose, followed by maintenance dosing for as long as is desired to maintain a therapeutically effective circulating concentration. Furthermore, the desirable pharmacokinetic properties of compound 22 allow for less frequent dosing.

Example 9. Half Lives of Echinocandins in Mammals

The circulating half lives of echinocandin class compounds are provided in Table 11.

TABLE 11

| | Half-life (h) | | | |
|---|---|---|---|---|
| Organism | Caspo-fungin | Mica-fungin | Anidula-fungin | Compound 22* |
| Mouse | 6-7 | 7-13 | 14-20 | 44-71 |
| Rat | 6-7 | 5 | 18, 22* | 30 |
| Dog | NA | NA | 12*, 15 | 53 |
| Monkey | 5-6 (rhesus) | NA | 8* | 40 |
| Chimpanzee | 6-7 | — | 30* | 81 |
| Rabbit | 2-3 | 3 | 4-6 | — |
| Man | 9-11 | 10-17 | 24-26 | — |

*measurements from assays conducted by applicant, others are literature values.

Example 10. Formulation for Subcutaneous and/or Intravenous Bolus Administration of Compound 22

The following formulations can be used in the methods, kits, and compositions of the invention. Exemplary subcutaneous and/or intravenous bolus formulations of the invention are described in Table 12.

TABLE 12

| Formulation | Composition | Concentration |
|---|---|---|
| Formulation SC1 | Compound 22 | 2.42% (w/w) |
| | Tween 20 | 1.44% (w/w) |
| | 100 mM Acetate Buffer pH 4.5 | 96.14% (w/w) |
| Formulation SC2 | Compound 22 | 0.28% (w/w) |
| | Tween 20 | 0.40% (w/w) |
| | 10 mM Acetate Buffer pH 4.5 | 99.32% (w/w) |
| Formulation SC3 | Compound 22 | 1.38% (w/w) |
| | Tween 20 | 0.39% (w/w) |
| | 50 mM Acetate Buffer pH 4.5 | 98.23% (w/w) |
| Formulation SC4 | Compound 22 | 16.5% (w/w) |
| | Tween 20 | 0.8% (w/w) |
| | 10 mM Acetate Buffer pH 5.5 | 82.7% (w/w) |
| Formulation SC5 | Compound 22 | 21.5% (w/w) |
| | Sterile water (pH adjusted to 5.5) | 78.5% (w/w) |
| Formulation SC6 | Compound 22 | 17.3% (w/w) |
| | Sterile water (pH adjusted to 6.0) | 67.7% (w/w) |
| | Glycerol, USP | 15.0% (w/w) |
| Formulation SC7 | Compound 22 | 13.0% (w/w) |
| | Tween 20 | 4.4% (w/w) |
| | 10 mM Acetate Buffer pH 6.0 | 86.6% (w/w) |

Example 11. Formulation for Intravenous Infusion of Compound 22

The following formulations can be used in the methods, kits, and compositions of the invention. Exemplary intravenous infusion formulations of the invention are described in Table 13. The formulations can be added to an IV bag for infusion into a subject.

TABLE 13

| Formulation | Composition | Concentration |
|---|---|---|
| Formulation IV1 | Compound 22 | 0.33% (w/w) |
| | Sterile water | 99.67% (w/w) |
| Formulation IV2 | Compound 22 | 0.33% (w/w) |
| | 20 mM Sodium Acetate, pH 4.5 | 99.67% (w/w) |
| Formulation IV3 | Compound 22 | 0.33% (w/w) |
| | 20 mM Sodium Acetate, pH 6.0 | 99.67% (w/w) |
| Formulation IV4 | Compound 22 | 0.33% (w/w) |
| | 20 mM Sodium Lactate, pH 4.5 | 99.67% (w/w) |
| Formulation IV5 | Compound 22 | 0.33% (w/w) |
| | 20 mM Sodium Lactate, pH 6.0 | 99.67% (w/w) |
| Formulation IV6 | Compound 22 | 0.33% (w/w) |
| | Tween 80 | 1.0% (w/w) |
| | 30 mM Sodium Lactate, pH 4.5 | 98.67% (w/w) |
| Formulation IV7 | Compound 22 | 0.33% (w/w) |
| | Tween 80 | 1.0% (w/w) |
| | 30 mM Sodium Lactate, pH 6.0 | 98.67% (w/w) |
| Formulation IV8 | Compound 22 | 0.33% (w/w) |
| | Tween 80 | 0.60% (w/w) |
| | Mannitol | 0.66% (w/w) |
| | 30 mM Sodium Lactate, pH 4.5 | 98.41% (w/w) |
| Formulation IV9 | Compound 22 | 0.33% (w/w) |
| | Tween 80 | 0.60% (w/w) |
| | Mannitol | 0.66% (w/w) |
| | 30 mM Sodium Lactate, pH 6.0 | 98.41% (w/w) |
| Formulation IV10 | Compound 22 | 0.33% (w/w) |
| | Fructose | 0.33% (w/w) |
| | Mannitol | 0.66% (w/w) |
| | 20 mM Sodium Lactate, pH 4.5 | 98.68% (w/w) |
| Formulation IV11 | Compound 22 | 0.33% (w/w) |
| | Fructose | 0.33% (w/w) |
| | Mannitol | 0.66% (w/w) |
| | 20 mM Sodium Lactate, pH 6.0 | 98.68% (w/w) |
| Formulation IV12 | Compound 22 | 0.33% (w/w) |
| | Mannitol | 0.66% (w/w) |
| | 20 mM Sodium Lactate, pH 6.0 | 99.0% (w/w) |
| Formulation IV13 | Compound 22 | 0.33% (w/w) |
| | Mannitol | 0.66% (w/w) |
| | 20 mM Sodium Lactate, pH 5.0 | 99.0% (w/w) |
| Formulation IV14 | Compound 22 | 0.33% (w/w) |
| | Tween 80 | 0.60% (w/w) |
| | Mannitol | 1.32% (w/w) |
| | 30 mM Sodium Lactate, pH 6.0 | 97.75% (w/w) |

Example 12. Lyophilized Formulations for Intravenous Infusion of Compound 22

The following lyophilized formulations can be used in the methods, kits, and compositions of the invention. Exemplary lyophilized formulations of the invention are described in Table 14. The formulations can be reconstituted and added to an IV bag for infusion into a subject.

TABLE 14

| Formulation | Composition | Concentration |
|---|---|---|
| Formulation L1 | Compound 22 | 66.79% (w/w) |
| | Sodium Acetate buffer, pH 4.5 | 33.21% (w/w) |
| Formulation L2 | Compound 22 | 66.79% (w/w) |
| | Sodium Acetate buffer, pH 6.0 | 33.21% (w/w) |
| Formulation L3 | Compound 22 | 25% (w/w) |
| | Mannitol | 50% (w/w) |
| | Fructose | 25% (w/w) |
| Formulation L4 | Compound 22 | 24.9% (w/w) |
| | Mannitol | 49.8% (w/w) |
| | Sodium Lactate buffer | 25.2% (w/w) |
| Formulation L5 | Compound 22 | 24.81% (w/w) |
| | Tween 80 | 75.19% (w/w) |
| Formulation L6 | Compound 22 | 21.27% (w/w) |
| | Tween 80 | 64.44% (w/w) |
| | Sodium Lactate buffer, pH 6.0 | 14.30% (w/w) |
| Formulation L7 | Compound 22 | 21.40% (w/w) |
| | Mannitol | 42.81% (w/w) |
| | Fructose | 21.40% (w/w) |
| | Sodium Lactate buffer, pH 4.5 | 14.39% (w/w) |
| Formulation L8 | Compound 22 | 17.16% (w/w) |
| | Mannitol | 34.31% (w/w) |
| | Tween 80 | 31.23% (w/w) |
| | Sodium Lactate buffer, pH 6.0 | 17.30% (w/w) |
| Formulation L9 | Compound 22 | 17.16% (w/w) |
| | Mannitol | 34.31% (w/w) |
| | Tween 80 | 31.23% (w/w) |
| | Sodium Lactate buffer, pH 4.5 | 17.30% (w/w) |

TABLE 14-continued

| Formulation | Composition | Concentration |
|---|---|---|
| Formulation L10 | Compound 22 | 14.65% (w/w) |
| | Mannitol | 29.30% (w/w) |
| | Fructose | 14.65% (w/w) |
| | Tween 80 | 26.67% (w/w) |
| | Sodium Lactate buffer, pH 4.5 | 14.73% (w/w) |

Example 13. Pharmacokinetics of Compound 22 Subcutaneously (SC) Administered

Pharmacokinetic studies were performed in rats (2.8 mg/kg IV, 2.8 mg/kg SC injection to the back, 2.8 mg/kg SC injection to the abdomen, and 2.8 mg/kg SC injection to the hind foot) and Chinese cynomolgus monkeys (2.13 mg/kg IV and 2.8 mg/kg SC). Blood samples were collected from each animal at predetermined times after dosing. Whole blood samples were centrifuged to isolate plasma. The plasma samples were analyzed for compound 22 using LC-MS/MS.

Figure 19:
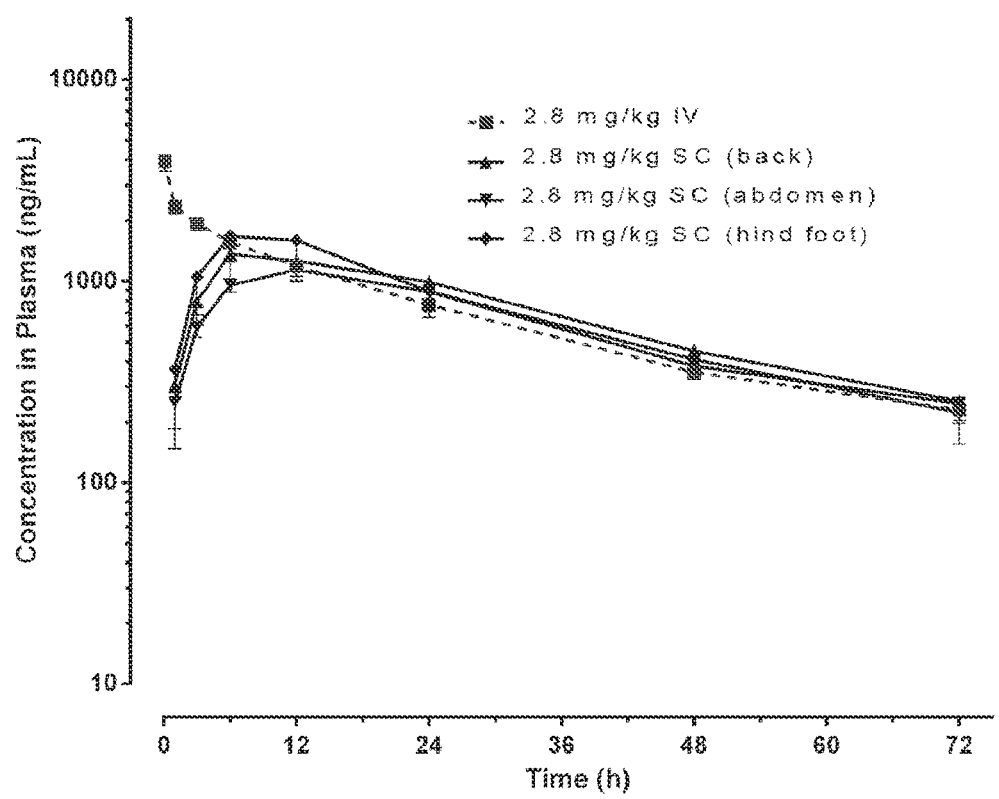
FIG. 19 is a graph depicting the pharmacokinetic curves observed in rats for compound 22 administered intravenously and subcutaneously.
Figure 20:
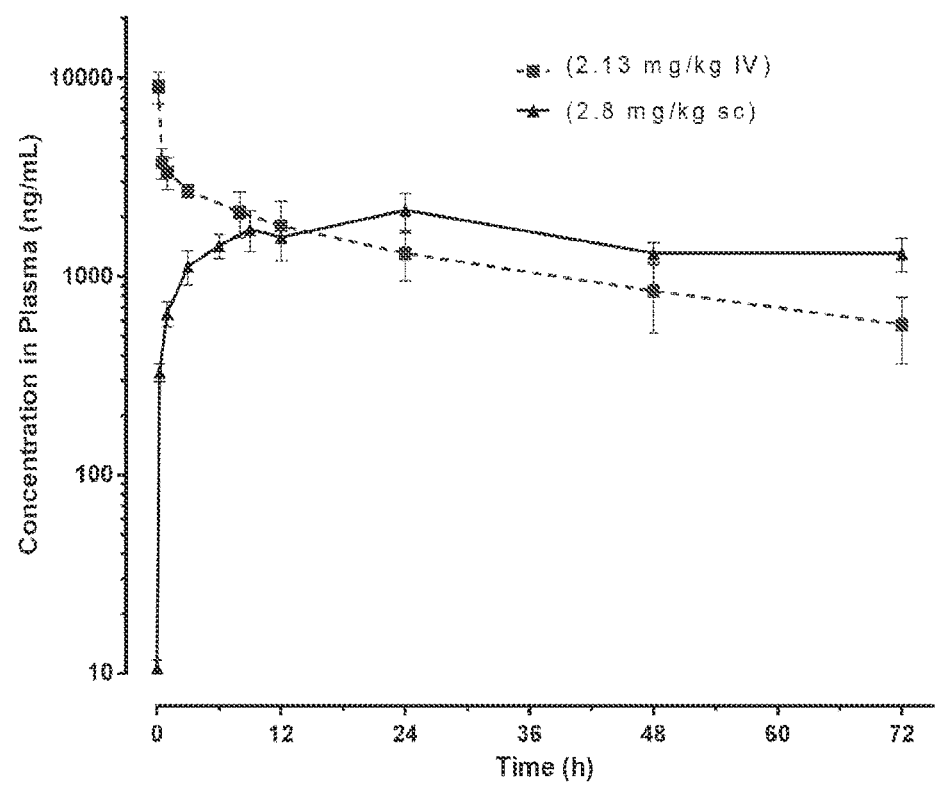
FIG. 20 is a graph depicting the pharmacokinetic curves observed in monkeys for compound 22 administered intravenously and subcutaneously.
Figure 21:
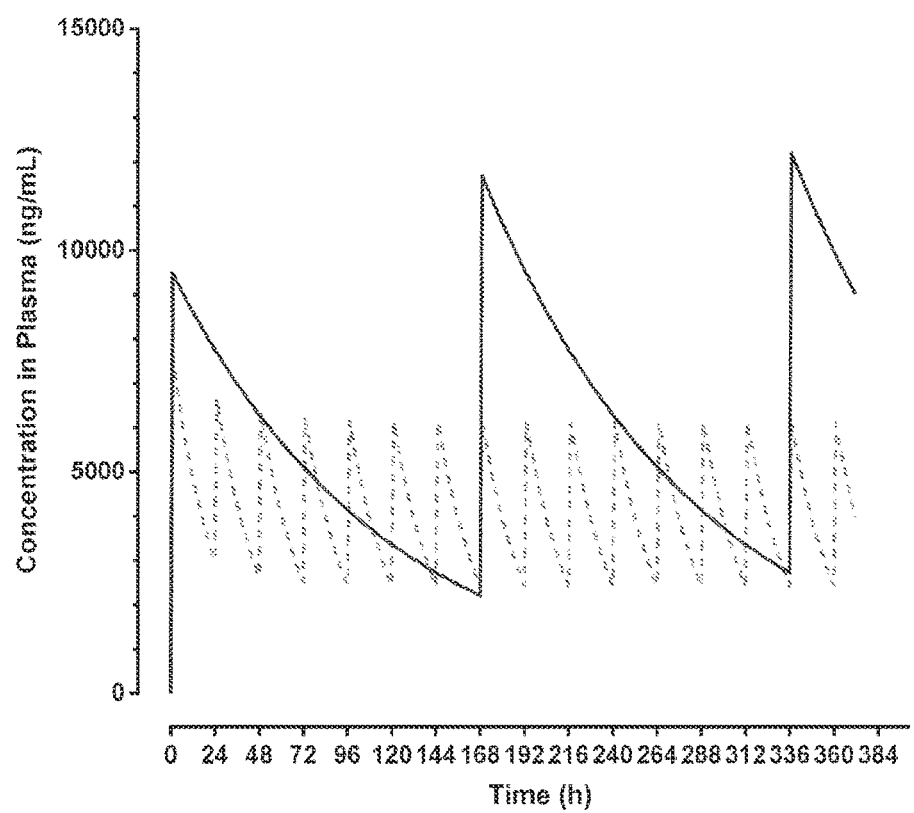
FIG. 21 is a graph depicting the calculated circulating concentrations in human subjects for 200 mg compound 22 administered intravenously once every 7 days (solid line) and anidulafungin 200 mg administered intravenously on day one, followed by 100 mg daily administered intravenously (dotted line). The anidulafungin curve is based upon the curves reported in the package insert for Eraxis. The curve for compound 22 was calculated based upon a clearance of 3.4 mL/hr/kg and a plasma half life of 80 hr (values based upon chimpanzee studies).
Figure 22:
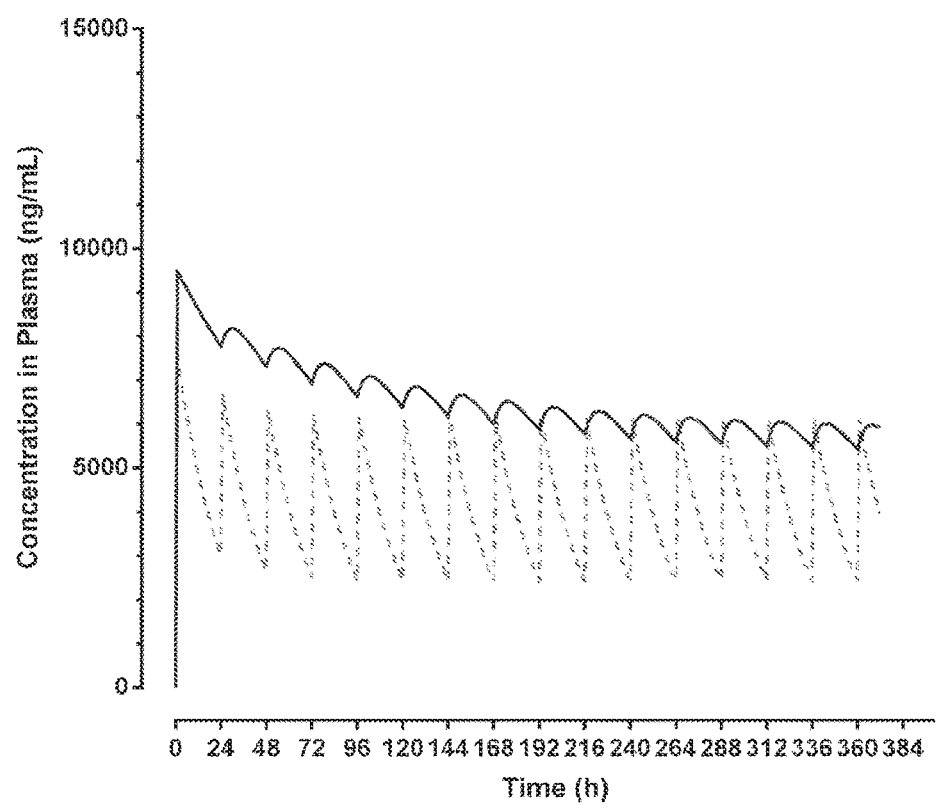
FIG. 22 is a graph depicting the calculated circulating concentrations in human subjects for 200 mg compound 22 administered intravenously on day one, followed by 500 mg daily oral administration (solid line), and anidulafungin 200 mg administered intravenously on day one, followed by 100 mg daily administered intravenously (dotted line). The anidulafungin curve is based upon the curves reported in the package insert for Eraxis. The curve for compound 22 was calculated based upon a clearance of 3.4 mL/hr/kg, a plasma half life of 80 hr, and an oral bioavailability of 5% (values based upon chimpanzee studies).

The SC monkey study was performed using formulation SC1 (see Table 12). The rat studies were performed using formulation SC2 (see Table 12) for the abdomen and back injections, and formulation SC3 (see Table 12) for the hind foot injection. The PK curves are depicted in FIG. 19 (rat) and 20 (monkey). The results demonstrate that the regimens of the invention can include one or more subcutaneous administrations to produce a therapeutically effective circulating concentration of compound 22.

Example 14. Stability

Compound 22 exhibits commercially acceptable stability upon storage as a solid or in solution.

Solutions of compound 22 formulated for injection in 5% Dextrose Solution (at 1.3 mg/mL and 1.1 mg/mL) and in 0.9% Sterile Saline Solution (1.3 mg/mL) were stored at room temperature in a clear vial under ambient light and monitored for decomposition by HPLC. All solutions exhibited only minor losses in potency (less than 5%) over a period of 4 months.

Accelerated aging at 40° C. in a clear vial under ambient light was performed for compound 22 formulated with 5% Dextrose Solution (3.3 mg/mL), 20 mM Acetate Buffer pH 4.5 (3.3 mg/mL), and 20 mM Lactate pH 6.0 (3.3 mg/mL). All solutions exhibited only minor losses in potency (less than 5%) over a period of 4 months.

Lyophilized formulations L6 and L7 (see Table 14) were observed to exhibit only minor losses in potency (less than 5%) over a period of 3 months.

No stabilizers were utilized in the stability studies.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

This application claims benefit of the U.S. Provisional Application No. 61/612,676, filed Mar. 19, 2012, and U.S. Provisional Application No. 61/707,142, filed Sep. 28, 2012, each of which is incorporated herein by reference.

Other embodiments are within the claims.

What is claimed is:

1. A method of treating or preventing a fungal infection in a subject, the method comprising administering to the subject by intravenous infusion an aqueous solution comprising from 0.50 mg/mL to 3 mg/mL of compound 22 having the structure:

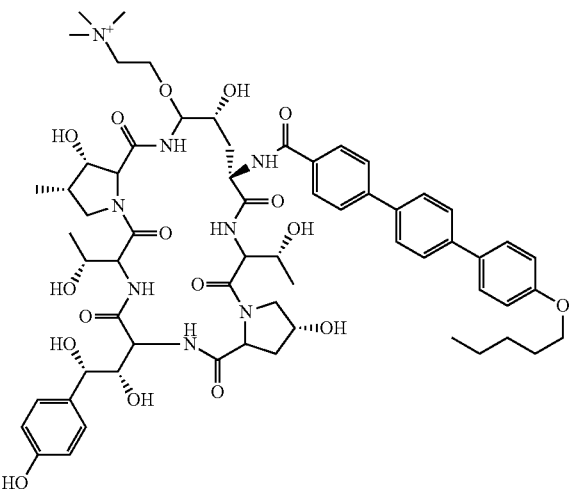 [SMILES: CCCCCOc1ccc(-c2ccc(-c3ccc(C(=O)N[C@H]4C[C@@H](O)C(OCC[N+](C)(C)C)NC(=O)C5[C@@H](O)[C@@H](C)CN5C(=O)C([C@@H](C)O)NC(=O)C([C@H](O)[C@@H](O)c5ccc(O)cc5)NC(=O)C5C[C@@H](O)CN5C(=O)C([C@@H](C)O)NC4=O)cc3)cc2)cc1]

or a pharmaceutically acceptable salt thereof.

2. A method of treating or preventing a fungal infection in a subject, the method comprising administering to the subject by intravenous bolus an aqueous solution comprising from 25 mg/mL to 500 mg/mL of compound 22 having the structure:

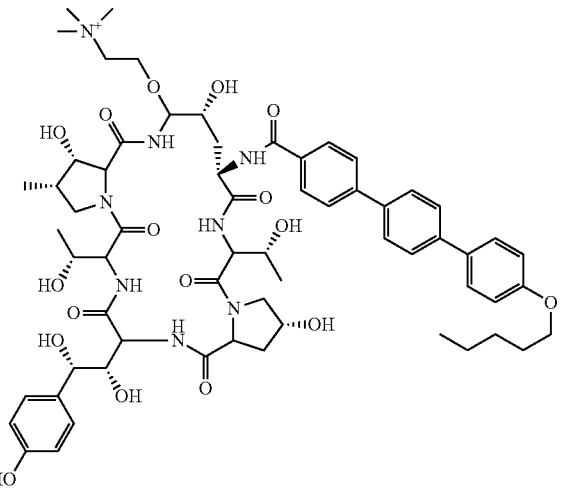

or a pharmaceutically acceptable salt thereof.

3. A device for injecting into a subject an aqueous solution comprising compound 22 having the structure:
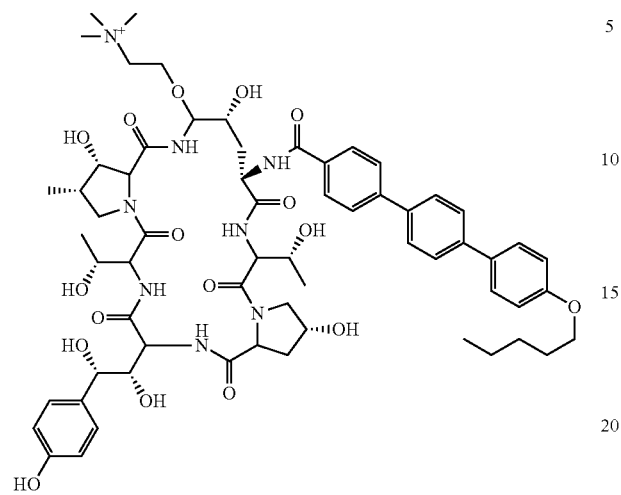
or a pharmaceutically acceptable salt thereof, wherein the device comprises a container holding from 0.05 mL to 10 mL of said aqueous solution and a needle.
* * * * *